US008486661B2

(12) United States Patent
Kniessel et al.

(10) Patent No.: US 8,486,661 B2
(45) Date of Patent: *Jul. 16, 2013

(54) POLYNUCLEOTIDES ENCODING ANTIBODIES AGAINST SCLEROSTIN AND USES THEREFOR

(75) Inventors: Michaela Kniessel, Basel (CH); Christine Halleux, Dornach (CH); Shou-Ih Hu, New Providence, NJ (US); Beate Diefenbach-Streiber, Windach (DE); Josef Prassler, Germering (DE)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/547,598

(22) Filed: Jul. 12, 2012

(65) Prior Publication Data

US 2012/0276591 A1 Nov. 1, 2012

Related U.S. Application Data

(63) Continuation of application No. 12/944,019, filed on Nov. 11, 2010, now Pat. No. 8,246,953, which is a continuation of application No. 12/249,050, filed on Oct. 10, 2008, now Pat. No. 7,879,322.

(30) Foreign Application Priority Data

Oct. 12, 2007 (EP) .................................... 07118414
Feb. 25, 2008 (EP) .................................... 08151911
Jul. 29, 2008 (EP) .................................... 08161342

(51) Int. Cl.
*C12N 15/13* (2006.01)
*C12N 15/12* (2006.01)
*C12N 15/63* (2006.01)
*C12N 15/66* (2006.01)
*C12N 5/07* (2010.01)

(52) U.S. Cl.
USPC .. 435/69.1; 435/325; 435/252.3; 435/254.11; 435/320.1; 435/326; 435/328; 435/331; 536/23.1; 536/23.53

(58) Field of Classification Search
None
See application file for complete search history.

(56) References Cited

U.S. PATENT DOCUMENTS

| 6,331,415 | B1 | 12/2001 | Cabilly |
| 6,455,275 | B1 | 9/2002 | Axel |
| 7,138,501 | B2 | 11/2006 | Ruben |
| 7,220,840 | B2 | 5/2007 | Ruben |
| 7,879,322 | B2 | 2/2011 | Kniessel et al. |
| 8,246,953 | B2 * | 8/2012 | Kniessel et al. ........... 424/130.1 |

FOREIGN PATENT DOCUMENTS

| JP | 509615 | 1/1993 |
| JP | 2010-524846 A | 7/2010 |
| WO | WO 00/22111 | 4/2000 |
| WO | WO 00/32773 | 6/2000 |
| WO | WO 01/05950 | 1/2001 |
| WO | WO 02/02641 | 1/2002 |
| WO | WO 03/055979 | 7/2003 |
| WO | WO 03/106054 | 12/2003 |
| WO | WO 03/106657 | 12/2003 |
| WO | WO 2005/003158 | 1/2005 |
| WO | WO 2005/014650 | 2/2005 |
| WO | WO 2006/102070 | 9/2006 |
| WO | WO 2006/102671 | 9/2006 |
| WO | WO 2006/119062 | 11/2006 |
| WO | WO 2006/119107 | 11/2006 |
| WO | WO 2007/070538 | 1/2007 |
| WO | WO 2007/084344 | 1/2007 |
| WO | WO 2008/061013 | 5/2008 |
| WO | WO 2008/115732 | 9/2008 |
| WO | WO 2008/133722 | 11/2008 |
| WO | WO 2009/039175 | 3/2009 |
| WO | WO 2009/047356 | 4/2009 |
| WO | WO 2009/079471 | 6/2009 |
| WO | WO 2009/131553 | 10/2009 |

OTHER PUBLICATIONS

International Search Report; WO 2009/047356; Feb. 20, 2009.
Balemans, et al., "Identification of a 52 kb deletion downstream of the SOST gene in patients with van Buchem disease", J. Med. Genet, 2002 vol. 39 No. 2 pp. 91-97.
Brunkow, et al., "Bone Dysplasia Sclerosteosis Results from Loss of the SOST Gene Product, a Novel Cystine Knot-Containing Protein", Am. J. Hum. Genet., 2001 vol. 68 No. 3 pp. 577-589.
Chen, et al., "Selection and Analysis of an Optimized Anti-VEGF Antibody: Crystal Structure of an Affinity-matured Fab in Complex with Antigen", J. Mol. Biol., 1999 vol. 293 No. 4 pp. 865-881.
Haenel, et al., "Characterization of high-affinity antibodies by electrochemiluminescence-based equilibrium titration", Analytical Biochemistry, 2005 vol. 339 No. 1 pp. 182-184.
Keller, et al., "SOST is a target gene for PTH in bone", Bone, 2005 vol. 37 No. 2 pp. 148-158.
Knappik, et al., "Fully Synthetic Human Combinatorial Antibody Libraries (HuCAL) Based on Modular Consensus Frameworks and CDRs Randomized with Trinucleotides", J. Mol. Biol., 2000 vol. 296 No. 1 pp. 57-86.
Krebs, et al., "High-throughput generation and engineering of recombinant human antibodies", Journal of Immunological Methods, 2001 vol. 254 pp. 67-84.
Li, et al., "Sclerostin Binds to LRP5/6 and Antagonizes Canonical Wnt Signaling" The Journal of Biological Chemistry, 2005 vol. 280 No. 20 pp. 19883-19887.
Loots, et al., "Genomic deletion of a long-range bone enhancer misregulates sclerostin in Van Buchem disease", Genome Res., 2005 vol. 15 No. 7 pp. 928-935.
Low, et al., "Mimicking Somatic Hypermutation: Affinity Maturation of Antibodies Displayed on Bacteriophage Using a Bacterial Mutator Strain", J. Mol. Biol., 1996 vol. 260 No. 3 pp. 359-368.

(Continued)

*Primary Examiner* — Elizabeth C Kemmerer
(74) *Attorney, Agent, or Firm* — Leslie Fischer

(57) ABSTRACT

The present invention relates to antibodies against sclerostin and compositions and methods of use for said antibodies to treat a pathological disorder that is mediated by sclerostin or disease related to bone abnormalities such as osteoporosis.

19 Claims, 15 Drawing Sheets

OTHER PUBLICATIONS

Rauchenberger, et al., "Human Combinatorial Fab Library Yielding Specific and Functional Antibodies against the Human Fibroblast Growth Factor Receptor 3", The Journal of Biological Chemistry, 2003 vol. 278 No. 40 pp. 38194-38205.

Semenov, et al., "LRP5 Mutations Linked to High Bone Mass Diseases Cause Reduced LRP5 Binding and Inhibition by SOST", The Journal of Biological Chemistry, 2006 vol. 281 No. 50 pp. 38276-38284.

Van Bezooijen, et al., "Wnt but Not BMP Signaling Is Involved in the Inhibitory Action of Sclerostin on BMP-Stimulated Bone Formation", Journal of Bone and Mineral Research, 2007 vol. 22 No. 1 pp. 19-28.

Wirnekas., et al., "Trinucleotide phosphoramidites: ideal reagents for the synthesis of mixed oligonucleotides for random mutagenesis", Nucleic Acids Research, 1994 vol. 22 No. 25 pp. 5600-5607.

Winkler, et al., "Osteocyte control of bone formation via sclerostin, a novel BMP antagonist", The EMBO Journal, 2003 vol. 22 No. 23 pp. 6267-6276.

Winkler, et al., "Sclerostin Inhibition of Wnt-3a-induced C3H10T1/2 Cell Differentiation is Indirect and Mediated by Bone Morphogenetic Proteins", The Journal of Biological Chemistry, 2005 vol. 280 No. 4 pp. 2498-2502.

Avsian-Kretchmer et al., "Comparative Genomic Analysis of the Eight-Membered Ring Cystine Knot-Containing Bone Morphogenetic Protein Antagonists", Molecular Endocrinology, vol. 18, No. 1, pp. 1-12, (2004).

Balemans, et al., "Increased bone density in sclerosteosis is due to the deficiency of a novel secreted protein (SOST)", Human Molecular Genetics, vol 10, No. 5, pp. 537-543 (2001).

Gardner, et al., "Bone Mineral Density in sclerosteosis: Affected Individuals and Gene Carriers", J. Clinical Endocrinology & Metabolism, vol. 90, No. 12, pp. 6392-6395 (2005).

Van Bezooijen, et al., "SOST/sclerostin, an osteocyte-derived negative regulator of bone formation", Cytokine Growth factor Reviews, vol. 16, pp. 319-327 (2005).

Grey, Andrew, "Emerging pharmacologic therapies for osteoporosis" Expert Opinion on Emerging Drugs, vol. 12, No. 3, pp. 493-508 (2007).

Ke et al., "Bone anabolism achieved by reducing sclerostin", (2006). XP002469781.

Warmington et al., "Sclerostin Monoclonal Antibody Treatment of Osteoporotic Rats Completely Reverses One Year of Ovariectomy-Induced Systemic Bone Loss", Journal of bone and mineral research, vol. 20, No. 9, p. 22, Pres 1082, (2005), XP008078248.

Ominsky et al., "Sclerostin Monoclonal Antibody Treatment Increases Bone Strengths in Aged Osteopenic Ovariectomized Rats", Journal of bone and mineral research, vol. 21, No. 1, p. 44. Pres 1161, (2006). XF008078247.

Warmington et al., Journal of Bone and mineral research, vol. 19. pp. S56-S57, (2004), XP009072609.

Van Bezooijen et al., "Bone morphogenetic proteins and their antagonists: The iclerostin paradigm", Journal of endoctinological investigation, vol. 28, No. 8, pp. 15-17, (2005), XP008078167.

Kyojo, Clinical Calcium vol. 17, No. 10, pp. 1554-1558, (2007), XP008088787.

Paul, Fundamental Immunology, Third Edition, Raven Press, New York, 1993, pp. 292-295.

Rudikoff et al., "Single amino acid substitution altering antigen-binding specificity", PNAS USA, vol. 79. pp. 1979-1983, Mar. 1982.

Lewiecky et al., "Sclerostin monoclonal antibody therapy with AMG 785: a potential treatment for osteoporosis", expert Opin. Biol. Ther., 11(1) pp. 117-127, (2011).

Kumagi et al., "Antigen-Antibody Binding", Encyclopedia of Life Sciences, Nature Publishing Group, pp. 1-7, (2001) (www.els.net).

Finkelstein et al., "The Effects of Parathyroid Hormone, Alendronate; or Both in Men with Osteoporosis", New England Journal of Medicine, vol. 349, No. 13, pp. 1216-1226, (2003).

Black et al., "The Effects of Parathyroid Hormone and Alendronate Alone or in combination in Postmenopausal Osteoporosis", New England Journal of Medicine, vol. 349, No. 13, pp. 1207-1215, (2003).

Forteo Leaflet, Highlights of Prescribing Information, Manufactured by Lilly France for Eli Lilly and Company, 2002.

Lintern et al., "Characterization of Wise Protein and Its Molecular Mechanism to Interact with both Wnt and BMP Signals", Journal of Biological Chemistry, vol. 28, No. 34, pp. 23159-23168, (Aug. 21, 2009).

Holdsworth et al., "Characterization of the interaction of Scleroslin with Low Density Lipoprotein Receptor-related Protein (LRP) Family of Wnt Co-receptors", Journal of Biological Chemistry, vol. 287, No. 32, pp. 26464-26477, Aug. 3, 2012.

Veverka et al., "Characterization of the Structural Features and Interactions of Scleroslin", Journal of Biological Chemistry, vol. 284, No. 16, pp. 10890-10900, Apr. 17, 2009.

\* cited by examiner

Fig. 2
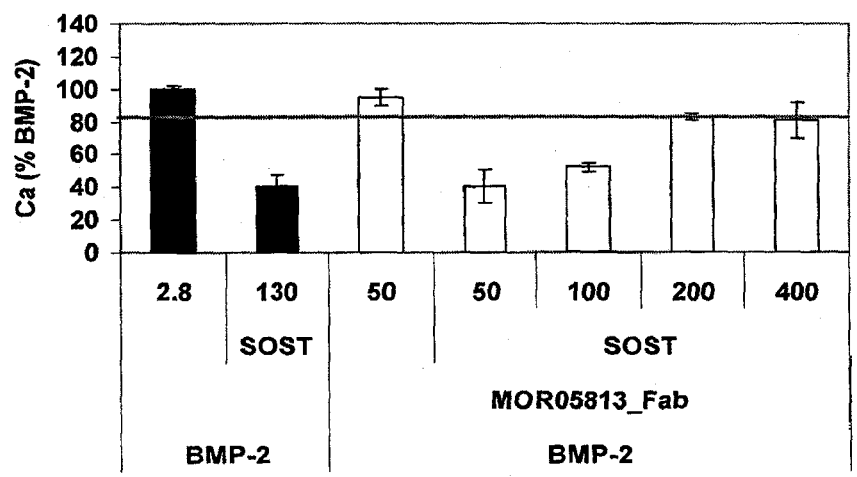
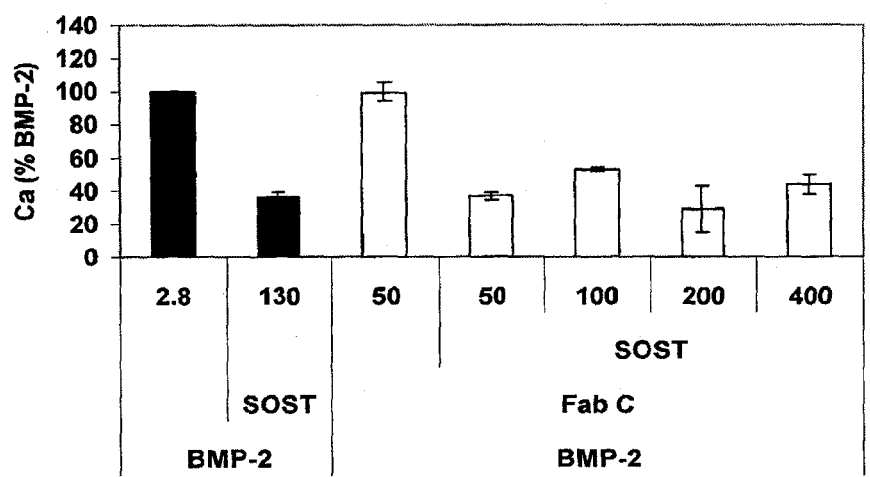

Fig. 4
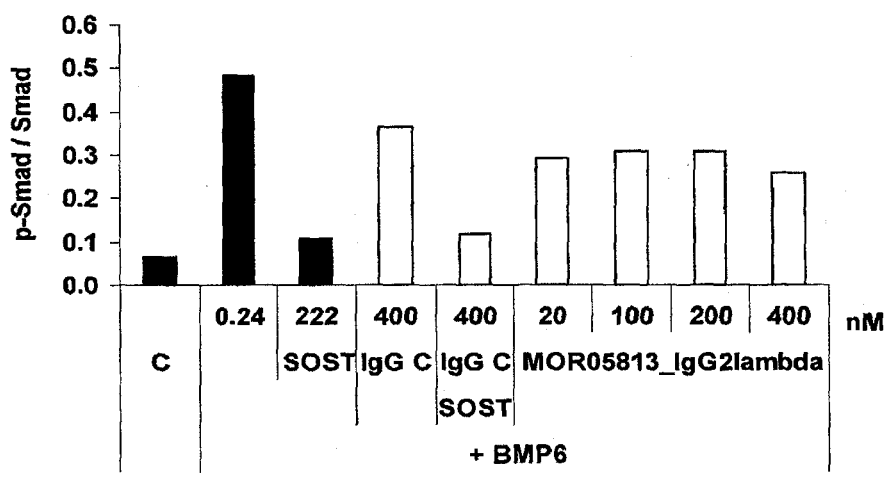
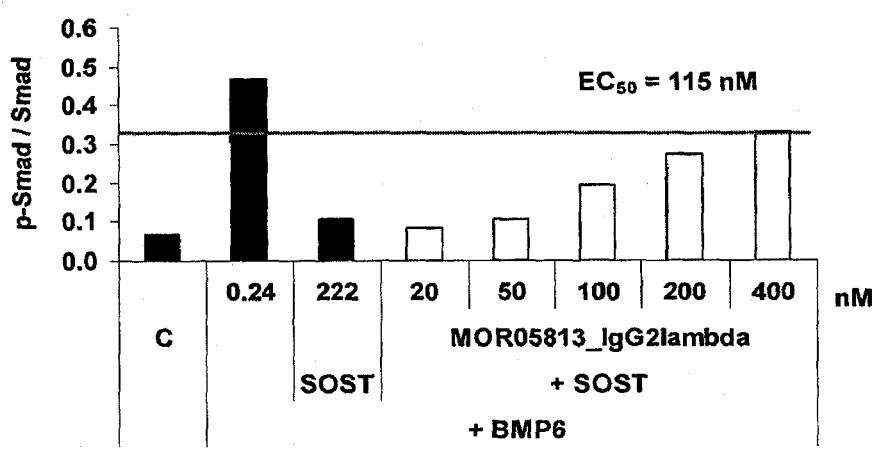

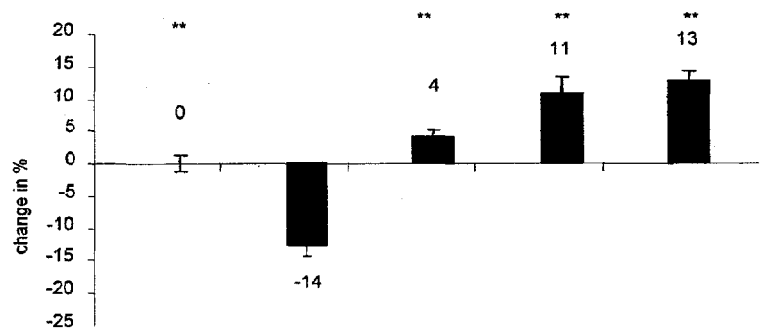
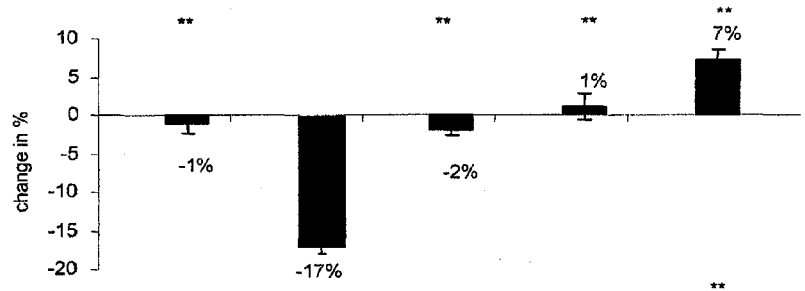
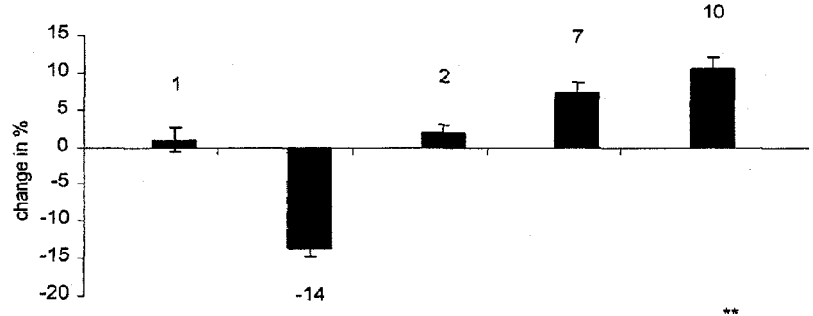
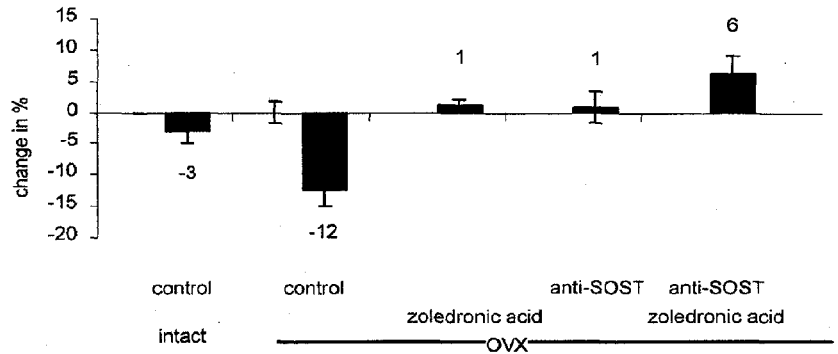
Fig. 21

Fig. 22
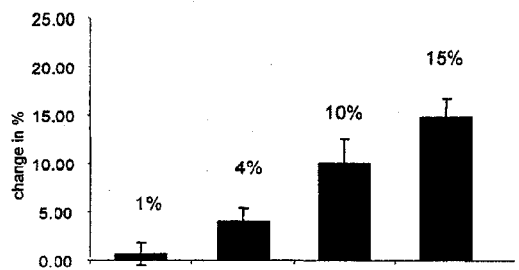
A
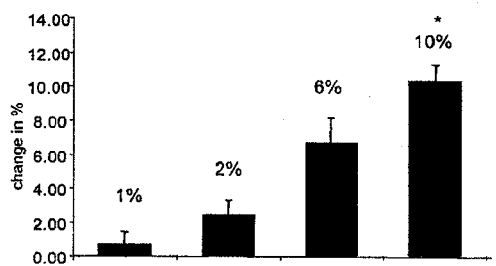
B
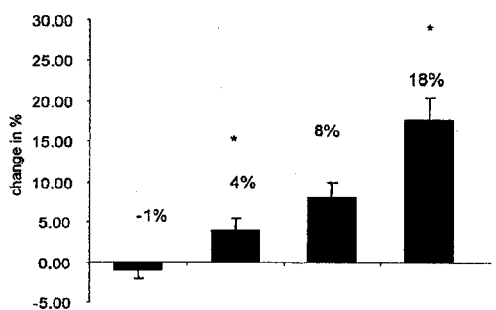
C
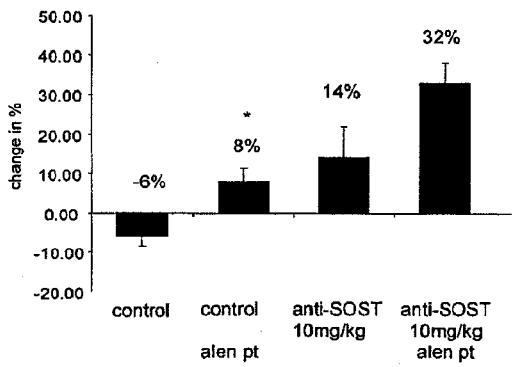
D

Fig. 23
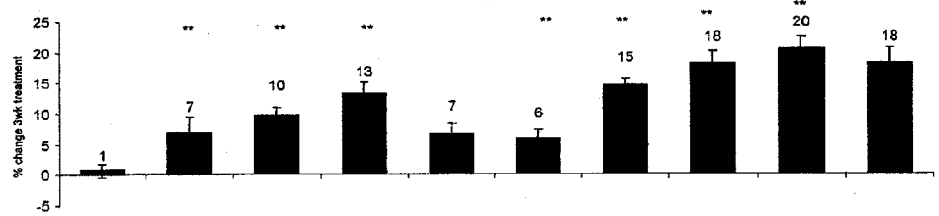
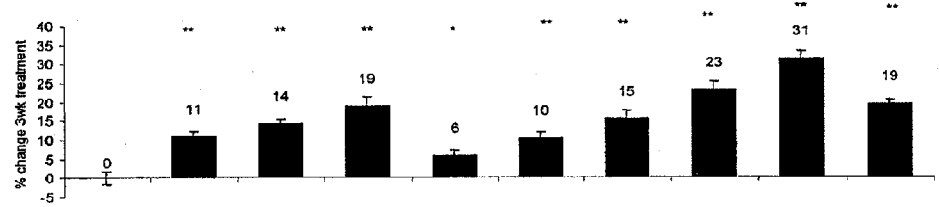
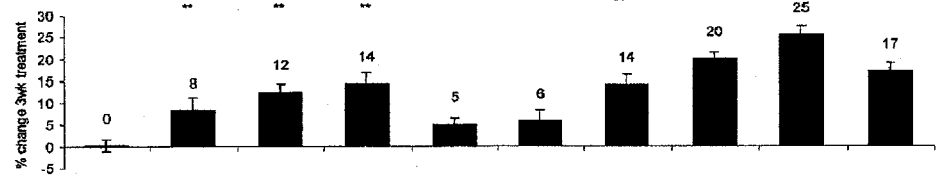
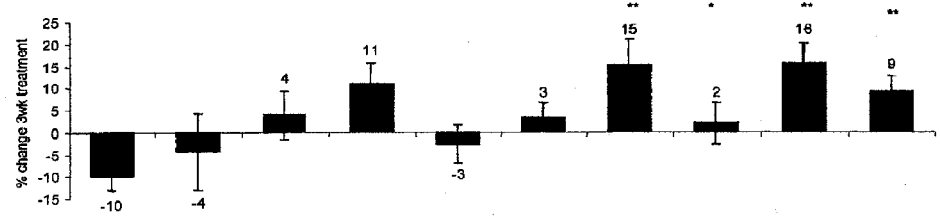

SEQUENCE LISTING

```
<160> NUMBER OF SEQ ID NOS: 171

<210> SEQ ID NO 1
<211> LENGTH: 10
<212> TYPE: PRT
<213> ORGANISM: Homo sapiens

<400> SEQUENCE: 1

Gly Phe Thr Phe Ser Ser Tyr Val Met Asn
1               5                   10

<210> SEQ ID NO 2
<211> LENGTH: 10
<212> TYPE: PRT
<213> ORGANISM: Homo sapiens
```

```
<400> SEQUENCE: 2

Gly Phe Thr Phe Arg Ser His Trp Leu Ser
1               5                   10

<210> SEQ ID NO 3
<211> LENGTH: 10
<212> TYPE: PRT
<213> ORGANISM: Homo sapiens

<400> SEQUENCE: 3

Gly Phe Thr Phe Ser Ser Tyr Val Met Asn
1               5                   10

<210> SEQ ID NO 4
<211> LENGTH: 10
<212> TYPE: PRT
<213> ORGANISM: Homo sapiens

<400> SEQUENCE: 4

Gly Phe Thr Phe Arg Ser His Trp Leu Ser
1               5                   10

<210> SEQ ID NO 5
<211> LENGTH: 10
<212> TYPE: PRT
<213> ORGANISM: Homo sapiens

<400> SEQUENCE: 5

Gly Phe Thr Phe Arg Ser His Trp Leu Ser
1               5                   10

<210> SEQ ID NO 6
<211> LENGTH: 10
<212> TYPE: PRT
<213> ORGANISM: Homo sapiens

<400> SEQUENCE: 6

Gly Phe Thr Phe Arg Ser His Trp Leu Ser
1               5                   10

<210> SEQ ID NO 7
<211> LENGTH: 10
<212> TYPE: PRT
<213> ORGANISM: Homo sapiens

<400> SEQUENCE: 7

Gly Phe Thr Phe Arg Ser His Trp Leu Ser
1               5                   10

<210> SEQ ID NO 8
<211> LENGTH: 10
<212> TYPE: PRT
<213> ORGANISM: Homo sapiens

<400> SEQUENCE: 8

Gly Phe Thr Phe Arg Ser His Trp Leu Ser
1               5                   10

<210> SEQ ID NO 9
<211> LENGTH: 10
<212> TYPE: PRT
<213> ORGANISM: Homo sapiens

<400> SEQUENCE: 9
```

Gly Phe Thr Phe Arg Ser His Trp Leu Ser
1               5                   10

<210> SEQ ID NO 10
<211> LENGTH: 10
<212> TYPE: PRT
<213> ORGANISM: Homo sapiens

<400> SEQUENCE: 10

Gly Phe Thr Phe Arg Ser His Trp Leu Ser
1               5                   10

<210> SEQ ID NO 11
<211> LENGTH: 10
<212> TYPE: PRT
<213> ORGANISM: Homo sapiens

<400> SEQUENCE: 11

Gly Phe Thr Phe Arg Ser His Trp Leu Ser
1               5                   10

<210> SEQ ID NO 12
<211> LENGTH: 20
<212> TYPE: PRT
<213> ORGANISM: Homo sapiens

<400> SEQUENCE: 12

Trp Val Ser Phe Ile Ser Gly Asp Ser Ser Asn Thr Tyr Tyr Ala Asp
1               5                   10                  15

Ser Val Lys Gly
            20

<210> SEQ ID NO 13
<211> LENGTH: 20
<212> TYPE: PRT
<213> ORGANISM: Homo sapiens

<400> SEQUENCE: 13

Trp Val Ser Asn Ile Asn Tyr Asp Gly Ser Ser Thr Tyr Tyr Ala Asp
1               5                   10                  15

Ser Val Lys Gly
            20

<210> SEQ ID NO 14
<211> LENGTH: 20
<212> TYPE: PRT
<213> ORGANISM: Homo sapiens

<400> SEQUENCE: 14

Trp Val Ser Phe Ile Ser Gly Asp Ser Ser Asn Thr Tyr Tyr Ala Asp
1               5                   10                  15

Ser Val Lys Gly
            20

<210> SEQ ID NO 15
<211> LENGTH: 20
<212> TYPE: PRT
<213> ORGANISM: Homo sapiens

<400> SEQUENCE: 15

Trp Val Ser Asn Ile Asn Tyr Asp Gly Ser Ser Thr Tyr Tyr Ala Asp
1               5                   10                  15

Ser Val Lys Gly
            20

<210> SEQ ID NO 16
<211> LENGTH: 19
<212> TYPE: PRT
<213> ORGANISM: Homo sapiens

<400> SEQUENCE: 16

Trp Val Ser Val Thr Gly Val His Gly Asp Thr Tyr Tyr Ala Asp Ser
1               5                   10                  15

Val Lys Gly

<210> SEQ ID NO 17
<211> LENGTH: 19
<212> TYPE: PRT
<213> ORGANISM: Homo sapiens

<400> SEQUENCE: 17

Trp Val Ser Val Ile Gly Asn Trp Gly Asp Thr Tyr Tyr Ala Asp Ser
1               5                   10                  15

Val Lys Gly

<210> SEQ ID NO 18
<211> LENGTH: 19
<212> TYPE: PRT
<213> ORGANISM: Homo sapiens

<400> SEQUENCE: 18

Trp Val Ser Val Thr Thr His Gln Gly Tyr Thr Tyr Tyr Ala Asp Ser
1               5                   10                  15

Val Lys Gly

<210> SEQ ID NO 19
<211> LENGTH: 19
<212> TYPE: PRT
<213> ORGANISM: Homo sapiens

<400> SEQUENCE: 19

Trp Val Ser Ala Thr Asn Arg Tyr Gly Tyr Thr Tyr Tyr Ala Asp Ser
1               5                   10                  15

Val Lys Gly

<210> SEQ ID NO 20
<211> LENGTH: 20
<212> TYPE: PRT
<213> ORGANISM: Homo sapiens

<400> SEQUENCE: 20

Trp Val Ser Asn Ile Asn Tyr Asp Gly Ser Ser Thr Tyr Tyr Ala Asp
1               5                   10                  15

Ser Val Lys Gly
            20

<210> SEQ ID NO 21
<211> LENGTH: 19
<212> TYPE: PRT
<213> ORGANISM: Homo sapiens

<400> SEQUENCE: 21

Trp Val Ser Val Ile Thr Pro Tyr Gly Asp Thr Tyr Tyr Ala Asp Ser
1               5                   10                  15

Val Lys Gly

```
<210> SEQ ID NO 22
<211> LENGTH: 19
<212> TYPE: PRT
<213> ORGANISM: Homo sapiens

<400> SEQUENCE: 22

Trp Val Ser Val Ile Thr Pro Tyr Gly Asp Thr Tyr Tyr Ala Asp Ser
1               5                   10                  15
Val Lys Gly

<210> SEQ ID NO 23
<211> LENGTH: 15
<212> TYPE: PRT
<213> ORGANISM: Homo sapiens

<400> SEQUENCE: 23

Thr Phe Met His Gly His Leu Gly Gly Gly Leu Ser Met Asp Phe
1               5                   10                  15

<210> SEQ ID NO 24
<211> LENGTH: 8
<212> TYPE: PRT
<213> ORGANISM: Homo sapiens

<400> SEQUENCE: 24

Asp Thr Tyr Leu His Phe Asp Tyr
1               5

<210> SEQ ID NO 25
<211> LENGTH: 15
<212> TYPE: PRT
<213> ORGANISM: Homo sapiens

<400> SEQUENCE: 25

Thr Phe Met His Gly His Leu Gly Gly Gly Leu Ser Met Asp Phe
1               5                   10                  15

<210> SEQ ID NO 26
<211> LENGTH: 8
<212> TYPE: PRT
<213> ORGANISM: Homo sapiens

<400> SEQUENCE: 26

Asp Thr Tyr Leu His Phe Asp Tyr
1               5

<210> SEQ ID NO 27
<211> LENGTH: 8
<212> TYPE: PRT
<213> ORGANISM: Homo sapiens

<400> SEQUENCE: 27

Asp Thr Tyr Leu His Phe Asp Tyr
1               5

<210> SEQ ID NO 28
<211> LENGTH: 8
<212> TYPE: PRT
<213> ORGANISM: Homo sapiens

<400> SEQUENCE: 28

Asp Thr Tyr Leu His Phe Asp Tyr
1               5
```

```
<210> SEQ ID NO 29
<211> LENGTH: 8
<212> TYPE: PRT
<213> ORGANISM: Homo sapiens

<400> SEQUENCE: 29

Asp Thr Tyr Leu His Phe Asp Tyr
1               5

<210> SEQ ID NO 30
<211> LENGTH: 8
<212> TYPE: PRT
<213> ORGANISM: Homo sapiens

<400> SEQUENCE: 30

Asp Thr Tyr Leu His Phe Asp Tyr
1               5

<210> SEQ ID NO 31
<211> LENGTH: 8
<212> TYPE: PRT
<213> ORGANISM: Homo sapiens

<400> SEQUENCE: 31

Asp Thr Tyr Leu His Phe Asp Tyr
1               5

<210> SEQ ID NO 32
<211> LENGTH: 8
<212> TYPE: PRT
<213> ORGANISM: Homo sapiens

<400> SEQUENCE: 32

Asp Thr Tyr Leu His Phe Asp Tyr
1               5

<210> SEQ ID NO 33
<211> LENGTH: 8
<212> TYPE: PRT
<213> ORGANISM: Homo sapiens

<400> SEQUENCE: 33

Asp Thr Tyr Leu His Phe Asp Tyr
1               5

<210> SEQ ID NO 34
<211> LENGTH: 11
<212> TYPE: PRT
<213> ORGANISM: Homo sapiens

<400> SEQUENCE: 34

Ser Gly Asp Asn Ile Gly Ser Phe Tyr Val His
1               5                   10

<210> SEQ ID NO 35
<211> LENGTH: 20
<212> TYPE: PRT
<213> ORGANISM: Homo sapiens

<400> SEQUENCE: 35

Trp Val Ser Asn Ile Asn Tyr Asp Gly Ser Ser Thr Tyr Tyr Ala Asp
1               5                   10                  15

Ser Val Lys Gly
            20
```

```
<210> SEQ ID NO 36
<211> LENGTH: 11
<212> TYPE: PRT
<213> ORGANISM: Homo sapiens

<400> SEQUENCE: 36

Ser Gly Asp Asn Ile Gly Ser Phe Tyr Val His
1               5                   10

<210> SEQ ID NO 37
<211> LENGTH: 14
<212> TYPE: PRT
<213> ORGANISM: Homo sapiens

<400> SEQUENCE: 37

Thr Gly Thr Ser Ser Asp Val Gly Asp Ile Asn Asp Val Ser
1               5                   10

<210> SEQ ID NO 38
<211> LENGTH: 14
<212> TYPE: PRT
<213> ORGANISM: Homo sapiens

<400> SEQUENCE: 38

Thr Gly Thr Ser Ser Asp Val Gly Asp Ile Asn Asp Val Ser
1               5                   10

<210> SEQ ID NO 39
<211> LENGTH: 14
<212> TYPE: PRT
<213> ORGANISM: Homo sapiens

<400> SEQUENCE: 39

Thr Gly Thr Ser Ser Asp Val Gly Asp Ile Asn Asp Val Ser
1               5                   10

<210> SEQ ID NO 40
<211> LENGTH: 14
<212> TYPE: PRT
<213> ORGANISM: Homo sapiens

<400> SEQUENCE: 40

Thr Gly Thr Ser Ser Asp Val Gly Asp Ile Asn Asp Val Ser
1               5                   10

<210> SEQ ID NO 41
<211> LENGTH: 14
<212> TYPE: PRT
<213> ORGANISM: Homo sapiens

<400> SEQUENCE: 41

Thr Gly Thr Ser Ser Asp Val Gly Asp Ile Asn Asp Val Ser
1               5                   10

<210> SEQ ID NO 42
<211> LENGTH: 14
<212> TYPE: PRT
<213> ORGANISM: Homo sapiens

<400> SEQUENCE: 42

Thr Gly Thr Ser Ser Asp Val Gly Asp Ile Asn Asp Val Ser
1               5                   10

<210> SEQ ID NO 43
<211> LENGTH: 14
<212> TYPE: PRT
```

<213> ORGANISM: Homo sapiens

<400> SEQUENCE: 43

Thr Gly Thr Ser Ser Asp Val Gly Asp Ile Asn Asp Val Ser
1               5                   10

<210> SEQ ID NO 44
<211> LENGTH: 14
<212> TYPE: PRT
<213> ORGANISM: Homo sapiens

<400> SEQUENCE: 44

Thr Gly Thr Ser Ser Asp Val Gly Asp Ile Asn Asp Val Ser
1               5                   10

<210> SEQ ID NO 45
<211> LENGTH: 11
<212> TYPE: PRT
<213> ORGANISM: Homo sapiens

<400> SEQUENCE: 45

Leu Val Ile Tyr Asp Asp Asn Asn Arg Pro Ser
1               5                   10

<210> SEQ ID NO 46
<211> LENGTH: 11
<212> TYPE: PRT
<213> ORGANISM: Homo sapiens

<400> SEQUENCE: 46

Leu Met Ile Tyr Asp Val Asn Asn Arg Pro Ser
1               5                   10

<210> SEQ ID NO 47
<211> LENGTH: 11
<212> TYPE: PRT
<213> ORGANISM: Homo sapiens

<400> SEQUENCE: 47

Leu Val Ile Tyr Asp Asp Asn Asn Arg Pro Ser
1               5                   10

<210> SEQ ID NO 48
<211> LENGTH: 11
<212> TYPE: PRT
<213> ORGANISM: Homo sapiens

<400> SEQUENCE: 48

Leu Met Ile Tyr Asp Val Asn Asn Arg Pro Ser
1               5                   10

<210> SEQ ID NO 49
<211> LENGTH: 11
<212> TYPE: PRT
<213> ORGANISM: Homo sapiens

<400> SEQUENCE: 49

Leu Met Ile Tyr Asp Val Asn Asn Arg Pro Ser
1               5                   10

<210> SEQ ID NO 50
<211> LENGTH: 11
<212> TYPE: PRT
<213> ORGANISM: Homo sapiens

<400> SEQUENCE: 50

-continued

```
Leu Met Ile Tyr Asp Val Asn Asn Arg Pro Ser
1               5                   10

<210> SEQ ID NO 51
<211> LENGTH: 11
<212> TYPE: PRT
<213> ORGANISM: Homo sapiens

<400> SEQUENCE: 51

Leu Met Ile Tyr Asp Val Asn Asn Arg Pro Ser
1               5                   10

<210> SEQ ID NO 52
<211> LENGTH: 11
<212> TYPE: PRT
<213> ORGANISM: Homo sapiens

<400> SEQUENCE: 52

Leu Met Ile Tyr Asp Val Asn Asn Arg Pro Ser
1               5                   10

<210> SEQ ID NO 53
<211> LENGTH: 11
<212> TYPE: PRT
<213> ORGANISM: Homo sapiens

<400> SEQUENCE: 53

Leu Met Ile Tyr Asp Val Asn Asn Arg Pro Ser
1               5                   10

<210> SEQ ID NO 54
<211> LENGTH: 11
<212> TYPE: PRT
<213> ORGANISM: Homo sapiens

<400> SEQUENCE: 54

Leu Met Ile Tyr Asp Val Asn Asn Arg Pro Ser
1               5                   10

<210> SEQ ID NO 55
<211> LENGTH: 11
<212> TYPE: PRT
<213> ORGANISM: Homo sapiens

<400> SEQUENCE: 55

Leu Met Ile Tyr Asp Val Asn Asn Arg Pro Ser
1               5                   10

<210> SEQ ID NO 56
<211> LENGTH: 10
<212> TYPE: PRT
<213> ORGANISM: Homo sapiens

<400> SEQUENCE: 56

Gly Ser Trp Ala Gly Ser Ser Gly Ser Tyr
1               5                   10

<210> SEQ ID NO 57
<211> LENGTH: 10
<212> TYPE: PRT
<213> ORGANISM: Homo sapiens

<400> SEQUENCE: 57

Ser Ser Tyr Gly Glu Ser Leu Thr Ser Tyr
1               5                   10
```

```
<210> SEQ ID NO 58
<211> LENGTH: 10
<212> TYPE: PRT
<213> ORGANISM: Homo sapiens

<400> SEQUENCE: 58

Ala Ser Trp Thr Gly Val Glu Pro Asp Tyr
1               5                   10

<210> SEQ ID NO 59
<211> LENGTH: 10
<212> TYPE: PRT
<213> ORGANISM: Homo sapiens

<400> SEQUENCE: 59

Gln Ser Tyr Ala Gly Ser Tyr Leu Ser Glu
1               5                   10

<210> SEQ ID NO 60
<211> LENGTH: 10
<212> TYPE: PRT
<213> ORGANISM: Homo sapiens

<400> SEQUENCE: 60

Ser Ser Tyr Gly Glu Ser Leu Thr Ser Tyr
1               5                   10

<210> SEQ ID NO 61
<211> LENGTH: 10
<212> TYPE: PRT
<213> ORGANISM: Homo sapiens

<400> SEQUENCE: 61

Ser Ser Tyr Gly Glu Ser Leu Thr Ser Tyr
1               5                   10

<210> SEQ ID NO 62
<211> LENGTH: 10
<212> TYPE: PRT
<213> ORGANISM: Homo sapiens

<400> SEQUENCE: 62

Ser Ser Tyr Gly Glu Ser Leu Thr Ser Tyr
1               5                   10

<210> SEQ ID NO 63
<211> LENGTH: 10
<212> TYPE: PRT
<213> ORGANISM: Homo sapiens

<400> SEQUENCE: 63

Ser Ser Tyr Gly Glu Ser Leu Thr Ser Tyr
1               5                   10

<210> SEQ ID NO 64
<211> LENGTH: 10
<212> TYPE: PRT
<213> ORGANISM: Homo sapiens

<400> SEQUENCE: 64

Ser Thr Tyr Asp Gly Pro Gly Leu Ser Glu
1               5                   10

<210> SEQ ID NO 65
```

```
<211> LENGTH: 10
<212> TYPE: PRT
<213> ORGANISM: Homo sapiens

<400> SEQUENCE: 65

Ser Ser Tyr Gly Glu Ser Leu Thr Ser Tyr
1               5                   10

<210> SEQ ID NO 66
<211> LENGTH: 10
<212> TYPE: PRT
<213> ORGANISM: Homo sapiens

<400> SEQUENCE: 66

Ser Ser Tyr Gly Glu Ser Leu Thr Ser Tyr
1               5                   10

<210> SEQ ID NO 67
<211> LENGTH: 124
<212> TYPE: PRT
<213> ORGANISM: Homo sapiens

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Phe Ile Ser Gly Asp Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Phe Met His Gly His Leu Gly Gly Leu Ser Met Asp
            100                 105                 110

Phe Trp Gly Gln Gly Thr Leu Val Thr Val Ser Ser
            115                 120

<210> SEQ ID NO 68
<211> LENGTH: 117
<212> TYPE: PRT
<213> ORGANISM: Homo sapiens

<400> SEQUENCE: 68

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110
```

```
Val Thr Val Ser Ser
        115

<210> SEQ ID NO 69
<211> LENGTH: 124
<212> TYPE: PRT
<213> ORGANISM: Homo sapiens

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Phe Ile Ser Gly Asp Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Phe Met His Gly His Leu Gly Gly Leu Ser Met Asp
            100                 105                 110

Phe Trp Gly Gln Gly Thr Leu Val Thr Val Ser Ser
            115                 120

<210> SEQ ID NO 70
<211> LENGTH: 117
<212> TYPE: PRT
<213> ORGANISM: Homo sapiens

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115

<210> SEQ ID NO 71
<211> LENGTH: 116
<212> TYPE: PRT
<213> ORGANISM: Homo sapiens

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
```

```
                    20                  25                  30
Trp Leu Ser Trp Val Arg Gln Ala Pro Gly Lys Gly Leu Glu Trp Val
            35                  40                  45
Ser Val Thr Gly Val His Gly Asp Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Thr Tyr Leu His Phe Asp Tyr Trp Gly Gln Gly Thr Leu Val
                100                 105                 110
Thr Val Ser Ser
        115

<210> SEQ ID NO 72
<211> LENGTH: 116
<212> TYPE: PRT
<213> ORGANISM: Homo sapiens

<400> SEQUENCE: 72

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Ser His
            20                  25                  30
Trp Leu Ser Trp Val Arg Gln Ala Pro Gly Lys Gly Leu Glu Trp Val
            35                  40                  45
Ser Val Ile Gly Asn Trp Gly Asp Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Thr Tyr Leu His Phe Asp Tyr Trp Gly Gln Gly Thr Leu Val
                100                 105                 110
Thr Val Ser Ser
        115

<210> SEQ ID NO 73
<211> LENGTH: 116
<212> TYPE: PRT
<213> ORGANISM: Homo sapiens

<400> SEQUENCE: 73

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg Ser His
            20                  25                  30
Trp Leu Ser Trp Val Arg Gln Ala Pro Gly Lys Gly Leu Glu Trp Val
            35                  40                  45
Ser Val Thr Thr His Gln Gly Tyr Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Thr Tyr Leu His Phe Asp Tyr Trp Gly Gln Gly Thr Leu Val
                100                 105                 110
```

Thr Val Ser Ser
        115

<210> SEQ ID NO 74
<211> LENGTH: 116
<212> TYPE: PRT
<213> ORGANISM: Homo sapiens

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Ala Thr Asn Arg Tyr Gly Tyr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Leu His Phe Asp Tyr Trp Gly Gln Gly Thr Leu Val
            100                 105                 110

Thr Val Ser Ser
        115

<210> SEQ ID NO 75
<211> LENGTH: 117
<212> TYPE: PRT
<213> ORGANISM: Homo sapiens

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115

<210> SEQ ID NO 76
<211> LENGTH: 116
<212> TYPE: PRT
<213> ORGANISM: Homo sapiens

<400> SEQUENCE: 76

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His

```
                    20                  25                  30
Trp Leu Ser Trp Val Arg Gln Ala Pro Gly Lys Gly Leu Glu Trp Val
                35                  40                  45
Ser Val Ile Thr Pro Tyr Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg Asp Thr Tyr Leu His Phe Asp Tyr Trp Gly Gln Gly Thr Leu Val
               100                 105                 110
Thr Val Ser Ser
            115

<210> SEQ ID NO 77
<211> LENGTH: 116
<212> TYPE: PRT
<213> ORGANISM: Homo sapiens

<400> SEQUENCE: 77

Gln Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Arg Ser His
                 20                  25                  30
Trp Leu Ser Trp Val Arg Gln Ala Pro Gly Lys Gly Leu Glu Trp Val
             35                  40                  45
Ser Val Ile Thr Pro Tyr Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg Asp Thr Tyr Leu His Phe Asp Tyr Trp Gly Gln Gly Thr Leu Val
               100                 105                 110
Thr Val Ser Ser
            115

<210> SEQ ID NO 78
<211> LENGTH: 110
<212> TYPE: PRT
<213> ORGANISM: Homo sapiens

<400> SEQUENCE: 78

Asp Ile Glu Leu Thr Gln Pro Pro Ser Val Ser Val Ala Pro Gly Gln
  1               5                  10                  15
Thr Ala Arg Ile Ser Cys Ser Gly Asp Asn Ile Gly Ser Phe Tyr Val
                 20                  25                  30
His Trp Tyr Gln Gln Lys Pro Gly Gln Ala Pro Val Leu Val Ile Tyr
             35                  40                  45
Asp Asp Asn Asn Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Gly Ser Trp Ala Gly Ser Ser Gly Ser
                85                  90                  95
Tyr Val Phe Gly Gly Arg Thr Lys Leu Thr Val Leu Gly Gln
               100                 105                 110
```

```
<210> SEQ ID NO 79
<211> LENGTH: 113
<212> TYPE: PRT
<213> ORGANISM: Homo sapiens

<400> SEQUENCE: 79

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln

<210> SEQ ID NO 80
<211> LENGTH: 110
<212> TYPE: PRT
<213> ORGANISM: Homo sapiens

<400> SEQUENCE: 80

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Thr Gly Val Glu Pro Asp
                85                  90                  95

Tyr Val Phe Gly Gly Gly Thr Lys Leu Thr Val Leu Gly Gln
            100                 105                 110

<210> SEQ ID NO 81
<211> LENGTH: 113
<212> TYPE: PRT
<213> ORGANISM: Homo sapiens

<400> SEQUENCE: 81

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Gly Ser
                85                  90                  95

Tyr Leu Ser Glu Val Phe Gly Gly Gly Thr Lys Leu Thr Val Leu Gly
                100                 105                 110

Gln

<210> SEQ ID NO 82
<211> LENGTH: 113
<212> TYPE: PRT
<213> ORGANISM: Homo sapiens

<400> SEQUENCE: 82

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
                20                  25                  30

Asn Asp Val Ser Trp Tyr Gln Gln His Pro Gly Lys Ala Pro Lys Leu
            35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
                100                 105                 110

Gln

<210> SEQ ID NO 83
<211> LENGTH: 113
<212> TYPE: PRT
<213> ORGANISM: Homo sapiens

<400> SEQUENCE: 83

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
                20                  25                  30

Asn Asp Val Ser Trp Tyr Gln Gln His Pro Gly Lys Ala Pro Lys Leu
            35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
                100                 105                 110

Gln

<210> SEQ ID NO 84
<211> LENGTH: 113
<212> TYPE: PRT
<213> ORGANISM: Homo sapiens

<400> SEQUENCE: 84

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln

<210> SEQ ID NO 85
<211> LENGTH: 113
<212> TYPE: PRT
<213> ORGANISM: Homo sapiens

<400> SEQUENCE: 85

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln

<210> SEQ ID NO 86
<211> LENGTH: 113
<212> TYPE: PRT
<213> ORGANISM: Homo sapiens

<400> SEQUENCE: 86

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Asp Gly Pro

```
                    85                  90                  95
Gly Leu Ser Glu Val Phe Gly Gly Thr Lys Leu Thr Val Leu Gly
            100                 105                 110
Gln
```

<210> SEQ ID NO 87
<211> LENGTH: 113
<212> TYPE: PRT
<213> ORGANISM: Homo sapiens

<400> SEQUENCE: 87

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln
```

<210> SEQ ID NO 88
<211> LENGTH: 113
<212> TYPE: PRT
<213> ORGANISM: Homo sapiens

<400> SEQUENCE: 88

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Asp Gly Pro
                85                  90                  95

Gly Leu Ser Glu Val Phe Gly Gly Gly Thr Lys Leu Thr Val Leu Gly
            100                 105                 110

Gln
```

<210> SEQ ID NO 89
<211> LENGTH: 372
<212> TYPE: DNA
<213> ORGANISM: Homo sapiens

<400> SEQUENCE: 89

```
caggtgcaat tggtggaaag cggcggcggc ctggtgcaac cgggcggcag cctgcgtctg      60
agctgcgcgg cctccggatt taccttttct tcttatgtta tgaattgggt gcgccaagcc    120
```

```
cctgggaagg gtctcgagtg ggtgagcttt atctctggtg attctagcaa tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtactttt    300
atgcatggtc atcttggtgg tggtcttttct atggattttt ggggccaagg caccctggtg    360
acggttagct ca                                                        372

<210> SEQ ID NO 90
<211> LENGTH: 351
<212> TYPE: DNA
<213> ORGANISM: Homo sapiens

<400> SEQUENCE: 90
caggtgcaat tggtggaaag cggcggcggc ctggtgcaac cgggcggcag cctgcgtctg     60
agctgcgcgg cctccggatt taccttcgt tctcattggc tttcttgggt gcgccaagcc    120
cctgggaagg gtctcgagtg ggtgagcaat atcaattatg atggtagctc tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtgatact    300
tatcttcatt ttgattattg gggccaaggc accctggtga cggttagctc a             351

<210> SEQ ID NO 91
<211> LENGTH: 372
<212> TYPE: DNA
<213> ORGANISM: Homo sapiens

<400> SEQUENCE: 91
caggtgcaat tggtggaaag cggcggcggc ctggtgcaac cgggcggcag cctgcgtctg     60
agctgcgcgg cctccggatt tacctttct tcttatgtta tgaattgggt gcgccaagcc    120
cctgggaagg gtctcgagtg ggtgagcttt atctctggtg attctagcaa tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtactttt    300
atgcatggtc atcttggtgg tggtcttttct atggattttt ggggccaagg caccctggtg    360
acggttagct ca                                                        372

<210> SEQ ID NO 92
<211> LENGTH: 351
<212> TYPE: DNA
<213> ORGANISM: Homo sapiens

<400> SEQUENCE: 92
caggtgcaat tggtggaaag cggcggcggc ctggtgcaac cgggcggcag cctgcgtctg     60
agctgcgcgg cctccggatt taccttcgt tctcattggc tttcttgggt gcgccaagcc    120
cctgggaagg gtctcgagtg ggtgagcaat atcaattatg atggtagctc tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtgatact    300
tatcttcatt ttgattattg gggccaaggc accctggtga cggttagctc a             351

<210> SEQ ID NO 93
<211> LENGTH: 348
<212> TYPE: DNA
<213> ORGANISM: Homo sapiens

<400> SEQUENCE: 93
```

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt actggtgttc atggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 94
<211> LENGTH: 348
<212> TYPE: DNA
<213> ORGANISM: Homo sapiens

<400> SEQUENCE: 94

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt attggtaatt ggggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 95
<211> LENGTH: 348
<212> TYPE: DNA
<213> ORGANISM: Homo sapiens

<400> SEQUENCE: 95

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt actactcatc agggttatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 96
<211> LENGTH: 348
<212> TYPE: DNA
<213> ORGANISM: Homo sapiens

<400> SEQUENCE: 96

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgct actaatcgtt atggttatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 97
<211> LENGTH: 351
<212> TYPE: DNA
<213> ORGANISM: Homo sapiens

<400> SEQUENCE: 97

```
caggtgcaat tggtggaaag cggcggcggc ctggtgcaac cgggcggcag cctgcgtctg    60
agctgcgcgg cctccggatt tacctttcgt tctcattggc tttcttgggt gcgccaagcc   120
cctgggaagg gtctcgagtg ggtgagcaat atcaattatg atggtagctc tacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtgatact   300
tatcttcatt ttgattattg gggccaaggc accctggtga cggttagctc a            351
```

<210> SEQ ID NO 98
<211> LENGTH: 348
<212> TYPE: DNA
<213> ORGANISM: Homo sapiens

<400> SEQUENCE: 98

```
caggtgcaat tggtggaaag cggcggcggc ctggtgcaac cgggcggcag cctgcgtctg    60
agctgcgcgg cctccggatt tacctttcgt tctcattggc tttcttgggt gcgccaagcc   120
cctgggaagg gtctcgagtg ggtgagcgtt attactcctt atggtgatac ttattatgct   180
gattctgtta agggtcgttt taccatttca cgtgataatt cgaaaaacac cctgtatctg   240
caaatgaaca gcctgcgtgc ggaagatacg gccgtgtatt attgcgcgcg tgatacttat   300
cttcattttg attattgggg ccaaggcacc ctggtgacgg ttagctca                348
```

<210> SEQ ID NO 99
<211> LENGTH: 348
<212> TYPE: DNA
<213> ORGANISM: Homo sapiens

<400> SEQUENCE: 99

```
caggtgcaat tggtggaaag cggcggcggc ctggtgcaac cgggcggcag cctgcgtctg    60
agctgcgcgg cctccggatt tacctttcgt tctcattggc tttcttgggt gcgccaagcc   120
cctgggaagg gtctcgagtg ggtgagcgtt attactcctt atggtgatac ttattatgct   180
gattctgtta agggtcgttt taccatttca cgtgataatt cgaaaaacac cctgtatctg   240
caaatgaaca gcctgcgtgc ggaagatacg gccgtgtatt attgcgcgcg tgatacttat   300
cttcattttg attattgggg ccaaggcacc ctggtgacgg ttagctca                348
```

<210> SEQ ID NO 100
<211> LENGTH: 330
<212> TYPE: DNA
<213> ORGANISM: Homo sapiens

<400> SEQUENCE: 100

```
gatatcgaac tgacccagcc gccttcagtg agcgttgcac aggtcagact cgcgcgtatc    60
tcgtgtagcg gcgataatat tggttctttt tatgttcatt ggtaccagca gaaacccggg   120
caggcgccag ttcttgtgat ttatgatgat aataatcgtc cctcaggcat cccggaacgc   180
tttagcggat ccaacagcgg caacaccgcg accctgacca ttagcggcac tcaggcggaa   240
gacgaagcgg attattattg cggttcttgg gctggttctt ctggttctta tgtgtttggc   300
ggccgcacga agttaaccgt tcttggccag                                   330
```

<210> SEQ ID NO 101
<211> LENGTH: 339
<212> TYPE: DNA
<213> ORGANISM: Homo sapiens

<400> SEQUENCE: 101

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339
```

<210> SEQ ID NO 102
<211> LENGTH: 330
<212> TYPE: DNA
<213> ORGANISM: Homo sapiens

<400> SEQUENCE: 102

```
gatatcgaac tgacccagcc gccttcagtg agcgttgcac caggtcagac cgcgcgtatc    60
tcgtgtagcg gcgataatat tggttctttt tatgttcatt ggtaccagca gaaacccggg   120
caggcgccag ttcttgtgat ttatgatgat aataatcgtc cctcaggcat cccggaacgc   180
tttagcggat ccaacagcgg caacaccgcg accctgacca ttagcggcac tcaggcggaa   240
gacgaagcgg attattattg cgcttcttgg actggtgttg agcctgatta tgtgtttggc   300
ggcggcacga agttaaccgt tcttggccag                                    330
```

<210> SEQ ID NO 103
<211> LENGTH: 339
<212> TYPE: DNA
<213> ORGANISM: Homo sapiens

<400> SEQUENCE: 103

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc cagtcttatg ctggttctta tctttctgag   300
gtgtttggcg gcggcacgaa gttaaccgtt cttggccag                          339
```

<210> SEQ ID NO 104
<211> LENGTH: 339
<212> TYPE: DNA
<213> ORGANISM: Homo sapiens

<400> SEQUENCE: 104

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339
```

<210> SEQ ID NO 105
<211> LENGTH: 339
<212> TYPE: DNA
<213> ORGANISM: Homo sapiens

<400> SEQUENCE: 105

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339

<210> SEQ ID NO 106
<211> LENGTH: 339
<212> TYPE: DNA
<213> ORGANISM: Homo sapiens

<400> SEQUENCE: 106
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339

<210> SEQ ID NO 107
<211> LENGTH: 339
<212> TYPE: DNA
<213> ORGANISM: Homo sapiens

<400> SEQUENCE: 107
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339

<210> SEQ ID NO 108
<211> LENGTH: 339
<212> TYPE: DNA
<213> ORGANISM: Homo sapiens

<400> SEQUENCE: 108
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tctacttatg atggtcctgg tctttctgag   300
gtgtttggcg gcggcacgaa gttaaccgtt cttggccag                          339

<210> SEQ ID NO 109
<211> LENGTH: 339
<212> TYPE: DNA
<213> ORGANISM: Homo sapiens

<400> SEQUENCE: 109
```

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339
```

<210> SEQ ID NO 110
<211> LENGTH: 339
<212> TYPE: DNA
<213> ORGANISM: Homo sapiens

<400> SEQUENCE: 110

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tctacttatg atggtcctgg tctttctgag   300
gtgtttggcg gcggcacgaa gttaaccgtt cttggccag                          339
```

<210> SEQ ID NO 111
<211> LENGTH: 469
<212> TYPE: PRT
<213> ORGANISM: Homo sapiens

<400> SEQUENCE: 111

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 112
<211> LENGTH: 462
<212> TYPE: PRT
<213> ORGANISM: Homo sapiens

<400> SEQUENCE: 112

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

Tyr Tyr Cys Ala Arg Asp Thr Tyr Leu His Phe Asp Tyr Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 113
<211> LENGTH: 469
<212> TYPE: PRT
<213> ORGANISM: Homo sapiens

<400> SEQUENCE: 113

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

-continued

```
Pro Gly Gly Ser Leu Arg Leu Ser Cys Ala Ala Ser Gly Phe Thr Phe
            35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460
```

```
Leu Ser Pro Gly Lys
465

<210> SEQ ID NO 114
<211> LENGTH: 462
<212> TYPE: PRT
<213> ORGANISM: Homo sapiens

<400> SEQUENCE: 114

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Leu His Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365
```

```
Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460

<210> SEQ ID NO 115
<211> LENGTH: 461
<212> TYPE: PRT
<213> ORGANISM: Homo sapiens

<400> SEQUENCE: 115

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Lys Gly Leu
    50                  55                  60

Glu Trp Val Ser Val Thr Gly Val His Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285
```

Phe Asn Trp Tyr Val Asp Gly Val Glu Val His Asn Ala Lys Thr Lys
            290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460

<210> SEQ ID NO 116
<211> LENGTH: 461
<212> TYPE: PRT
<213> ORGANISM: Homo sapiens

<400> SEQUENCE: 116

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Ile Gly Asn Trp Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Gln
            275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
                340                 345                 350

Thr Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
    450                 455                 460

<210> SEQ ID NO 117
<211> LENGTH: 461
<212> TYPE: PRT
<213> ORGANISM: Homo sapiens

<400> SEQUENCE: 117

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Thr Thr His Gln Gly Tyr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

-continued

```
Thr Leu Val Thr Val Ser Ser Ala Ser Thr Lys Gly Pro Ser Val Phe
            130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 118
<211> LENGTH: 465
<212> TYPE: PRT
<213> ORGANISM: Homo sapiens

<400> SEQUENCE: 118

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45
```

```
Arg Ser His Trp Leu Ser Trp Val Arg Gln Ala Pro Gly Lys Gly Leu
    50                  55                  60

Glu Trp Val Ser Ala Thr Asn Arg Tyr Gly Tyr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Ile Val Thr Cys Val Val Asp Val Ser Glu Asp Asp
        275                 280                 285

Pro Asp Val Gln Ile Ser Trp Phe Val Asn Asn Val Glu Val His Thr
    290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Lys Asp Leu Pro Ala Pro Ile Glu Arg
            340                 345                 350

Thr Ile Ser Lys Pro Lys Gly Ser Val Arg Ala Pro Gln Val Tyr Val
        355                 360                 365

Leu Pro Pro Pro Glu Glu Glu Met Thr Lys Lys Gln Val Thr Leu Thr
    370                 375                 380

Cys Met Val Thr Asp Phe Met Pro Glu Asp Ile Tyr Val Glu Trp Thr
385                 390                 395                 400

Asn Asn Gly Lys Thr Glu Leu Asn Tyr Lys Asn Thr Glu Pro Val Leu
                405                 410                 415

Asp Ser Asp Gly Ser Tyr Phe Met Tyr Ser Lys Leu Arg Val Glu Lys
            420                 425                 430

Lys Asn Trp Val Glu Arg Asn Ser Tyr Ser Cys Ser Val Val His Glu
        435                 440                 445

Gly Leu His Asn His His Thr Thr Lys Ser Phe Ser Arg Thr Pro Gly
    450                 455                 460

Lys
```

```
<210> SEQ ID NO 119
<211> LENGTH: 462
<212> TYPE: PRT
<213> ORGANISM: Homo sapiens

<400> SEQUENCE: 119
```

| | | | | | | | | | | | | | | |
|---|---|---|---|---|---|---|---|---|---|---|---|---|---|---|
|Met|Ala|Trp|Val|Trp|Thr|Leu|Pro|Phe|Leu|Met|Ala|Ala|Ala|Gln|Ser|
|1| | |5| | | | |10| | | | |15| |
|Val|Gln|Ala|Gln|Val|Gln|Leu|Val|Glu|Ser|Gly|Gly|Gly|Leu|Val|Gln|
| | | |20| | | | |25| | | | |30| | |
|Pro|Gly|Gly|Ser|Leu|Arg|Leu|Ser|Cys|Ala|Ala|Ser|Gly|Phe|Thr|Phe|
| | | |35| | | | |40| | | | |45| | |
|Arg|Ser|His|Trp|Leu|Ser|Trp|Val|Arg|Gln|Ala|Pro|Gly|Lys|Gly|Leu|
| |50| | | | |55| | | | |60| | | | |
|Glu|Trp|Val|Ser|Asn|Ile|Asn|Tyr|Asp|Gly|Ser|Ser|Thr|Tyr|Tyr|Ala|
|65| | | | |70| | | | |75| | | | |80|
|Asp|Ser|Val|Lys|Gly|Arg|Phe|Thr|Ile|Ser|Arg|Asp|Asn|Ser|Lys|Asn|
| | | | |85| | | | |90| | | | |95| |
|Thr|Leu|Tyr|Leu|Gln|Met|Asn|Ser|Leu|Arg|Ala|Glu|Asp|Thr|Ala|Val|
| | | |100| | | | |105| | | | |110| | |
|Tyr|Tyr|Cys|Ala|Arg|Asp|Thr|Tyr|Leu|His|Phe|Asp|Tyr|Trp|Gly|Gln|
| | | |115| | | | |120| | | | |125| | |
|Gly|Thr|Leu|Val|Thr|Val|Ser|Ser|Ala|Ser|Thr|Lys|Gly|Pro|Ser|Val|
| | | |130| | | | |135| | | | |140| | |
|Phe|Pro|Leu|Ala|Pro|Cys|Ser|Arg|Ser|Thr|Ser|Glu|Ser|Thr|Ala|Ala|
|145| | | | |150| | | | |155| | | | |160|
|Leu|Gly|Cys|Leu|Val|Lys|Asp|Tyr|Phe|Pro|Glu|Pro|Val|Thr|Val|Ser|
| | | | |165| | | | |170| | | | |175| |
|Trp|Asn|Ser|Gly|Ala|Leu|Thr|Ser|Gly|Val|His|Thr|Phe|Pro|Ala|Val|
| | | |180| | | | |185| | | | |190| | |
|Leu|Gln|Ser|Ser|Gly|Leu|Tyr|Ser|Leu|Ser|Ser|Val|Val|Thr|Val|Pro|
| | | |195| | | | |200| | | | |205| | |
|Ser|Ser|Asn|Phe|Gly|Thr|Gln|Thr|Tyr|Thr|Cys|Asn|Val|Asp|His|Lys|
| |210| | | | |215| | | | |220| | | | |
|Pro|Ser|Asn|Thr|Lys|Val|Asp|Lys|Thr|Val|Glu|Arg|Lys|Cys|Cys|Val|
|225| | | | |230| | | | |235| | | | |240|
|Glu|Cys|Pro|Pro|Cys|Pro|Ala|Pro|Pro|Val|Ala|Gly|Pro|Ser|Val|Phe|
| | | |245| | | | |250| | | | |255| | |
|Leu|Phe|Pro|Pro|Lys|Pro|Lys|Asp|Thr|Leu|Met|Ile|Ser|Arg|Thr|Pro|
| | | |260| | | | |265| | | | |270| | |
|Glu|Val|Thr|Cys|Val|Val|Val|Asp|Val|Ser|His|Glu|Asp|Pro|Glu|Val|
| | | |275| | | | |280| | | | |285| | |
|Gln|Phe|Asn|Trp|Tyr|Val|Asp|Gly|Val|Glu|Val|His|Asn|Ala|Lys|Thr|
| |290| | | | |295| | | | |300| | | | |
|Lys|Pro|Arg|Glu|Glu|Gln|Phe|Asn|Ser|Thr|Phe|Arg|Val|Val|Ser|Val|
|305| | | | |310| | | | |315| | | | |320|
|Leu|Thr|Val|Val|His|Gln|Asp|Trp|Leu|Asn|Gly|Lys|Glu|Tyr|Lys|Cys|
| | | | |325| | | | |330| | | | |335| |
|Lys|Val|Ser|Asn|Lys|Gly|Leu|Pro|Ala|Pro|Ile|Glu|Lys|Thr|Ile|Ser|
| | | |340| | | | |345| | | | |350| | |
|Lys|Thr|Lys|Gly|Gln|Pro|Arg|Glu|Pro|Gln|Val|Tyr|Thr|Leu|Pro|Pro|
| | | |355| | | | |360| | | | |365| | |
|Ser|Arg|Glu|Glu|Met|Thr|Lys|Asn|Gln|Val|Ser|Leu|Thr|Cys|Leu|Val|

```
               370                 375                 380
Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 120
<211> LENGTH: 461
<212> TYPE: PRT
<213> ORGANISM: Homo sapiens

<400> SEQUENCE: 120

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Ile Thr Pro Tyr Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
```

```
                    290                 295                 300
Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
                340                 345                 350

Thr Lys Gly Gln Pro Arg Glu Pro Gln Val Tyr Thr Leu Pro Pro Ser
                355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
450                 455                 460

<210> SEQ ID NO 121
<211> LENGTH: 461
<212> TYPE: PRT
<213> ORGANISM: Homo sapiens

<400> SEQUENCE: 121

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Arg Ser His Trp Leu Ser Trp Val Arg Gln Ala Pro Gly Lys Gly Leu
50                  55                  60

Glu Trp Val Ser Val Ile Thr Pro Tyr Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
                100                 105                 110

Tyr Cys Ala Arg Asp Thr Tyr Leu His Phe Asp Tyr Trp Gly Gln Gly
            115                 120                 125

Thr Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
```

```
                210                 215                 220
Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Gln
                275                 280                 285

Phe Asn Trp Tyr Val Asp Gly Val Glu Val His Asn Ala Lys Thr Lys
                290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
                340                 345                 350

Thr Lys Gly Gln Pro Arg Glu Pro Gln Val Tyr Thr Leu Pro Pro Ser
                355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
                450                 455                 460

<210> SEQ ID NO 122
<211> LENGTH: 130
<212> TYPE: PRT
<213> ORGANISM: Homo sapiens

<400> SEQUENCE: 122

Met Ser Val Leu Thr Gln Val Leu Ala Leu Leu Leu Trp Leu Thr
1               5                   10                  15

Gly Thr Arg Cys Asp Ile Glu Leu Thr Gln Pro Pro Ser Val Ser Val
                20                  25                  30

Ala Pro Gly Gln Thr Ala Arg Ile Ser Cys Ser Gly Asp Asn Ile Gly
                35                  40                  45

Ser Phe Tyr Val His Trp Tyr Gln Gln Lys Pro Gly Gln Ala Pro Val
                50                  55                  60

Leu Val Ile Tyr Asp Asp Asn Asn Arg Pro Ser Gly Ile Pro Glu Arg
65                  70                  75                  80

Phe Ser Gly Ser Asn Ser Gly Asn Thr Ala Thr Leu Thr Ile Ser Gly
                85                  90                  95

Thr Gln Ala Glu Asp Glu Ala Asp Tyr Tyr Cys Gly Ser Trp Ala Gly
                100                 105                 110

Ser Ser Gly Ser Tyr Val Phe Gly Gly Arg Thr Lys Leu Thr Val Leu
                115                 120                 125

Gly Gln
```

<210> SEQ ID NO 123
<211> LENGTH: 237
<212> TYPE: PRT
<213> ORGANISM: Homo sapiens

<400> SEQUENCE: 123

```
Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser
                20                  25                  30

Gly Ser Pro Gly Gln Ser Ile Thr Ile Ser Cys Thr Gly Thr Ser
            35                  40                  45

Ser Asp Val Gly Asp Ile Asn Asp Val Ser Trp Tyr Gln His Pro
        50                  55                  60

Gly Lys Ala Pro Lys Leu Met Ile Tyr Asp Val Asn Asn Arg Pro
65                  70                  75                  80

Ser Gly Val Ser Asn Arg Phe Ser Gly Ser Lys Ser Gly Asn Thr
                85                  90                  95

Ala Ser Leu Thr Ile Ser Gly Leu Gln Ala Glu Asp Glu Ala Asp
            100                 105                 110

Tyr Tyr Cys Ser Ser Tyr Gly Glu Ser Leu Thr Ser Tyr Val Phe
        115                 120

Gly Gly Gly Thr Lys Leu Thr Val Leu Gly Gln Pro Lys Ala Ala
            125                 130                 135

Pro Ser Val Thr Leu Phe Pro Pro Ser Ser Glu Glu Leu Gln Ala
                140                 145                 150

Asn Lys Ala Thr Leu Val Cys Leu Ile Ser Asp Phe Tyr Pro Gly
            155                 160                 165

Ala Val Thr Val Ala Trp Lys Ala Asp Ser Ser Pro Val Lys Ala
        170                 175                 180

Gly Val Glu Thr Thr Thr Pro Ser Lys Gln Ser Asn Asn Lys Tyr
                185                 190                 195

Ala Ala Ser Ser Tyr Leu Ser Leu Thr Pro Glu Gln Trp Lys Ser
            200                 205                 210

His Arg Ser Tyr Ser Cys Gln Val Thr His Glu Gly Ser Thr Val
        215                 220                 225

Glu Lys Thr Val Ala Pro Thr Glu Cys Ser
                230                 235
```

<210> SEQ ID NO 124
<211> LENGTH: 234
<212> TYPE: PRT
<213> ORGANISM: Homo sapiens

<400> SEQUENCE: 124

```
Met Ser Val Leu Thr Gln Val Leu Ala Leu Leu Leu Trp Leu Thr
1               5                   10                  15

Gly Thr Arg Cys Asp Ile Glu Leu Thr Gln Pro Pro Ser Val Ser
                20                  25                  30

Val Ala Pro Gly Gln Thr Ala Arg Ile Ser Cys Ser Gly Asp Asn
            35                  40                  45

Ile Gly Ser Phe Tyr Val His Trp Tyr Gln Gln Lys Pro Gly Gln
        50                  55                  60

Ala Pro Val Leu Val Ile Tyr Asp Asp Asn Asn Arg Pro Ser Gly
65                  70                  75                  80

Ile Pro Glu Arg Phe Ser Gly Ser Asn Ser Gly Asn Thr Ala Thr
                85                  90                  95

Leu Thr Ile Ser Gly
```

```
Thr Gln Ala Glu Asp Glu Ala Asp Tyr Tyr Cys Ala Ser Trp Thr Gly
            100                 105                 110

Val Glu Pro Asp Tyr Val Phe Gly Gly Gly Thr Lys Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230

<210> SEQ ID NO 125
<211> LENGTH: 237
<212> TYPE: PRT
<213> ORGANISM: Homo sapiens

<400> SEQUENCE: 125

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Gln Ser
            100                 105                 110

Tyr Ala Gly Ser Tyr Leu Ser Glu Val Phe Gly Gly Gly Thr Lys Leu
            115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
            210                 215                 220

Ser Thr Val Glu Lys Thr Val Ala Pro Thr Glu Cys Ser
225                 230                 235
```

<210> SEQ ID NO 126
<211> LENGTH: 237
<212> TYPE: PRT
<213> ORGANISM: Homo sapiens

<400> SEQUENCE: 126

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Gly Thr Lys Leu
        115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 127
<211> LENGTH: 237
<212> TYPE: PRT
<213> ORGANISM: Homo sapiens

<400> SEQUENCE: 127

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

```
Ile Ser Gly Leu Gln Ala Glu Asp Glu Ala Asp Tyr Tyr Cys Ser Ser
                100                 105                 110

Tyr Gly Glu Ser Leu Thr Ser Tyr Val Phe Gly Gly Thr Lys Leu
            115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
            210                 215                 220

Ser Thr Val Glu Lys Thr Val Ala Pro Thr Glu Cys Ser
225                 230                 235

<210> SEQ ID NO 128
<211> LENGTH: 237
<212> TYPE: PRT
<213> ORGANISM: Homo sapiens

<400> SEQUENCE: 128

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
                20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
                100                 105                 110

Tyr Gly Glu Ser Leu Thr Ser Tyr Val Phe Gly Gly Thr Lys Leu
            115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
            210                 215                 220

Ser Thr Val Glu Lys Thr Val Ala Pro Thr Glu Cys Ser
225                 230                 235
```

<210> SEQ ID NO 129
<211> LENGTH: 237
<212> TYPE: PRT
<213> ORGANISM: Homo sapiens

<400> SEQUENCE: 129

```
Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
50                      55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Gly Thr Lys Leu
            115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
210                 215                 220

Ser Thr Val Glu Lys Thr Val Ala Pro Thr Glu Cys Ser
225                 230                 235
```

<210> SEQ ID NO 130
<211> LENGTH: 237
<212> TYPE: PRT
<213> ORGANISM: Homo sapiens

<400> SEQUENCE: 130

```
Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
50                      55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Thr
```

```
                   100                 105                 110
Tyr Asp Gly Pro Gly Leu Ser Glu Val Phe Gly Gly Thr Lys Leu
            115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
            165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
            210                 215                 220

Ser Thr Val Glu Lys Thr Val Ala Pro Thr Glu Cys Ser
225                 230                 235

<210> SEQ ID NO 131
<211> LENGTH: 237
<212> TYPE: PRT
<213> ORGANISM: Homo sapiens

<400> SEQUENCE: 131

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
        50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Thr Lys Leu
            115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
            165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
            210                 215                 220

Ser Thr Val Glu Lys Thr Val Ala Pro Thr Glu Cys Ser
225                 230                 235
```

```
<210> SEQ ID NO 132
<211> LENGTH: 237
<212> TYPE: PRT
<213> ORGANISM: Homo sapiens

<400> SEQUENCE: 132

Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Thr
            100                 105                 110

Tyr Asp Gly Pro Gly Leu Ser Glu Val Phe Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 133
<211> LENGTH: 1410
<212> TYPE: DNA
<213> ORGANISM: Homo sapiens

<400> SEQUENCE: 133
atggcttggg tgtggacctt gccattcctg atggcagctg cccaaagcgt gcaggcccag    60
gtgcagctgg tcgagtctgg cggcggactg gtgcagcctg gcggcagcct gagactgagc   120
tgcgccgcca gcggcttcac cttcagcagc tacgtgatga actgggtgcg gcaggccct   180 ggcaagggcc tggagtgggt gtccttcatc agcggcgaca gcagcaacac ctactacgcc   240
gacagcgtga aggccggtt caccatcagc cggacaacaa gcaagaacac cctgtacctg   300
cagatgaaca gcctgcgggc cgaggacacc gccgtgtact actgcgcccg gaccttcatg   360 cacgccacc tggcggagg actgagcatg gatttctggg ccagggcac cctggtcacc   420 gtctcctcag cttccaccaa gggcccatcc gtcttccccc tggcgccctg ctccaggagc   480
acctccgaga gcacagcggc cctgggctgc ctggtcaagg actacttccc cgaaccggtg   540
acggtgtcgt ggaactcagg cgctctgacc agcggcgtgc acaccttccc agctgtccta   600
```

| | |
|---|---|
| cagtcctcag gactctactc cctcagcagc gtggtgacag tgccctccag caacttcggc | 660 |
| acccagacct acacctgcaa cgtagatcac aagcccagca acaccaaggt ggacaagaca | 720 |
| gttgagcgca aatgttgtgt cgagtgccca ccgtgcccag caccacctgt ggcaggaccg | 780 |
| tcagtcttcc tcttcccccc aaaacccaag gacaccctca tgatctcccg gacccctgag | 840 |
| gtcacgtgcg tggtggtgga cgtgagccac gaagacccccg aggtccagtt caactggtac | 900 |
| gtggacggcg tggaggtgca taatgccaag acaaagccac gggaggagca gttcaacagc | 960 |
| acgttccgtg tggtcagcgt cctcaccgtt gtgcaccagg actggctgaa cggcaaggag | 1020 |
| tacaagtgca aggtctccaa caaaggcctc ccagccccca tcgagaaaac catctccaaa | 1080 |
| accaaagggc agccccgaga accacaggtg tacaccctgc ccccatcccg ggaggagatg | 1140 |
| accaagaacc aggtcagcct gacctgcctg gtcaaaggct tctaccccag cgacatcgcc | 1200 |
| gtggagtggg agagcaatgg gcagccggag aacaactaca agaccacacc tcccatgctg | 1260 |
| gactccgacg gctccttctt cctctacagc aagctcaccg tggacaagag caggtggcag | 1320 |
| caggggaacg tcttctcatg ctccgtgatg catgaggctc tgcacaacca ctacacgcag | 1380 |
| aagagcctct ccctgtctcc gggtaaatga | 1410 |

<210> SEQ ID NO 134
<211> LENGTH: 1389
<212> TYPE: DNA
<213> ORGANISM: Homo sapiens

<400> SEQUENCE: 134

| | |
|---|---|
| atggcttggg tgtggacctt gccattcctg atggcagctg cccaaggtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggcccct | 180 |
| ggcaagggcc tggaatgggt gtccaacatc aactacgacg gcagcagcac ctactacgcc | 240 |
| gacagcgtga agggccggtt caccatcagc cgggacaaca gcaagaacac cctgtacctg | 300 |
| cagatgaaca gcctgcgggc cgaggacacc gccgtgtact actgcgccag ggacacctac | 360 |
| ctgcacttcg actactgggg ccagggcacc ctggtcaccg tctcctcagc ttccaccaag | 420 |
| ggcccatccg tcttccccct ggcgccctgc tccaggagca cctccgagag cacagcggcc | 480 |
| ctgggctgcc tggtcaagga ctacttcccc gaaccggtga cggtgtcgtg gaactcaggc | 540 |
| gctctgacca gcggcgtgca caccttccca gctgtcctac agtcctcagg actctactcc | 600 |
| ctcagcagcg tggtgacagt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg caggaccgt cagtcttcct cttcccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg ggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga acaactacaa gaccacacct cccatgctgg actccgacgg ctccttcttc | 1260 |
| ctctacagca agctcaccgt ggacaagagc aggtggcagc aggggaacgt cttctcatgc | 1320 |

```
tccgtgatgc atgaggctct gcacaaccac tacacgcaga agagcctctc cctgtctccg   1380
ggtaaatga                                                           1389

<210> SEQ ID NO 135
<211> LENGTH: 1410
<212> TYPE: DNA
<213> ORGANISM: Homo sapiens

<400> SEQUENCE: 135
atggcttggg tgtggacctt gccattcctg atggcagctg cccaaagcgt gcaggcccag     60
gtgcagctgg tcgagtctgg cggcggactg gtgcagcctg gcggcagcct gagactgagc    120
tgcgccgcca gcggcttcac cttcagcagc tacgtgatga actgggtgcg gcaggcccct    180
ggcaagggcc tggagtgggt gtccttcatc agcggcgaca gcagcaacac ctactacgcc    240
gacagcgtga agggccggtt caccatcagc cgggacaaca gcaagaacac cctgtacctg    300
cagatgaaca gcctgcgggc cgaggacacc gccgtgtact actgcgcccg gaccttcatg    360
cacggccacc tgggcggagg actgagcatg gatttctggg gccagggcac cctggtcacc    420
gtctcctcag cttccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agctgtccta    600
cagtcctcag gactctactc cctcagcagc gtggtgacag tgccctccag caacttcggc    660
acccagacct acacctgcaa cgtagatcac aagcccagca caccaaggt ggacaagaca    720 gttgagcgca aatgttgtgt cgagtgccca ccgtgcccag caccacctgt ggcaggaccg    780
tcagtcttcc tcttcccccc aaaacccaag gacaccctca tgatctcccg gacccctgag    840
gtcacgtgcg tggtggtgga cgtgagccac gaagaccccg aggtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagccccca tcgagaaaac catctccaaa   1080
accaaagggc agccccgaga accacaggtg tacaccctgc ccccatcccg ggaggagatg   1140
accaagaacc aggtcagcct gacctgcctg gtcaaaggct tctaccccag cgacatcgcc   1200
gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                    1410

<210> SEQ ID NO 136
<211> LENGTH: 1389
<212> TYPE: DNA
<213> ORGANISM: Homo sapiens

<400> SEQUENCE: 136
atggcttggg tgtggacctt gccattcctg atggcagctg cccaaggtgt ccaggcccag     60
gtgcagctgg tcgagagcgg cggagggctg gtgcagcctg gcggcagcct gagactgagc    120
tgcgccgcca gcggcttcac cttcagaagc cactggctgt cctgggtgcg gcaggcccct    180
ggcaagggcc tggaatgggt gtccaacatc aactacgacg gcagcagcac ctactacgcc    240
gacagcgtga agggccggtt caccatcagc cgggacaaca gcaagaacac cctgtacctg    300
cagatgaaca gcctgcgggc cgaggacacc gccgtgtact actgcgccag ggacaccta   360
```

| | |
|---|---|
| ctgcacttcg actactgggg ccagggcacc ctggtcaccg tctcctcagc ttccaccaag | 420 |
| ggcccatccg tcttcccct ggcgccctgc tccaggagca cctccgagag cacagcggcc | 480 |
| ctgggctgcc tggtcaagga ctacttcccc gaaccggtga cggtgtcgtg aactcaggc | 540 |
| gctctgacca gcggcgtgca caccttccca gctgtcctac agtcctcagg actctactcc | 600 |
| ctcagcagcg tggtgacagt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg gcaggaccgt cagtcttcct cttccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg ggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga acaactacaa gaccacacct cccatgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 137
<211> LENGTH: 1386
<212> TYPE: DNA
<213> ORGANISM: Homo sapiens

<400> SEQUENCE: 137

| | |
|---|---|
| atggcttggg tgtggaccct tgccattcct g atggcagctg cccaaagtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggccct | 180 |
| ggcaagggcc tggaatgggt gtccgtgacc ggcgtgcacg gcgacaccta ctacgccgac | 240 |
| agcgtgaagg gccggttcac catcagccgg gacaacagca gaacaccct gtacctgcag | 300 |
| atgaacagcc tgcgggccga ggacaccgcc gtgtactact gcgccaggga cacctacctg | 360 |
| cacttcgact actggggcca gggcaccctg gtcaccgtct cctcagcttc caccaagggc | 420 |
| ccatccgtct tccccctggc gccctgctcc aggagcacct ccgagagcac agcggccctg | 480 |
| ggctgcctgt caaggactac cttccccgaa ccggtgacgg tgtcgtggaa ctcaggcgct | 540 |
| ctgaccagcg gcgtgcacac cttcccagct gtcctacagt cctcaggact ctactcctc | 600 |
| agcagcgtgt gacagtgcc ctccagcaac ttcggcaccc agacctacac ctgcaacgta | 660 |
| gatcacaagc ccagcaacac caaggtggac aagacagttg agcgcaaatg ttgtgtcgag | 720 |
| tgcccaccgt gcccagcacc acctgtgca ggaccgtcag tcttcctctt ccccccaaaa | 780 |
| cccaaggaca ccctcatgat ctcccggacc cctgaggtca cgtgcgtggt ggtggacgtg | 840 |
| agccacgaag accccgaggt ccagttcaac tggtacgtgg acggcgtgga ggtgcataat | 900 |
| gccaagacaa agccacggga ggagcagttc aacagcacgt tccgtgtggt cagcgtcctc | 960 |
| accgttgtgc accaggactg gctgaacggc aaggagtaca agtgcaaggt ctccaacaaa | 1020 |
| ggcctcccag cccccatcga gaaaaccatc tccaaaacca agggcagcc ccgagaacca | 1080 |

| | |
|---|---|
| caggtgtaca ccctgcccc atcccgggag gagatgacca agaaccaggt cagcctgacc | 1140 |
| tgcctggtca aaggcttcta ccccagcgac atcgccgtgg agtgggagag caatgggcag | 1200 |
| ccggagaaca actacaagac cacacctccc atgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatga | 1386 |

<210> SEQ ID NO 138
<211> LENGTH: 1386
<212> TYPE: DNA
<213> ORGANISM: Homo sapiens

<400> SEQUENCE: 138

| | |
|---|---|
| atggcttggg tgtggacctt gccattcctg atggcagctg cccaaagtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggcccct | 180 |
| ggcaagggcc tggaatgggt gtccgtgatc ggcaactggg gcgacaccta ctacgccgac | 240 |
| agcgtgaagg gccggttcac catcagccgg gacaacagca gaaacaccct gtacctgcag | 300 |
| atgaacagcc tgcgggccga ggacaccgcc gtgtactact gcgccaggga cacctacctg | 360 |
| cacttcgact actggggcca gggcacccty gtcaccgtct cctcagcttc caccaagggc | 420 |
| ccatccgtct tccccctggc gccctgctcc aggagcacct ccgagagcac agcggccctg | 480 |
| ggctgcctgg tcaaggacta cttccccgaa ccggtgacgg tgtcgtggaa ctcaggcgct | 540 |
| ctgaccagcg gcgtgcacac cttcccagct gtcctacagt cctcaggact ctactccctc | 600 |
| agcagcgtgg tgacagtgcc ctccagcaac ttcggcaccc agacctacac ctgcaacgta | 660 |
| gatcacaagc ccagcaacac caaggtggac aagacagttg agcgcaaatg ttgtgtcgag | 720 |
| tgcccaccgt gcccagcacc acctgtggca ggaccgtcag tcttcctctt ccccccaaaa | 780 |
| cccaaggaca ccctcatgat ctcccggacc cctgaggtca cgtgcgtggt ggtggacgtg | 840 |
| agccacgaag accccgaggt ccagttcaac tggtacgtgg acggcgtgga ggtgcataat | 900 |
| gccaagacaa agccacggga ggagcagttc aacagcacgt tccgtgtggt cagcgtcctc | 960 |
| accgttgtgc accaggactg gctgaacggc aaggagtaca agtgcaaggt ctccaacaaa | 1020 |
| ggcctcccag cccccatcga gaaaaccatc tccaaaacca agggcagcc ccgagaacca | 1080 |
| caggtgtaca ccctgcccc atcccgggag gagatgacca agaaccaggt cagcctgacc | 1140 |
| tgcctggtca aaggcttcta ccccagcgac atcgccgtgg agtgggagag caatgggcag | 1200 |
| ccggagaaca actacaagac cacacctccc atgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatga | 1386 |

<210> SEQ ID NO 139
<211> LENGTH: 1386
<212> TYPE: DNA
<213> ORGANISM: Homo sapiens

<400> SEQUENCE: 139

| | |
|---|---|
| atggcttggg tgtggacctt gccattcctg atggcagctg cccaaagtgt ccaggcccag | 60 |
| gtgcagctgg tcgagagcgg cggagggctg gtgcagcctg gcggcagcct gagactgagc | 120 |

```
tgcgccgcca gcggcttcac cttcagaagc cactggctgt cctgggtgcg gcaggcccct      180
ggcaagggcc tggaatgggt gtccgtgacc acccaccagg gctacaccta ctacgccgac      240
agcgtgaagg gccggttcac catcagccgg gacaacagca agaacaccct gtacctgcag      300
atgaacagct gcggggccga ggacaccgcc gtgtactact gcgccaggga cacctacctg      360
cacttcgact actggggcca gggcaccctg gtcaccgtct cctcagcttc caccaagggc      420
ccatccgtct tccccctggc gcctgctcc aggagcacct ccgagagcac agcggccctg      480
ggctgcctgg tcaaggacta cttccccgaa ccggtgacgg tgtcgtggaa ctcaggcgct      540
ctgaccagcg gcgtgcacac cttcccagct gtcctacagt cctcaggact ctactccctc      600
agcagcgtgg tgacagtgcc ctccagcaac ttcggcaccc agacctacac ctgcaacgta      660
gatcacaagc ccagcaacac caaggtggac aagacagttg agcgcaaatg ttgtgtcgag      720
tgcccaccgt gcccagcacc acctgtggca ggaccgtcag tcttcctctt ccccccaaaa      780
cccaaggaca ccctcatgat ctcccggacc cctgaggtca cgtgcgtggt ggtggacgtg      840
agccacgaag acccccgaggt ccagttcaac tggtacgtgg acggcgtgga ggtgcataat      900
gccaagacaa agccacggga ggagcagttc aacagcacgt tccgtgtggt cagcgtcctc      960
accgttgtgc accaggactg gctgaacggc aaggagtaca agtgcaaggt ctccaacaaa     1020
ggcctcccag cccccatcga gaaaaccatc tccaaaacca agggcagccc cgagaaccca     1080
caggtgtaca ccctgccccc atcccgggag gagatgacca agaaccaggt cagcctgacc     1140
tgcctggtca aaggcttcta ccccagcgac atcgccgtgg agtgggagag caatgggcag     1200
ccggagaaca actacaagac cacacctccc atgctggact ccgacggctc cttcttcctc     1260
tacagcaagc tcaccgtgga caagagcagg tggcagcagg ggaacgtctt ctcatgctcc     1320
gtgatgcatg aggctctgca caaccactac acgcagaaga gcctctccct gtctccgggt     1380
aaatga                                                                1386
```

<210> SEQ ID NO 140
<211> LENGTH: 1386
<212> TYPE: DNA
<213> ORGANISM: Homo sapiens

<400> SEQUENCE: 140

```
atggcttggg tgtggacctt gcattcctg atggcagctg cccaaagtgt ccaggcccag       60
gtgcagctgg tcgagagcgg cggagggctg gtgcagcctg gcggcagcct gagactgagc      120
tgcgccgcca gcggcttcac cttcagaagc cactggctgt cctgggtgcg gcaggcccct      180
ggcaagggcc tggaatgggt gtccgccacc aacagatacg gctacaccta ctacgccgac      240
agcgtgaagg gccggttcac catcagccgg gacaacagca agaacaccct gtacctgcag      300
atgaacagcc tgcgggccga ggacaccgcc gtgtactact gcgccaggga cacctacctg      360
cacttcgact actggggcca gggcaccctg gtcaccgtct cctcagcttc caccaagggc      420
ccatccgtct tccccctggc gcctgctcc aggagcacct ccgagagcac agcggccctg      480
ggctgcctgg tcaaggacta cttccccgaa ccggtgacgg tgtcgtggaa ctcaggcgct      540
ctgaccagcg gcgtgcacac cttcccagct gtcctacagt cctcaggact ctactccctc      600
agcagcgtgg tgacagtgcc ctccagcaac ttcggcaccc agacctacac ctgcaacgta      660
gatcacaagc ccagcaacac caaggtggac aagacagttg agcgcaaatg ttgtgtcgag      720
tgcccaccgt gcccagcacc acctgtggca ggaccgtcag tcttcctctt ccccccaaaa      780
cccaaggaca ccctcatgat ctcccggacc cctgaggtca cgtgcgtggt ggtggacgtg      840
```

| | |
|---|---:|
| agccacgaag accccgaggt ccagttcaac tggtacgtgg acggcgtgga ggtgcataat | 900 |
| gccaagacaa agccacggga ggagcagttc aacagcacgt tccgtgtggt cagcgtcctc | 960 |
| accgttgtgc accaggactg gctgaacggc aaggagtaca agtgcaaggt ctccaacaaa | 1020 |
| ggcctcccag cccccatcga gaaaaccatc tccaaaacca agggcagcc ccgagaacca | 1080 |
| caggtgtaca cctgcccccc atcccgggag gagatgacca gaaccaggt cagcctgacc | 1140 |
| tgcctggtca aaggcttcta ccccagcgac atcgccgtgg agtgggagag caatgggcag | 1200 |
| ccggagaaca actacaagac cacacctccc atgctggact ccgacggctc cttcttcctc | 1260 |
| tacagcaagc tcaccgtgga caagagcagg tggcagcagg gaacgtctt ctcatgctcc | 1320 |
| gtgatgcatg aggctctgca aaccactac acgcagaaga gcctctccct gtctccgggt | 1380 |
| aaatga | 1386 |

<210> SEQ ID NO 141
<211> LENGTH: 1389
<212> TYPE: DNA
<213> ORGANISM: Homo sapiens

<400> SEQUENCE: 141

| | |
|---|---:|
| atggcttggg tgtggaccct gccattcctg atggcagctg cccaaggtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggcccct | 180 |
| ggcaagggcc tggaatgggt gtccaacatc aactacgacg gcagcagcac ctactacgcc | 240 |
| gacagcgtga agggccggtt caccatcagc cgggacaaca gcaagaacac cctgtacctg | 300 |
| cagatgaaca gcctgcgggc cgaggacacc gccgtgtact actgcgccag ggacacctac | 360 |
| ctgcacttcg actactgggg ccagggcacc ctggtcaccg tctcctcagc ttccaccaag | 420 |
| ggcccatccg tcttccccct ggcgccctgc tccaggagca cctccgagag cacagcggcc | 480 |
| ctgggctgcc tggtcaagga ctacttcccc gaaccggtga cggtgtcgtg gaactcaggc | 540 |
| gctctgacca gcggcgtgca caccttccca gctgtcctac agtcctcagg actctactcc | 600 |
| ctcagcagcg tggtgacagt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg gcaggaccgt cagtcttcct cttccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg ggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga caactacaa gaccacacct cccatgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga gagcctctc cctgtctccg | 1380 |
| ggtaaatga | 1389 |

<210> SEQ ID NO 142
<211> LENGTH: 1386
<212> TYPE: DNA

<213> ORGANISM: Homo sapiens

<400> SEQUENCE: 142

```
atggcttggg tgtggacctt gccattcctg atggcagctg cccaaagtgt ccaggcccag      60
gtgcagctgg tcgagagcgg cggagggctg gtgcagcctg gcggcagcct gagactgagc     120
tgcgccgcca gcggcttcac cttcagaagc cactggctgt cctgggtgcg gcaggcccct     180
ggcaagggcc tggaatgggt gtccgtgatc accccctacg gcgacaccta ctacgccgac     240
agcgtgaagg gccggttcac catcagccgg gacaacagca gaacaccct gtacctgcag      300
atgaacagcc tgcgggccga ggacaccgcc gtgtactact gcgccaggga cacctacctg     360
cacttcgact actggggcca gggcaccctg gtcaccgtct cctcagcttc caccaagggc     420
ccatccgtct tccccctggc gccctgctcc aggagcacct ccgagagcac agcggccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
agcagcgtgg tgacagtgcc ctccagcaac ttcggcaccc agacctacac ctgcaacgta     660
gatcacaagc ccagcaacac caaggtggac aagacagttg agcgcaaatg ttgtgtcgag     720
tgcccaccgt gcccagcacc acctgtggca ggaccgtcag tcttcctctt ccccccaaaa     780
cccaaggaca ccctcatgat ctcccggacc cctgaggtca cgtgcgtggt ggtggacgtg     840
agccacgaag accccgaggt ccagttcaac tggtacgtgg acggcgtgga ggtgcataat     900
gccaagacaa agccacggga ggagcagttc aacagcacgt tccgtgtggt cagcgtcctc     960
accgttgtgc accaggactg gctgaacggc aaggagtaca agtgcaaggt ctccaacaaa    1020
ggcctcccag cccccatcga gaaaaccatc tccaaaacca agggcagcc ccgagaacca     1080
caggtgtaca ccctgccccc atcccgggag gagatgacca agaaccaggt cagcctgacc    1140
tgcctggtca aaggcttcta ccccagcgac atcgccgtgg agtgggagag caatgggcag    1200
ccggagaaca actacaagac cacacctccc atgctggact ccgacggctc cttcttcctc    1260
tacagcaagc tcaccgtgga caagagcagg tggcagcagg ggaacgtctt ctcatgctcc    1320
gtgatgcatg aggctctgca caaccactac acgcagaaga gcctctccct gtctccgggt    1380
aaatga                                                              1386
```

<210> SEQ ID NO 143
<211> LENGTH: 1386
<212> TYPE: DNA
<213> ORGANISM: Homo sapiens

<400> SEQUENCE: 143

```
atggcttggg tgtggacctt gccattcctg atggcagctg cccaaagtgt ccaggcccag      60
gtgcagctgg tcgagagcgg cggagggctg gtgcagcctg gcggcagcct gagactgagc     120
tgcgccgcca gcggcttcac cttcagaagc cactggctgt cctgggtgcg gcaggcccct     180
ggcaagggcc tggaatgggt gtccgtgatc accccctacg gcgacaccta ctacgccgac     240
agcgtgaagg gccggttcac catcagccgg gacaacagca gaacaccct gtacctgcag      300
atgaacagcc tgcgggccga ggacaccgcc gtgtactact gcgccaggga cacctacctg     360
cacttcgact actggggcca gggcaccctg gtcaccgtct cctcagcttc caccaagggc     420
ccatccgtct tccccctggc gccctgctcc aggagcacct ccgagagcac agcggccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
```

| | |
|---|---|
| agcagcgtgg tgacagtgcc ctccagcaac ttcggcaccc agacctacac ctgcaacgta | 660 |
| gatcacaagc ccagcaacac caaggtggac aagacagttg agcgcaaatg ttgtgtcgag | 720 |
| tgcccaccgt gcccagcacc acctgtggca ggaccgtcag tcttcctctt ccccccaaaa | 780 |
| cccaaggaca ccctcatgat ctcccggacc cctgaggtca cgtgcgtggt ggtggacgtg | 840 |
| agccacgaag accccgaggt ccagttcaac tggtacgtgg acggcgtgga ggtgcataat | 900 |
| gccaagacaa agccacggga ggagcagttc aacagcacgt tccgtgtggt cagcgtcctc | 960 |
| accgttgtgc accaggactg gctgaacggc aaggagtaca agtgcaaggt ctccaacaaa | 1020 |
| ggcctcccag cccccatcga gaaaaccatc tccaaaacca agggcagccc cgagaaccca | 1080 |
| caggtgtaca ccctgccccc atcccgggag gagatgacca agaaccaggt cagcctgacc | 1140 |
| tgcctggtca aaggcttcta ccccagcgac atcgccgtgg agtgggagag caatgggcag | 1200 |
| ccggagaaca actacaagac cacacctccc atgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatga | 1386 |

<210> SEQ ID NO 144
<211> LENGTH: 393
<212> TYPE: DNA
<213> ORGANISM: Homo sapiens

<400> SEQUENCE: 144

| | |
|---|---|
| atgaaaaaga cagctatcgc gattgcagtg gcactggctg gtttcgctac cgtagcgcag | 60 |
| gccgatatcg aactgaccca gccgccttca gtgagcgttg caccaggtca gaccgcgcgt | 120 |
| atctcgtgta gcggcgataa tattggttct ttttatgttc attggtacca gcagaaaccc | 180 |
| gggcaggcgc cagttcttgt gatttatgat gataataatc gtccctcagg catcccggaa | 240 |
| cgctttagcg gatccaacag cggcaacacc gcgaccctga ccattagcgg cactcaggcg | 300 |
| gaagacgaag cggattatta ttgcggttct tgggctggtt cttctggttc ttatgtgttt | 360 |
| ggcggccgca cgaagttaac cgttcttggc cag | 393 |

<210> SEQ ID NO 145
<211> LENGTH: 714
<212> TYPE: DNA
<213> ORGANISM: Homo sapiens

<400> SEQUENCE: 145

| | |
|---|---|
| atgagtgtgc tcactcaggt cctggcgttg ctgctgctgt ggcttacagg tacgcgttgc | 60 |
| gacatcgccc tgacccagcc cgccagcgtg agcggcagcc tggccagag catcaccatc | 120 |
| agctgcaccg gcaccagcag cgacgtgggc gacatcaacg acgtgagctg gtatcagcag | 180 |
| caccccggca aggcccccaa gctgatgatc tacgacgtga caaccggcc cagcggcgtg | 240 |
| agcaaccggt tcagcggcag caagagcggc aacaccgcca gcctgaccat cagcggcctc | 300 |
| caggccgagg acgaggccga ctactactgc agcagctacg cgagagcct gaccagctac | 360 |
| gtgtttggcg gcggaaccaa gcttaccgtc ctaggtcagc ccaaggctgc cccctcggtc | 420 |
| actctgttcc cgccctcctc tgaggagctt caagccaaca ggccacact ggtgtgtctc | 480 |
| ataagtgact tctacccggg agccgtgaca gtggcctgga aggcagatag cagccccgtc | 540 |
| aaggcgggag tggagacaac cacaccctcc aaacaaagca caacaagta cgcggccagc | 600 |
| agctatctga gcctgacgcc tgagcagtgg aagtcccaca gaagctacag ctgccaggtc | 660 |

```
acgcatgaag ggagcaccgt ggaaaagaca gtggccccta cagaatgttc atag        714

<210> SEQ ID NO 146
<211> LENGTH: 705
<212> TYPE: DNA
<213> ORGANISM: Homo sapiens

<400> SEQUENCE: 146
atgagtgtgc tcactcaggt cctggcgttg ctgctgctgt ggcttacagg tacgcgttgc    60
gacatcgagc tgacccagcc ccccagcgtg agcgtggccc ctggccagac cgcccggatc   120
agctgcagcg gcgacaacat cggcagcttc tacgtgcact ggtatcagca gaagcccggc   180
caggccccca tgctggtgat ctacgacgac aacaaccggc ccagcggcat ccccgagcgg   240
ttcagcggca gcaacagcgg caacaccgcc accctgacca tcagcggcac ccaggccgag   300
gacgaggccg actactactg cgccagctgg accggcgtgg agcccgacta cgtgtttggc   360
ggcggaacaa agcttaccgt cctaggtcag cccaaggctg cccctcggt cactctgttc    420 ccgccctcct ctgaggagct tcaagccaac aaggccacac tggtgtgtct cataagtgac   480
ttctacccgg gagccgtgac agtggcctgg aaggcagata gcagcccgt caaggcggga    540 gtggagacaa ccacaccctc caaacaaagc aacaacaagt acgcggccag cagctatctg   600
agcctgacgc ctgagcagtg gaagtcccac agaagctaca gctgccaggt cacgcatgaa   660
gggagcaccg tggaaaagac agtggcccct acagaatgtt catag                   705

<210> SEQ ID NO 147
<211> LENGTH: 714
<212> TYPE: DNA
<213> ORGANISM: Homo sapiens

<400> SEQUENCE: 147
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180 cacccccggca aggcccccaa gctgatgatc tacgacgtga caaccggcc cagcggcgtg    240 agcaaccggt tcagcggcag caagagcggc aacaccgcca gcctgaccat cagcggcctc   300
caggccgagg acgaggccga ctactactgc cagagctacg ccggcagcta cctgagcgag   360
gtgttcggcg gagggaccaa gcttaccgtc ctaggtcagc ccaaggctgc ccctcggtc    420 actctgttcc cgccctcctc tgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca acaacaagta cgcggccagc   600
agctatctga gcctgacgcc tgagcagtgg aagtcccaca gaagctacag ctgccaggtc   660
acgcatgaag ggagcaccgt ggaaaagaca gtggccccta cagaatgttc atag         714

<210> SEQ ID NO 148
<211> LENGTH: 714
<212> TYPE: DNA
<213> ORGANISM: Homo sapiens

<400> SEQUENCE: 148
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180
```

```
caccccggca aggcccccaa gctgatgatc tacgacgtga acaaccggcc cagcggcgtg    240
agcaaccggt tcagcggcag caagagcggc aacaccgcca gcctgaccat cagcggcctc    300
caggccgagg acgaggccga ctactactgc agcagctacg gcgagagcct gaccagctac    360
gtgtttggcg gcggaaccaa gcttaccgtc ctaggtcagc ccaaggctgc cccctcggtc    420
actctgttcc cgccctcctc tgaggagctt caagccaaca aggccacact ggtgtgtctc    480
ataagtgact tctacccggg agccgtgaca gtggcctgga aggcagatag cagccccgtc    540
aaggcgggag tggagacaac cacaccctcc aaacaaagca acaacaagta cgcggccagc    600
agctatctga gcctgacgcc tgagcagtgg aagtcccaca aagctacag ctgccaggtc    660 acgcatgaag ggagcaccgt ggaaaagaca gtggcccta cagaatgttc atag    714
```

<210> SEQ ID NO 149
<211> LENGTH: 714
<212> TYPE: DNA
<213> ORGANISM: Homo sapiens

<400> SEQUENCE: 149

```
atgagtgtgc tcactcaggt cctggcgttg ctgctgctgt ggcttacagg tacgcgttgc     60
gacatcgccc tgacccagcc cgccagcgtg agcggcagcc ctggccagag catcaccatc    120
agctgcaccg gcaccagcag cgacgtgggc gacatcaacg acgtgagctg gtatcagcag    180
caccccggca aggcccccaa gctgatgatc tacgacgtga acaaccggcc cagcggcgtg    240
agcaaccggt tcagcggcag caagagcggc aacaccgcca gcctgaccat cagcggcctc    300
caggccgagg acgaggccga ctactactgc agcagctacg gcgagagcct gaccagctac    360
gtgtttggcg gcggaaccaa gcttaccgtc ctaggtcagc ccaaggctgc cccctcggtc    420
actctgttcc cgccctcctc tgaggagctt caagccaaca aggccacact ggtgtgtctc    480
ataagtgact tctacccggg agccgtgaca gtggcctgga aggcagatag cagccccgtc    540
aaggcgggag tggagacaac cacaccctcc aaacaaagca acaacaagta cgcggccagc    600
agctatctga gcctgacgcc tgagcagtgg aagtcccaca aagctacag ctgccaggtc    660 acgcatgaag ggagcaccgt ggaaaagaca gtggcccta cagaatgttc atag    714
```

<210> SEQ ID NO 150
<211> LENGTH: 714
<212> TYPE: DNA
<213> ORGANISM: Homo sapiens

<400> SEQUENCE: 150

```
atgagtgtgc tcactcaggt cctggcgttg ctgctgctgt ggcttacagg tacgcgttgc     60
gacatcgccc tgacccagcc cgccagcgtg agcggcagcc ctggccagag catcaccatc    120
agctgcaccg gcaccagcag cgacgtgggc gacatcaacg acgtgagctg gtatcagcag    180
caccccggca aggcccccaa gctgatgatc tacgacgtga acaaccggcc cagcggcgtg    240
agcaaccggt tcagcggcag caagagcggc aacaccgcca gcctgaccat cagcggcctc    300
caggccgagg acgaggccga ctactactgc agcagctacg gcgagagcct gaccagctac    360
gtgtttggcg gcggaaccaa gcttaccgtc ctaggtcagc ccaaggctgc cccctcggtc    420
actctgttcc cgccctcctc tgaggagctt caagccaaca aggccacact ggtgtgtctc    480
ataagtgact tctacccggg agccgtgaca gtggcctgga aggcagatag cagccccgtc    540
aaggcgggag tggagacaac cacaccctcc aaacaaagca acaacaagta cgcggccagc    600
agctatctga gcctgacgcc tgagcagtgg aagtcccaca aagctacag ctgccaggtc    660
```

```
acgcatgaag ggagcaccgt ggaaaagaca gtggccccta cagaatgttc atag      714
```

<210> SEQ ID NO 151
<211> LENGTH: 714
<212> TYPE: DNA
<213> ORGANISM: Homo sapiens

<400> SEQUENCE: 151

```
atgagtgtgc tcactcaggt cctggcgttg ctgctgctgt ggcttacagg tacgcgttgc      60
gacatcgccc tgacccagcc cgccagcgtg agcggcagcc ctggccagag catcaccatc     120
agctgcaccg gcaccagcag cgacgtgggc gacatcaacg acgtgagctg gtatcagcag     180
cacccccggca aggcccccaa gctgatgatc tacgacgtga caaccggcc cagcggcgtg     240
agcaaccggt tcagcggcag caagagcggc aacaccgcca gcctgaccat cagcggcctc     300
caggccgagg acgaggccga ctactactgc agcagctacg cgagagcct gaccagctac     360
gtgtttggcg gcggaaccaa gcttaccgtc ctaggtcagc ccaaggctgc ccctcggtc     420
actctgttcc cgccctcctc tgaggagctt caagccaaca aggccacact ggtgtgtctc     480
ataagtgact tctacccggg agccgtgaca gtggcctgga aggcagatag cagccccgtc     540
aaggcgggag tggagacaac cacaccctcc aaacaaagca acaacaagta cgcggccagc     600
agctatctga gcctgacgcc tgagcagtgg aagtcccaca gaagctacag ctgccaggtc     660
acgcatgaag ggagcaccgt ggaaaagaca gtggccccta cagaatgttc atag     714
```

<210> SEQ ID NO 152
<211> LENGTH: 714
<212> TYPE: DNA
<213> ORGANISM: Homo sapiens

<400> SEQUENCE: 152

```
atgagtgtgc tcactcaggt cctggcgttg ctgctgctgt ggcttacagg tacgcgttgc      60
gacatcgccc tgacccagcc cgccagcgtg agcggcagcc ctggccagag catcaccatc     120
agctgcaccg gcaccagcag cgacgtgggc gacatcaacg acgtgagctg gtatcagcag     180
cacccccggca aggcccccaa gctgatgatc tacgacgtga caaccggcc cagcggcgtg     240
agcaaccggt tcagcggcag caagagcggc aacaccgcca gcctgaccat cagcggcctc     300
caggccgagg acgaggccga ctactactgc agcacctacg acggccctgg cctgagcgag     360
gtgttcggcg gagggaccaa gcttaccgtc ctaggtcagc ccaaggctgc ccctcggtc     420
actctgttcc cgccctcctc tgaggagctt caagccaaca aggccacact ggtgtgtctc     480
ataagtgact tctacccggg agccgtgaca gtggcctgga aggcagatag cagccccgtc     540
aaggcgggag tggagacaac cacaccctcc aaacaaagca acaacaagta cgcggccagc     600
agctatctga gcctgacgcc tgagcagtgg aagtcccaca gaagctacag ctgccaggtc     660
acgcatgaag ggagcaccgt ggaaaagaca gtggccccta cagaatgttc atag     714
```

<210> SEQ ID NO 153
<211> LENGTH: 714
<212> TYPE: DNA
<213> ORGANISM: Homo sapiens

<400> SEQUENCE: 153

```
atgagtgtgc tcactcaggt cctggcgttg ctgctgctgt ggcttacagg tacgcgttgc      60
gacatcgccc tgacccagcc cgccagcgtg agcggcagcc ctggccagag catcaccatc     120
agctgcaccg gcaccagcag cgacgtgggc gacatcaacg acgtgagctg gtatcagcag     180
```

```
caccccggca aggcccccaa gctgatgatc tacgacgtga acaaccggcc cagcggcgtg    240
agcaaccggt tcagcggcag caagagcggc aacaccgcca gcctgaccat cagcggcctc    300
caggccgagg acgaggccga ctactactgc agcacctacg acggccctgg cctgagcgag    360
gtgttcggcg agggaccaa gcttaccgtc ctaggtcagc ccaaggctgc ccctcggtc      420 actctgttcc cgccctcctc tgaggagctt caagccaaca aggccacact ggtgtgtctc    480
ataagtgact tctacccggg agccgtgaca gtggcctgga aggcagatag cagccccgtc    540
aaggcgggag tggagacaac cacaccctcc aaacaaagca acaacaagta cgcggccagc    600
agctatctga gcctgacgcc tgagcagtgg aagtcccaca aagctacag ctgccaggtc     660 acgcatgaag ggagcaccgt ggaaaagaca gtggccccta cagaatgttc atag          714

<210> SEQ ID NO 154
<211> LENGTH: 714
<212> TYPE: DNA
<213> ORGANISM: Homo sapiens

<400> SEQUENCE: 154
atgagtgtgc tcactcaggt cctggcgttg ctgctgctgt ggcttacagg tacgcgttgc     60
gacatcgccc tgacccagcc cgccagcgtg agcggcagcc ctggccagag catcaccatc    120
agctgcaccg gcaccagcag cgacgtgggc gacatcaacg acgtgagctg gtatcagcag    180
caccccggca aggcccccaa gctgatgatc tacgacgtga acaaccggcc cagcggcgtg    240
agcaaccggt tcagcggcag caagagcggc aacaccgcca gcctgaccat cagcggcctc    300
caggccgagg acgaggccga ctactactgc agcacctacg acggccctgg cctgagcgag    360
gtgttcggcg agggaccaa gcttaccgtc ctaggtcagc ccaaggctgc ccctcggtc      420 actctgttcc cgccctcctc tgaggagctt caagccaaca aggccacact ggtgtgtctc    480
ataagtgact tctacccggg agccgtgaca gtggcctgga aggcagatag cagccccgtc    540
aaggcgggag tggagacaac cacaccctcc aaacaaagca acaacaagta cgcggccagc    600
agctatctga gcctgacgcc tgagcagtgg aagtcccaca aagctacag ctgccaggtc     660 acgcatgaag ggagcaccgt ggaaaagaca gtggccccta cagaatgttc atag          714

<210> SEQ ID NO 155
<211> LENGTH: 213
<212> TYPE: PRT
<213> ORGANISM: homo sapiens

<400> SEQUENCE: 155

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
```

```
              115                 120                 125
Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
        210

<210> SEQ ID NO 156
<211> LENGTH: 14
<212> TYPE: PRT
<213> ORGANISM: Homo sapiens

<400> SEQUENCE: 156

Ala Arg Leu Leu Asn Ala Ile Gly Arg Gly Lys Trp Trp Arg
1               5                   10

<210> SEQ ID NO 157
<211> LENGTH: 15
<212> TYPE: PRT
<213> ORGANISM: Homo sapiens

<400> SEQUENCE: 157

Arg Leu Val Ala Ser Cys Lys Cys Lys Arg Leu Thr Arg Phe His
1               5                   10                  15

<210> SEQ ID NO 158
<211> LENGTH: 13
<212> TYPE: PRT
<213> ORGANISM: Artificial
<220> FEATURE:
<223> OTHER INFORMATION: Protein linker sequence

<400> SEQUENCE: 158

Gly Gly Gly Ser Gly Gly Gly Ser Gly Gly Gly Gly
1               5                   10

<210> SEQ ID NO 159
<211> LENGTH: 19
<212> TYPE: PRT
<213> ORGANISM: Artificial
<220> FEATURE:
<223> OTHER INFORMATION: Protein linker sequence

<400> SEQUENCE: 159

Gly Gly Gly Gly Ser Gly Gly Gly Ser Gly Gly Gly Gly Ser Gly
1               5                   10                  15

Gly Gly Gly

<210> SEQ ID NO 160
<211> LENGTH: 21
<212> TYPE: DNA
<213> ORGANISM: Artificial
<220> FEATURE:
<223> OTHER INFORMATION: siRNA

<400> SEQUENCE: 160
```

```
taaattatca taaagtccta a                                              21

<210> SEQ ID NO 161
<211> LENGTH: 21
<212> TYPE: DNA
<213> ORGANISM: Artificial
<220> FEATURE:
<223> OTHER INFORMATION: siRNA

<400> SEQUENCE: 161
aggactttat gataatttat t                                              21

<210> SEQ ID NO 162
<211> LENGTH: 21
<212> TYPE: DNA
<213> ORGANISM: Artificial
<220> FEATURE:
<223> OTHER INFORMATION: siRNA

<400> SEQUENCE: 162
atagtggtta aataactcca g                                              21

<210> SEQ ID NO 163
<211> LENGTH: 21
<212> TYPE: DNA
<213> ORGANISM: Artificial
<220> FEATURE:
<223> OTHER INFORMATION: siRNA

<400> SEQUENCE: 163
ggagttattt aaccactatt t                                              21

<210> SEQ ID NO 164
<211> LENGTH: 21
<212> TYPE: DNA
<213> ORGANISM: Artificial
<220> FEATURE:
<223> OTHER INFORMATION: siRNA

<400> SEQUENCE: 164
taaattctcg tgatgtgcca t                                              21

<210> SEQ ID NO 165
<211> LENGTH: 21
<212> TYPE: DNA
<213> ORGANISM: Artificial
<220> FEATURE:
<223> OTHER INFORMATION: siRNA

<400> SEQUENCE: 165
ggcacatcac gagaatttat t                                              21

<210> SEQ ID NO 166
<211> LENGTH: 21
<212> TYPE: DNA
<213> ORGANISM: Artificial
<220> FEATURE:
<223> OTHER INFORMATION: siRNA

<400> SEQUENCE: 166
tttcttatag cacagctggt t                                              21

<210> SEQ ID NO 167
<211> LENGTH: 21
<212> TYPE: DNA
<213> ORGANISM: Artificial
<220> FEATURE:
```

```
<223> OTHER INFORMATION: siRNA

<400> SEQUENCE: 167
ccagctgtgc tataagaaat t                                      21

<210> SEQ ID NO 168
<211> LENGTH: 21
<212> TYPE: DNA
<213> ORGANISM: Artificial
<220> FEATURE:
<223> OTHER INFORMATION: siRNA

<400> SEQUENCE: 168
tagacctttc catccacgct g                                      21

<210> SEQ ID NO 169
<211> LENGTH: 21
<212> TYPE: DNA
<213> ORGANISM: Artificial
<220> FEATURE:
<223> OTHER INFORMATION: siRNA

<400> SEQUENCE: 169
gcgtggatgg aaaggtctat t                                      21

<210> SEQ ID NO 170
<211> LENGTH: 29
<212> TYPE: DNA
<213> ORGANISM: Artificial
<220> FEATURE:
<223> OTHER INFORMATION: RT-PCT primer

<400> SEQUENCE: 170
atgcagctcc cactggccct gtgtcttgt                              29

<210> SEQ ID NO 171
<211> LENGTH: 30
<212> TYPE: DNA
<213> ORGANISM: Artificial
<220> FEATURE:
<223> OTHER INFORMATION: RT-PCR primer

<400> SEQUENCE: 171
aatcaggccg agctggagaa cgcctactag                             30
```

POLYNUCLEOTIDES ENCODING ANTIBODIES AGAINST SCLEROSTIN AND USES THEREFOR

RELATED APPLICATIONS

This application is a continuation of U.S. patent application Ser. No. 12/944,019 filed on Nov. 11, 2010, which issued as U.S. Pat. No. 8,246,953 on Aug. 21, 2012, which is a continuation of U.S. application Ser. No. 12/249,050 filed on Oct. 10, 2008, which issued as U.S. Pat. No. 7,879,322 on Feb. 1, 2011, and which claims benefit of EP Application No 07118414.7 filed on Oct. 12, 2007, EP Application No 08151911.8 filed on Feb. 25, 2008, and EP Application No. 08161342.4 filed on Jul. 29, 2008, the entire disclosures of which are hereby incorporated by reference.

TECHNICAL FIELD

The present invention relates to antibodies against sclerostin and compositions and methods of use for said antibodies to treat a pathological disorder that is mediated by sclerostin or disease related to bone abnormalities such as osteoporosis.

BACKGROUND OF THE INVENTION

The SOST gene encodes the protein sclerostin which is a 213 amino acids secreted glycoprotein. Sclerostin is a member of the super-family of cystine-knot containing factors. Sclerostin is related to the DAN/Cerberus protein family, which interferes directly with BMP signaling by inhibiting the binding of BMP to the receptors and thus the BMP signaling cascade (Avsian-Kretchmer, Mol Endocrinol 2004, 18(1):1-12).

Sclerostin mRNA expression is detected in adult humans predominantly in bone and kidney. Sclerostin protein is detectable predominantly in bone. Within bone its expression is restricted to the mature and terminally differentiated bone forming cells, the osteocytes.

Sclerostin is a potent negative regulator of bone formation in men and mice. Lack of SOST expression gives rise to sclerosteosis (Balemans et al. Hum Mol. Genet., 2001, 10(5): 537-43; Brunkow et al. Am J Hum Genet, 2001, 68(3):577-89). Patients suffer from life-long bone overgrowth resulting in increased bone mineral density and strength. They display no other endocrinological abnormalities—all complications they experience during their life-time are related to the abnormal accumulation of bone. Heterozygous carriers for this recessive disorder also display increased bone mass (Gardner et al. J Clin Endocrinol Metab, 2005, 90(12):6392-5). This phenotype can be recapitulated in SOST deficient mice and its overexpression results in osteopenia. Furthermore Van Buchem disease [MIM 239100]—a phenotypic copy of sclerosteosis—is caused by SOST misregulation due to the genomic deletion of a long-range bone enhancer (Balemans et al. J Med Gene, 2002, 39(2):91-7; Loots et al., Genome Res, 2005, 15(7):928-35). Finally, SOST is down-regulated by parathyroid hormone—a clinically validated bone forming principle—during bone formation suggesting that part of the anabolic action of PTH might be mediated via SOST (Keller and Kneissel Bone, 2005, 37(2):148-58).

Sclerostin binds BMPs (bone morphogenic proteins) and can act as a BMP antagonist in vitro (Winkler et al. EMBO J., 2003, 22(23):6267-76). Sclerostin also acts as a negative regulator of canonical Wnt signaling, either directly by binding to LRP5/LRP6 (Li et al. J Biol. Chem., 2005, 20; 280(20); Semenov, J Biol. Chem. 2006 Oct. 19; van Bezooijen et al. J Bone Miner Res, 2006, October 10), or indirectly (Winkler et al. J Biol. Chem., 2005, 28; 280(4):2498-502).

Lack of sclerostin expression results in high bone formation, while bone resorption is undisturbed (Sclerosteosis, Van Buchem disease) (Balemans et al. 2001; Brunkow et al. Am J Hum Genet, 2001, 68(3):577-89, Balemans et al. 2006; Loots et al., Genome Res, 2005, 15(7):928-35).

Few of the presently available treatments for skeletal disorders can increase the bone density of adults, and most of the presently available treatments work primarily by inhibiting further bone resorption rather than stimulating new bone formation.

One example of a medicament used for treating bone loss is estrogen. However, it is not clear whether or not estrogen has any beneficial long term effects. Furthermore, estrogen may carry the risk of increasing the prevalence of various types of tumors, such as breast and endometrial cancer. Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects.

SUMMARY OF THE INVENTION

An embodiment of the invention herein provides an antibody or a functional protein comprising an antigen-binding portion of said antibody for a target in sclerostin polypeptide (SEQ ID NO:155), characterized in that the antibody or functional protein specifically binds to sclerostin polypeptide and can increase at least one of bone formation, bone mineral density, bone mineral content, bone mass, bone quality and bone strength in a mammal.

In one embodiment, the antibodies according to the invention have the ability to reverse sclerostin inhibition of in vitro bone mineralization. In a related embodiment, they have the ability to reverse sclerostin inhibition of wnt-1 mediated signaling pathway. In another related embodiment, they disrupt sclerostin LRP6 binding and can block the inhibitory effect that sclerostin has at high doses on BMP induced Smad1 phosphorylation. In another embodiment, the antibodies of the invention bind to a region of sclerostin between amino acids 112 and 126 inclusive (i.e. said region consists of amino acids 112 to 126 of SEQ ID NO:155) of SEQ ID NO:155 and/or the region between amino acids 160-174 inclusive (i.e. said region consists of amino acids 160 to 174 of SEQ ID NO:155) of SEQ ID NO:155, and more specifically, bind to a region comprising both ARLLPNAIGRGKWWR (SEQ ID NO 156) and RLVASCKCKRLTRFH (SEQ ID NO 157).

Sclerostin inhibits wnt1-mediated activation of STF (Supertopflash, reporter readout for canonical wnt signaling) in HEK293 cells. In some embodiments, the antibodies of the invention restore the wnt signaling reporter readout in a highly reproducible manner.

The observed inhibitory effect of the antibodies according to the invention on sclerostin action in the Wnt signaling reporter assay in non-osteoblastic cells has been shown to translate into induction of bone formation responses due to sclerostin inhibition in vivo. Indeed, in vivo experiments in aged rodents show that the antibodies according to the invention promotes strong bone anabolism. The bone mass increase reached the effect level of daily intermittent treatment with extremely high anabolic doses of parathyroid hormone (which was used as a positive control).

Therefore, according to another preferred embodiment, the antibodies according to the invention have affinities to sclerostin in the low pM range and inhibit sclerostin impact on wnt signalling with an $IC_{50}$ around 10 nM.

More preferably, in another preferred embodiment, the antibodies according to the invention bind to a region of sclerostin comprised between amino acids 112 and 126 inclusive (i.e. said region consists of amino acids 112 to 126 of SEQ ID NO:155) and between amino acids 160 and 174 inclusive (i.e. said region consists of amino acids 160 to 174 of SEQ ID NO:155) of SEQ ID NO:155, and more specifically a region that overlaps at least the following peptides ARLLPNAIGRGKWWR (SEQ ID NO: 156) and RLVASCKCKRLTRFH (SEQ ID NO:157), respectively, and have affinities to sclerostin in the low pM range and inhibit sclerostin impact on wnt signalling with an $IC_{50}$ around 10 nM. Such antibodies have the capacity to increase bone mass in the axial and appendicular skeleton of mouse animal model at the effect level of daily subcutaneous treatment with an extremely high anabolic dose of parathyroid hormone (positive control) and are therefore useful in the treatment of disease related to bone abnormalities such as osteoporosis.

Further embodiments include compositions comprising the antibodies of the invention in combination with alternative therapies for treating osteoporosis, such as bisphosphonates, parathyroid hormone, parathyroid hormone releasing agents (calcilytics), LRP4 neutralising antibodies and DKK-1 neutralising antibodies.

BRIEF DESCRIPTION OF THE FIGURES

FIG. 2: MOR05813_IgG2lambda in BMP-2-induced mineralization in MC3T3-1b cells

FIG. 4: Effect of MOR05813_IgG2lambda in the Phospho-Smad1 assay

FIG. 21: Mouse study, in vivo pQCT following co-treatment with MOR05813 and zoledronic acid, (A) Total bone mineral density, (B) Total bone mineral content, (C) Cortical thickness, and (D) Cancellous bone mineral density FIG. 22: Mouse study, in vivo pQCT: treatment with MOR05813 following alendronate (alen) pre-treatment, (A) Total bone mineral density, (B) Total bone mineral content, (C) Cortical thickness, and (D) Cancellous bone mineral density FIG. 23: Mouse study, in vivo pQCT following anabolic co-treatment with MOR05813 and (i) anti-DKK1, or (ii) PTH, (A) Total bone mineral density, (B) Total bone mineral content, (C) Cortical thickness, and (D) Cancellous bone mineral density

DETAILED DESCRIPTION

Figure 1:
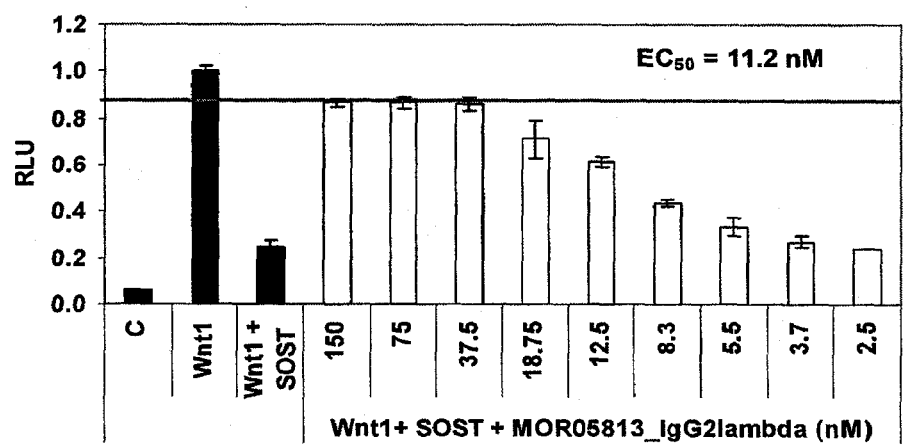
FIG. 1: Effect of MOR05813_IgG2lambda in the wnt-1 assay

The present invention relates to isolated antibodies, particularly human antibodies, that bind specifically to sclerostin and that inhibit functional properties of sclerostin. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and multivalent or multispecific molecules comprising such antibodies and pharmaceutical compositions containing the antibodies, immunoconjugates or bispecific molecules of the invention. The invention also relates to methods of using the antibodies to inhibit a disorder or condition associated with the presence of sclerostin expression, for example, in the treatment a pathological disorder that is mediated by sclerostin or that is associated with an increased level of sclerostin; for example, a bone related disease such as osteoporosis.

In order that the present invention may be more readily understood, certain terms are first defined. Additional definitions are set forth throughout the detailed description.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term sclerostin refers to human sclerostin as defined in SEQ ID NO: 155. Recombinant human sclerostin can be obtained from R&D Systems (Minneapolis, Minn., USA; 2006 cat#1406-ST-025). Additionally, recombinant mouse sclerostin/SOST is commercially available from R&D Systems (Minneapolis, Minn., USA; 2006 cat#1589-ST-025). U.S. Pat. Nos. 6,395,511 and 6,803,453, and U.S. Patent Publications 20040009535 and 20050106683 refer to anti-sclerostin antibodies in general.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antigen portion"), as used herein, refers to full length or one or more fragments of an antibody that retain the ability to specifically bind to an antigen (e.g., sclerostin). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a VH domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds sclerostin is substantially free of antibodies that specifically bind antigens other than sclerostin). An isolated antibody that specifically binds sclerostin may, however, have cross-reactivity to other antigens, such as sclerostin molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, at al. (2000. J Mol Biol 296, 57-86).

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline VH and VL sequences, may not naturally exist within the human antibody germline repertoire in vivo.

As used herein, "isotype" refers to the antibody class (e.g., IgM, IgE, IgG such as IgG1 or IgG2) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to sclerostin polypeptide" is intended to refer to an antibody that binds to sclerostin polypeptide with a $K_D$ of $1 \times 10^{-8}$ M or less, $1 \times 10^{-9}$ M or less, or $1 \times 10^{-19}$ M or less. An antibody that "cross-reacts with an antigen other than sclerostin" is intended to refer to an antibody that binds that antigen with a $K_D$ of $0.5 \times 10^{-8}$ M or less, 5×M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of between $5 \times 10^{-8}$ M and $10 \times 10^{-8}$ M, or $1 \times 10^{-7}$ M or greater. In certain embodiments, such antibodies that do not cross-react with the antigen exhibit essentially undetectable binding against these proteins in standard binding assays.

As used herein, an antibody that "blocks the inhibitory effect of sclerostin in a cell based wnt signaling assay" is intended to refer to an antibody that restores wnt induced signaling in the presence of sclerostin in a cell-based super top flash (STF) assay with an $IC_{50}$ less than 1 mM, 100 nM, 20 nM, 10 nM or less. Such STF assay is described in more details in the examples below.

As used herein, an antibody that "blocks the inhibitory effect of sclerostin in a cell based mineralization assay" is intended to refer to an antibody that restores BMP2 induced mineralisation in the presence of sclerostin in a cell-based assay with an $IC_{50}$ less than 1 mM, 500 nM, 100 nM, 10 nM, 1 nM or less. Such assay is described in more details in the examples below.

As used herein, an antibody that "blocks the inhibitory effect of sclerostin in Smad1 phosphorylation assay" is intended to refer to an antibody that restores BMP6 induced Smad1 phosphorylation in the presence of sclerostin in a cell based assay with an $IC_{50}$ less than 1 mM, 500 nM, 100 nM, 10 nM, 1 nM or less. Such assay is described in more details in the examples below.

As used herein, an antibody that "inhibits binding of sclerostin to the LRP-6" refers to an antibody that inhibits sclerostin binding to LRP-6 with a $IC_{50}$ of 1 mM, 500 nM, 100 nM, 10 nM, 5 nM, 3 nM, 1 nM or less. Such assay is described in more details in the examples below.

As used herein, an antibody that "increases bone formation and mass and density" refers to an antibody that is capable of reaching bone formation, mass and density at the level of daily intermittent treatment with high anabolic dose of PTH as shown in the Example 10.

The term "$K_{assoc}$" or "$K_a$", as used herein, is intended to refer to the association rate of a particular antibody-antigen interaction, whereas the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

In order to get a higher avidity probe, a dimeric conjugate can be constructed, thus making low affinity interactions (such as with the germline antibody) more readily detected by FACS. In addition, another means to increase the avidity of antigen binding involves generating dimmers, trimers or multimers of any of the constructs described herein of the anti-sclerostin antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in sclerostin hybrids to create such higher order structures. For example, it is possible to use multimerizing domains such as trimerizing domain described in Borean (WO2004039841) or pentamerizing domain described in published patent application WO98/18943.

As used herein, the term "cross-reactivity" refers to an antibody or population of antibodies binding to epitopes on other antigens. This can be caused either by low avidity or specificity of the antibody or by multiple distinct antigens having identical or very similar epitopes. Cross reactivity is sometimes desirable when one wants general binding to a related group of antigens or when attempting cross-species labeling when the antigen epitope sequence is not highly conserved in evolution.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, or $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia* or *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells, however optimized expression of these sequences in other eukaryotic cells is also envisioned herein. The amino acid sequences encoded by optimized nucleotide sequences are also referred to as optimized.

Various aspects of the invention are described in further detail in the following subsections.

Standard assays to evaluate the binding ability of the antibodies toward sclerostin of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of sclerostin (e.g., receptor binding, preventing or ameliorating osteolysis) are described in further detail in the Examples.

Accordingly, an antibody that "inhibits" one or more of these sclerostin functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits sclerostin activity effects such a statistically significant decrease by at least 10% of the measured parameter, by at least 50%, 80% or 90%, and in certain embodiments an antibody of the invention may inhibit greater than 95%, 98% or 99% of sclerostin functional activity.

The terms "cross-block", "cross-blocked" and "cross-blocking" are used interchangeably herein to mean the ability of an antibody or other binding agent to interfere with the binding of other antibodies or binding agents to sclerostin in a standard competitive binding assay.

The ability or extent to which an antibody or other binding agent is able to interfere with the binding of another antibody or binding molecule to sclerostin, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

Further details on both methods are given in the Examples.

According to the invention, a cross-blocking antibody or other binding agent according to the invention binds to sclerostin in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination.

An antibody is defined as cross-blocking in the ELISA assay as described in the Examples, if the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

Monoclonal Antibodies

Antibodies of the invention include the human monoclonal antibodies, isolated as described, in the Examples. The $V_H$ amino acid sequences of isolated antibodies of the invention are shown in SEQ ID NOs: 69-77. The $V_L$ amino acid sequences of isolated antibodies of the invention are shown in SEQ ID NOs: 80-88 respectively. The corresponding preferred full length heavy chain amino acid sequences of antibodies of the invention are shown in SEQ ID NO:113-121. The corresponding preferred full length light chain amino acid sequences of antibodies of the invention are shown in SEQ ID NO:124-132 respectively. Other antibodies of the invention include amino acids that have been mutated, yet have at least 60, 70, 80, 90 or 95 percent or more identity in the CDR regions with the CDR regions depicted in the sequences described above. In some embodiments, the invention includes mutant amino acid sequences wherein no more than 1, 2, 3, 4 or 5 amino acids have been mutated in the CDR regions when compared with the CDR regions depicted in the sequence described above.

Further, variable heavy chain parental nucleotide sequences are shown in SEQ ID NOs 89-90. Variable heavy chain parental nucleotide sequences are shown in SEQ ID NOs 100-101. Full length light chain nucleotide sequences optimized for expression in a mammalian cell are shown in SEQ ID NOs 146-154. Full length heavy chain nucleotide sequences optimized for expression in a mammalian cell are shown in SEQ ID NOs 135-143. Full length light chain amino acid sequences encoded by optimized light chain nucleotide sequences are shown in SEQ ID NOs 124-132. Full length heavy chain amino acid sequences encoded by optimized heavy chain nucleotide sequences are shown in SEQ ID NOs 113-121. Other antibodies of the invention include amino acids or nucleic acids that have been mutated, yet have at least 60, 70, 80, 90 or 95 percent or more identity to the sequences described above. In some embodiments, the invention includes mutant amino acid sequences wherein no more than 1, 2, 3, 4 or 5 amino acids have been mutated in the variable regions when compared with the variable regions depicted in the sequence described above, while retaining substantially the same therapeutic activity.

Since each of these antibodies can bind to sclerostin, the $V_H$, $V_L$, full length light chain, and full length heavy chain sequences (nucleotide sequences and amino acid sequences) can be "mixed and matched" to create other anti-sclerostin binding molecules of the invention. Sclerostin binding of such "mixed and matched" antibodies can be tested using the binding assays described above and in the Examples (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 69-77; and a light chain variable region comprising an amino acid sequence selected from the group consisting of SEQ ID NOs: 80-88; wherein the antibody specifically binds to sclerostin.

In another aspect, the invention provides:

(i) an isolated monoclonal antibody having: a full length heavy chain comprising an amino acid sequence that has been optimized for expression in the cell of a mammal selected from the group consisting of SEQ ID NOs:113-121; and a full length light chain comprising an amino acid sequence that has been optimized for expression in the cell of a mammal selected from the group consisting of SEQ ID NOs:124-132; or (ii) a functional protein comprising an antigen binding portion thereof.

In another aspect, the invention provides:

(i) an isolated monoclonal antibody having: a full length heavy chain comprising a nucleotide sequence that has been optimized for expression in the cell of a mammal selected from the group consisting of SEQ ID NOs:135-143; and a full length light chain comprising a nucleotide sequence that has been optimized for expression in the cell of a mammal selected from the group consisting of SEQ ID NOs:146-154; or, (ii) a functional protein comprising an antigen binding portion thereof.

In yet another aspect, the invention provides antibodies that comprise the heavy chain and light chain CDR1s, CDR2s and CDR3s of the antibodies, or combinations thereof. The amino acid sequences of the $V_H$ CDR1s of the antibodies are shown in SEQ ID NOs: 1-11. The amino acid sequences of the $V_H$ CDR2s of the antibodies are shown in SEQ ID NOs: 12-22. The amino acid sequences of the $V_H$ CDR3s of the antibodies are shown in SEQ ID NOs: 23-33. The amino acid sequences of the $V_L$ CDR1s of the antibodies are shown in SEQ ID NOs: 34-44. The amino acid sequences of the $V_L$ CDR2s of the antibodies are shown in SEQ ID NOs: 45-55. The amino acid sequences of the $V_L$ CDR3s of the antibodies are shown in SEQ ID NOs: 56-66. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to sclerostin and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and matched), although each antibody must contain a $V_H$ CDR1, 2 and 3 and a $V_L$ CDR1, 2 and 3 to create other anti-sclerostin binding molecules of the invention. Sclerostin binding of such "mixed and matched" antibodies can be tested using the binding assays described above and in the Examples (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

An isolated monoclonal antibody, or antigen binding region thereof has: a heavy chain variable region CDR1 comprising an amino acid sequence selected from the group consisting of SEQ ID NOs: 1-11; a heavy chain variable region CDR2 comprising an amino acid sequence selected from the group consisting of SEQ ID NOs: 12-22; a heavy chain variable region CDR3 comprising an amino acid sequence selected from the group consisting of SEQ ID NOs: 23-33; a light chain variable region CDR1 comprising an amino acid sequence selected from the group consisting of SEQ ID NOs: 34-44; a light chain variable region CDR2 comprising an amino acid sequence selected from the group consisting of SEQ ID NOs: 45-55; and a light chain variable region CDR3 comprising an amino acid sequence selected from the group consisting of SEQ ID NOs: 56-66; wherein the antibody specifically binds sclerostin.

In a certain embodiment, the antibody comprises: a heavy chain variable region CDR1 of SEQ ID NO: 3; a heavy chain variable region CDR2 of SEQ ID NO: 14; a heavy chain variable region CDR3 of SEQ ID NO: 25; a light chain variable region CDR1 of SEQ ID NO: 36; a light chain variable region CDR2 of SEQ ID NO: 47; and a light chain variable region CDR3 of SEQ ID NO: 58.

In a certain embodiment, the antibody comprises: a heavy chain variable region CDR1 of SEQ ID NO: 4; a heavy chain variable region CDR2 of SEQ ID NO: 15; a heavy chain variable region CDR3 of SEQ ID NO: 26; a light chain variable region CDR1 of SEQ ID NO: 37; a light chain variable region CDR2 of SEQ ID NO: 48; and a light chain variable region CDR3 of SEQ ID NO: 59.

In a certain embodiment, the antibody comprises: a heavy chain variable region CDR1 of SEQ ID NO: 5; a heavy chain variable region CDR2 of SEQ ID NO: 16; a heavy chain variable region CDR3 of SEQ ID NO: 27; a light chain variable region CDR1 of SEQ ID NO: 38; a light chain variable region CDR2 of SEQ ID NO: 49; and a light chain variable region CDR3 of SEQ ID NO: 60.

In a certain embodiment, the antibody comprises: a heavy chain variable region CDR1 of SEQ ID NO: 6; a heavy chain variable region CDR2 of SEQ ID NO: 17; a heavy chain variable region CDR3 of SEQ ID NO: 28; a light chain variable region CDR1 of SEQ ID NO: 39; a light chain variable region CDR2 of SEQ ID NO: 50; and a light chain variable region CDR3 of SEQ ID NO: 61.

In a certain embodiment, the antibody comprises: a heavy chain variable region CDR1 of SEQ ID NO: 7; a heavy chain variable region CDR2 of SEQ ID NO: 18; a heavy chain variable region CDR3 of SEQ ID NO: 29; a light chain variable region CDR1 of SEQ ID NO: 40; a light chain variable region CDR2 of SEQ ID NO: 51; and a light chain variable region CDR3 of SEQ ID NO: 62.

In a certain embodiment, the antibody comprises: a heavy chain variable region CDR1 of SEQ ID NO: 8; a heavy chain variable region CDR2 of SEQ ID NO: 19; a heavy chain variable region CDR3 of SEQ ID NO: 30; a light chain variable region CDR1 of SEQ ID NO: 41; a light chain variable region CDR2 of SEQ ID NO: 52; and a light chain variable region CDR3 of SEQ ID NO: 63.

In a certain embodiment, the antibody comprises: a heavy chain variable region CDR1 of SEQ ID NO: 9; a heavy chain variable region CDR2 of SEQ ID NO: 20; a heavy chain variable region CDR3 of SEQ ID NO: 31; a light chain variable region CDR1 of SEQ ID NO: 42; a light chain variable region CDR2 of SEQ ID NO: 53; and a light chain variable region CDR3 of SEQ ID NO: 64.

In a certain embodiment, the antibody comprises: a heavy chain variable region CDR1 of SEQ ID NO: 10; a heavy chain variable region CDR2 of SEQ ID NO: 21; a heavy chain variable region CDR3 of SEQ ID NO: 32; a light chain variable region CDR1 of SEQ ID NO: 43; a light chain variable region CDR2 of SEQ ID NO: 54; and a light chain variable region CDR3 of SEQ ID NO: 65.

In a certain embodiment, the antibody comprises: a heavy chain variable region CDR1 of SEQ ID NO: 11; a heavy chain variable region CDR2 of SEQ ID NO: 22; a heavy chain variable region CDR3 of SEQ ID NO: 33; a light chain variable region CDR1 of SEQ ID NO: 44; a light chain variable region CDR2 of SEQ ID NO: 55; and a light chain variable region CDR3 of SEQ ID NO: 66.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene. In some embodiments, germline immunoglobulin amino acid sequences are selected from those comprising the variable heavy chain sequences consisting of SEQ ID NO:67-68 respectively, and the variable light chain sequences consisting of SEQ ID NO:78-79 respectively.

Homologous Antibodies

In yet another embodiment, an antibody of the invention has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-sclerostin antibodies of the Invention.

For example, the invention provides an isolated monoclonal antibody (or a functional protein comprising an antigen binding portion thereof) comprising a heavy chain variable region and a light chain variable region, wherein: the heavy chain variable region comprises an amino acid sequence that is at least 80% identical to an amino acid sequence selected from the group consisting of SEQ ID NOs: 67-77; the light chain variable region comprises an amino acid sequence that is at least 80% identical to an amino acid sequence selected from the group consisting of SEQ ID NOs: 78-88; the antibody specifically binds to sclerostin, and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

In a further example, the invention provides an isolated monoclonal antibody, (or a functional protein comprising an antigen binding portion thereof) comprising a full length heavy chain and a full length light chain, wherein: the full length heavy chain comprises an amino acid sequence that is at least 80% identical to an amino acid sequence selected from the group consisting of SEQ ID NOs 111-121; the full length light chain comprises an amino acid sequence that is at least 80% identical to an amino acid sequence selected from the group consisting of SEQ ID NOs 122-132; the antibody specifically binds to sclerostin, and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

In another example, the invention provides an isolated monoclonal antibody (or a functional protein comprising an antigen binding portion thereof), comprising a full length heavy chain and a full length light chain, wherein: the full length heavy chain is encoded by a nucleotide sequence that is at least 80% identical to a nucleotide sequence selected from the group consisting of SEQ ID NOs 133-143; the full length light chain comprises a nucleotide sequence that is at least 80% identical to a nucleotide sequence selected from the group consisting of SEQ ID NOs 144-154; the antibody specifically binds to sclerostin, and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

In various embodiments, the antibody may exhibit one or more, two or more, or three of the functional properties discussed above. The antibody can be, for example, a human antibody, a humanized antibody or a chimeric antibody.

In other embodiments, the $V_H$ and/or $V_L$ amino acid sequences may be 50%, 60%, 70%, 80%, 90%, 95%, 96%, 97%, 98% or 99% identical to the sequences set forth above. In other embodiments, the $V_H$ and/or $V_L$ amino acid sequences may be identical except an amino acid substitution in no more than 1, 2, 3, 4 or 5 amino acid position(s). An antibody having $V_H$ and $V_L$ regions having high (i.e., 80% or greater) identity to the $V_H$ and $V_L$ regions of SEQ ID NOs 67-77 and SEQ ID NOs 78-88 respectively, can be obtained by mutagenesis (e.g., site-directed or PCR-mediated mutagenesis) of nucleic acid molecules encoding SEQ ID NOs: 89-99 and 100-110 respectively, followed by testing of the encoded altered antibody for retained function (i.e., the functions set forth above) using the functional assays described herein.

In other embodiments, the full length heavy chain and/or full length light chain amino acid sequences may be 50%, 60%, 70%, 80%, 90%, 95%, 96%, 97%, 98% or 99% identical to the sequences set forth above. An antibody having a full length heavy chain and full length light chain having high (i.e., 80% or greater) identity to the full length heavy chains of any of SEQ ID NOs 111-121 and full length light chains of any of SEQ ID NOs 122-132 respectively, can be obtained by mutagenesis (e.g., site-directed or PCR-mediated mutagenesis) of nucleic acid molecules encoding SEQ ID NOs 133-143 and SEQ ID NOs 144-154 respectively, followed by testing of the encoded altered antibody for retained function (i.e., the functions set forth above) using the functional assays described herein.

In other embodiments, the full length heavy chain and/or full length light chain nucleotide sequences may be 60%, 70%, 80%, 90%, 95%, 96%, 97%, 98% or 99% identical to the sequences set forth above.

In other embodiments, the variable regions of heavy chain and/or light chain nucleotide sequences may be 60%, 70%, 80%, 90%, 95%, 96%, 97%, 98% or 99% identical to the sequences set forth above As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used. See http:www.ncbi.nhn.nih.gov.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the anti-sclerostin antibodies of the invention. Accordingly, the invention provides an isolated monoclonal antibody, or a functional protein comprising an antigen binding portion thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs:1-11, and conservative modifications thereof; the heavy chain variable region CDR2 amino acid sequences are selected from the group consisting of SEQ ID NOs: 12-22, and conservative modifications thereof; the heavy chain variable region CDR3 amino acid sequences are selected from the group consisting of SEQ ID NOs: 23-33, and conservative modifications thereof; the light chain variable regions CDR1 amino acid sequences are selected from the group consisting of SEQ ID NOs: 34-44, and conservative modifications thereof; the light chain variable regions CDR2 amino acid sequences are selected from the group consisting of SEQ ID NOs: 45-55, and conservative modifications thereof; the light chain variable regions of CDR3 amino acid sequences are selected from the group consisting of SEQ ID NOs: 56-66, and conservative modifications thereof; the antibody specifically binds to sclerostin, and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

In various embodiments, the antibody may exhibit one or more, two or more, or three or more of the functional properties listed discussed above. Such antibodies can be, for example, human antibodies, humanized antibodies or chimeric antibodies.

In other embodiments, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-sclerostin antibodies of the invention. Accordingly, the invention provides an isolated monoclonal antibody optimized for expression in a mammalian cell consisting of a full length heavy chain and a full length light chain wherein: the full length heavy chain has amino acid sequences selected from the group of SEQ ID NOs: 111-121, and conservative modifications thereof; and the full length light chain has amino acid sequences selected from the group of SEQ ID NOs: 122-132, and conservative modifications thereof; the antibody specifically binds to sclerostin; and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

In various embodiments, the antibody may exhibit one or more, two or more, or three or more of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Anti-Sclerostin Antibodies of the Invention In another embodiment, the invention provides antibodies that bind to the same epitope as do the various specific anti-sclerostin antibodies of the invention described herein.

It has indeed been surprisingly found that all the antibodies described in the Examples that are capable of:
(i) blocking the inhibitory effect of sclerostin in a cell based wnt signaling assay;
(ii) blocking the inhibitory effect in a cell based mineralization assay;
(iii) inhibiting binding of sclerostin to the LRP-6; and,
(iv) increasing bone formation, mass and density,
bind the same epitope in sclerostin with high affinity, said epitope being a conformational epitope that include amino acids from both SEQ ID NO:156 and SEQ ID NO:157. Without being bound by any specific model, it is proposed here that the amino acid sequences SEQ ID NO:156 and SEQ ID NO:157 delineate one conformational epitope region in the sclerostin polypeptide that is recognized by the antibodies of the invention.

Additional antibodies can therefore be identified based on their ability to cross-compete (e.g., to competitively inhibit the binding of, in a statistically significant manner) with other antibodies of the invention in standard sclerostin binding assays. The ability of a test antibody to inhibit the binding of antibodies of the present invention to human sclerostin demonstrates that the test antibody can compete with that antibody for binding to human sclerostin; such an antibody may, according to non-limiting theory, bind to the same or a related (e.g., a structurally similar or spatially proximal) epitope on human sclerostin as the antibody with which it competes. In a certain embodiment, the antibody that binds to the same epitope on human sclerostin as the antibodies of the present invention is a human monoclonal antibody. Such human monoclonal antibodies can be prepared and isolated as described in the Examples.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or a functional protein comprising an antigen binding portion thereof, comprising a heavy chain variable region comprising CDR1 sequences having an amino acid sequence selected from the group consisting of SEQ ID NOs: 1-11; CDR2 sequences having an amino acid sequence selected from the group consisting of SEQ ID NOs: 12-22; CDR3 sequences having an amino acid sequence selected from the group consisting of SEQ ID NOs: 23-33, respectively; and a light chain variable region having CDR1 sequences having an amino acid sequence selected from the group consisting of SEQ ID NOs: 34-44; CDR2 sequences having an amino acid sequence selected from the group consisting of SEQ ID NOs: 45-55; and CDR3 sequences consisting of an amino acid sequence selected from the group consisting of SEQ ID NOs: 56-66, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J. Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated anti-sclerostin monoclonal antibodies, or a functional protein comprising an antigen binding portion thereof, consisting of a heavy chain variable region having: a $V_H$ CDR1 region consisting of an amino acid sequence selected from the group having SEQ ID NOs: 1-11 or an amino acid sequence having one, two, three, four or five amino acid substitutions, deletions or additions as compared to SEQ ID NOs: 1-11; a $V_H$ CDR2 region having an amino acid sequence selected from the group consisting of SEQ ID NOs: 12-22, or an amino acid sequence having one, two, three, four or five amino acid substitutions, deletions or additions as compared to SEQ ID NOs: 12-22; a $V_H$ CDR3 region having an amino acid sequence selected from the group consisting of SEQ ID NOs: 23-33, or an amino acid sequence having one, two, three, four or five amino acid substitutions, deletions or additions as compared to SEQ ID NOs: 23-33; a $V_L$ CDR1 region having an amino acid sequence selected from the group consisting of SEQ ID NOs: 34-44, or an amino acid sequence having one, two, three, four or five amino acid substitutions, deletions or additions as compared to SEQ ID NOs: 34-44; a $V_L$ CDR2 region having an amino acid sequence selected from the group consisting of SEQ ID NOs: 45-55, or an amino acid sequence having one, two, three, four or five amino acid substitutions, deletions or additions as compared to SEQ ID NOs: 45-55; and a $V_L$ CDR3 region having an amino acid sequence selected from the group consisting of SEQ ID NOs: 56-66, or an amino acid sequence having one, two, three, four or five amino acid substitutions, deletions or additions as compared to SEQ ID NOs: 56-66.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to sclerostin. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO: 155. Such compounds are known herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (*Camelus bactrianus* and *Camelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for sclerostin. In certain embodiments herein, the camelid antibody or nanobody is naturally produced in the camelid animal, i.e., is produced by the camelid following immunization with sclerostin or a peptide fragment thereof, using techniques described herein for other antibodies. Alternatively, the anti-sclerostin camelid nanobody is engineered, i.e., produced by selection for example from a library of phage displaying appropriately mutagenized camelid nanobody proteins using panning procedures with sclerostin as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214 (WO94/04678).

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (SciI Proteins GmbH, Halle, Germany), protein epitope mimetics (Polyphor Ltd, Allschwil, Switzerland).

(i) Adnectins—Compound Therapeutics

The adnectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris brassicae* has been used to develop anticalins by mutagenizing the set of four loops. One example of a patent application describing "anticalins" is PCT WO199916873.

(vi) Affilin—SciI Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. SciI Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions. More generally, any polypeptide that mimics the 3D structure of the epitope of the disclosed antibodies are part of the present invention. Preferred embodiments are polypeptides of 30-100 amino acids comprising at least the following polypeptides E1-L-E2, wherein E1 is SEQ ID NO:156 and E2 is SEQ ID NO:157 and L is an polypeptidic linker allowing E1 and E2 to reproduce the 3D structure of the region recognized by the antibodies of the invention. According to a preferred embodiment, L is a linker consisting of 10-20 amino acids selected among glycine or serine amino acids. Preferably the linker L comprises the peptide GGGSGGGGSGGGG (SEQ ID NO: X/SEQ ID NO: 158) or GGGGSGGGGSGGGGSGGGG (SEQ ID NO:Y/SEQ ID NO: 159), more preferably the linker L is consisting essentially of SEQ ID NO: X or SEQ ID NO:Y.

These polypeptides should retain high affinity to the antibodies of the invention. These polypeptides can also be advantageously used as immunogens to raise antibodies against sclerostin.

These polypeptides can also be used as antagonist or agonist of sclerostin and therefore have similar applications as those described for the antibodies of the present invention.

Polypeptides with one or more amino acid substitutions or deletions, preferably not less than 1, 2 or 3 amino acid substitutions, or deletions in E1 and/or E2 sequence, are also part of the invention. These polypeptides may further be engineered to increase half life or improve solubility. Especially, fusion constructs of these polypeptides with serum proteins, such as Fc fragments of IgG or human serum albumin can be generated to increase half life, similarly to Fc engineering described in the following paragraph for antibody fragment molecules of the invention.

Framework or Fc Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be, engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter at al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the invention is pegylation. An antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono(C1-C10)alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al., and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Methods of Engineering Altered Antibodies

As discussed above, the anti-sclerostin antibodies having $V_H$ and $V_L$ sequences or full length heavy and light chain sequences shown herein can be used to create new anti-sclerostin antibodies by modifying full length heavy chain and/or light chain sequences, $V_H$ and/or $V_L$ sequences, or the constant region(s) attached thereto. Thus, in another aspect of the invention, the structural features of an anti-sclerostin antibody of the invention are used to create structurally related anti-sclerostin antibodies that retain at least one functional property of the antibodies of the invention, such as binding to human sclerostin and also inhibiting one or more functional properties of sclerostin (e.g., receptor binding, preventing or ameliorating osteolysis).

For example, one or more CDR regions of the antibodies of the present invention, or mutations thereof, can be combined recombinantly with known framework regions and/or other CDRs to create additional, recombinantly-engineered, anti-sclerostin antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-sclerostin antibody consisting of: a heavy chain variable region antibody sequence having a CDR1 sequence selected from the group consisting of SEQ ID NOs: 1-11, a CDR2 sequence selected from the group consisting of SEQ ID NOs: 12-22 and/or a CDR3 sequence selected from the group consisting of SEQ ID NOs: 23-33; and a light chain variable region antibody sequence having a CDR1 sequence selected from the group consisting of SEQ ID NOs: 34-44, a CDR2 sequence selected from the group consisting of SEQ ID NOs: 45-55 and/or a CDR3 sequence selected from the group consisting of SEQ ID NOs: 56-66; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing an anti-sclerostin antibody optimized for expression in a mammalian cell consisting of: a full length heavy chain antibody sequence having a sequence selected from the group of SEQ ID NOs: 111-121; and a full length light chain antibody sequence having a sequence selected from the group of 122-132; altering at least one amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having fixed CDR3 sequences selected among the group consisting of SEQ ID NO:23-33 or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the anti-sclerostin antibodies described herein, which functional properties include, but are not limited to, specifically binding to human sclerostin; and the antibody exhibits at least one of the following functional properties: the antibody blocks the inhibitory effect of sclerostin in a cell based wnt signaling assay, the antibody blocks the inhibitory effect of sclerostin in a cell based mineralization assay or blocks the inhibitory effect of sclerostin in Smad1 phosphorylation assay or the antibody inhibits binding of sclerostin to the LRP-6 or the antibody increases bone formation and mass and density.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-sclerostin antibody coding sequence and the resulting modified anti-sclerostin antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. Examples of full length light chain parental nucleotide sequences are shown in SEQ ID NOs 144-145. Examples of full length heavy chain parental nucleotide sequences are shown in SEQ ID NOs 133-134. Examples of full length light chain nucleotide sequences optimized for expression in a mammalian cell are shown in SEQ ID NOs: 146-154. Examples of full length heavy chain nucleotide sequences optimized for expression in a mammalian cell are shown in SEQ ID NOs: 135-143.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. Preferably, the heavy chain constant region is selected among IgG2 isotypes. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against sclerostin can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or K, and in response to immunization, the introduced human heavy and light chain transgenes undergo class switching and somatic mutation to generate high affinity human IgGκ (monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon at al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/103918, WO 93/12227, WO 94/25585, WO 97/113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-sclerostin antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114, 598; 6,150,584 and 6,162,963 to Kucherlapati et al.

Moreover, alternative transchromosomic animal systems expressing human immunoglobulin genes are available in the art and can be used to raise anti-sclerostin antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-sclerostin antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-

Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/all penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Bispecific Molecules

In another aspect, the present invention features bispecific or multispecific molecules comprising an anti-sclerostin antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for sclerostin and a second binding specificity for a second target epitope. For example, the second target epitope is another epitope of sclerostin different from the first target epitope. Another example is a bispecific molecule comprising at least one first binding specificity for sclerostin and a second binding specificity for an epitope within Dkk-1. Another example is a bispecific molecule comprising at least one first binding specificity for sclerostin and a second binding specificity for an epitope within LRP4.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83, and Glennie et al., 1987 J. Immunol. 139: 2367-2375. Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013, 653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present invention provides multivalent compounds comprising at least two identical or different antigen-binding portions of the antibodies of the invention binding to sclerostin. Preferably, given the trimeric nature of sclerostin, the compounds of the invention provides at least three or four antigen-binding portions of the antibodies. The antigen-binding portions can be linked together via protein fusion or covalent or non covalent linkage. Alternatively, methods of linkage has been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Pharmaceutical Compositions

In another aspect, the present invention provides a composition, e.g., a pharmaceutical composition, containing one or a combination of monoclonal antibodies, or antigen-binding region(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies that bind to different epitopes on the target antigen or that have complementary activities.

Pharmaceutical compositions of the invention also can be administered in combination therapy, i.e., combined with other agents. For example, the combination therapy can include an anti-sclerostin antibody of the present invention combined with at least one other anti-inflammatory or anti-osteoporotic agent. Examples of therapeutic agents that can be used in combination therapy are described in greater detail below in the section on uses of the antibodies of the invention. The compositions are preferably formulated at physiological pH.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-sclerostin antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously or sequentially, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-sclerostin antibody of the invention can result in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. No. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

Uses and Methods of the Invention

The antibodies of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein is intended to include human and non-human animals. Non-human animals includes all vertebrates, e.g., mammals and non-mammals, such as non-human primates, sheep, dogs, cats, cows, horses, chickens, amphibians, and reptiles.

The methods are particularly suitable for treating, preventing or diagnosing sclerostin-related disorders and/or aberrant bone mineral density disorders, e.g., osteoporosis.

The invention also provides methods for increasing the mineral content and/or mineral density of bone. Compositions of the present invention may also be useful for improving outcomes in orthopedic procedures, dental procedures, implant surgery, joint replacement, bone grafting, bone cosmetic surgery and bone repair such as fracture healing, non-union healing, delayed union healing and facial reconstruction. One or more compositions may be administered before, during and/or after the procedure, replacement, graft, surgery or repair.

As used herein, "a sclerostin-related disorder" includes disorders in which bone mineral density (BMD) is abnormally and/or pathologically low relative to healthy subjects. Disorders characterized by low BMD and/or bone fragility include but are not limited to primary and secondary osteoporosis, osteopenia, osteomalacia, osteogenesis imperfecta (OI), avascular necrosis (osteonecrosis), fractures and implant healing (dental implants and hip implants), bone loss due to other disorders (e.g., associated with HIV infection, cancers, or arthritis). Other "sclerostin-related disorders" include but are not limited to rheumatoid arthritis, osteoarthritis, arthritis, and the formation and/or presence of osteolytic lesions.

As used herein, "a sclerostin-related disorder" includes conditions associated with or characterized by aberrant sclerostin levels. These include cancers and osteoporotic conditions (e.g., osteoporosis or osteopenia), some of which overlap with "sclerostin-related disorders" as defined herein. Sclerostin-related cancers can include myeloma (e.g., multiple myeloma with osteolytic lesions), breast cancer, colon cancer, melanoma, hepatocellular cancer, epithelial cancer, esophageal cancer, brain cancer, lung cancer, prostate cancer, or pancreatic cancer, as well as any metastases thereof.

A "sclerostin-related disorder" can also include renal and cardiovascular conditions, due at least to sclerostin's expression in the kidney and cardiovasculature. Said disorders include but are not limited to such renal disorders as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, polycystic kidney disease, neoplasia, sickle cell disease, and chronic inflammatory diseases), tubular diseases (e.g., acute tubular necrosis and acute renal failure, polycystic renal diseasemedullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, gout, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

Said disorders also include but are not limited to such cardiovascular disorders as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cariomyopathy).

When antibodies to sclerostin are administered together with another agent, the two can be administered in either order (i.e. sequentially) or simultaneously.

According to a further embodiment of the invention, the antibodies of the invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, calcilytics, calcimimetics (e.g., cinacalcet), a steroid hormone, e.g. an estrogen, a partial estrogen agonist or estrogen-gestagen combination, a SERM (Selective Estrogen Receptor Modulator) e.g. raloxifene, lasofoxifene, bazedoxifene, arzoxifene, FC1271, Tibolone (Livial®), a SARM (Selective Androgen Receptor Modulator), a RANKL antibody (such as denosumab), a cathepsin K inhibitor, vitamin D or an analogue thereof or PTH, a PTH fragment or a PTH derivative e.g. PTH (1-84) (such as Preos™), PTH (1-34) (such as Forteo™), PTH (1-36), PTH (1-38), PTH (1-31)NH2 or PTS 893. According to another embodiment, the antibodies of the invention may be employed in combination with other current osteoporosis therapy approaches, including bisphosphonates (e.g., Fosamax™ (alendronate), Actonel™ (risedronate sodium), Bonviva™ (ibandronic acid), Zometa™ (zoledronic acid), Aclasta™/Reclast™ (zoledronic acid), olpadronate, neridronate, skelid, bonefos), statins, anabolic steroids, lanthanum and strontium salts, and sodium fluoride.

In one specific embodiment, the antibodies of the invention may be administered in combination with an LRP4 modulating agent, i.e., an agent modulating the expression or activity of LRP4, e.g., an LRP4 neutralizing antibody.

In another specific embodiment, the antibodies of the invention may be administered in combination with a DKK1 modulating agent, i.e., an agent that interfere or neutralize Dkk-1 mediated antagonism of Wnt signaling, e.g., a DKK1 neutralizing antibody.

Thus, the invention also provides the use of an antibody or functional protein of the invention and (i) zoledronic acid, (ii) an anti-DKK1 antibody, (iii) alendronate, (iv) an anti-LRP4 antibody, (v) hPTH and/or (vi) parathyroid hormone releasing agents (calcilytics), in the manufacture of a medicament for the treatment of a pathological disorder that is mediated by sclerostin or that is associated with an increased level of sclerostin.

In another embodiment, the invention provides the use of an antibody or functional protein of the invention in the manufacture of a medicament for the treatment of a pathological disorder that is mediated by sclerostin or that is associated with an increased level of sclerostin, wherein the medicament is used in conjunction with (i) zoledronic acid, (ii) an anti-DKK1 antibody, (iii) alendronate, (iv) an anti-LRP4 antibody, (v) hPTH and/or (vi) parathyroid hormone releasing agents (calcilytics).

In another embodiment, the invention provides the use of (i) zoledronic acid, (ii) an anti-DKK1 antibody, (iii) alendronate, (iv) an anti-LRP4 antibody, (v) hPTH and/or (vi) parathyroid hormone releasing agents (calcilytics), in the manufacture of a medicament for the treatment of a pathological disorder that is mediated by sclerostin or that is associated with an increased level of sclerostin, wherein the medicament is used in conjunction with an antibody or functional protein of the invention.

In another embodiment, the invention provides the use of an antibody or functional protein of the invention in the manufacture of a medicament for the treatment of a pathological disorder that is mediated by sclerostin or that is associated with an increased level of sclerostin, wherein the patient has been pre-administered with (i) zoledronic acid, (ii) an anti-DKK1 antibody, (iii) alendronate, (iv) an anti-LRP4 antibody, (v) hPTH and/or (vi) parathyroid hormone releasing agents (calcilytics).

In another embodiment, the invention provides the use of (i) zoledronic acid, (ii) an anti-DKK1 antibody, (iii) alendronate, (iv) an anti-LRP4 antibody, (v) hPTH and/or (vi) parathyroid hormone releasing agents (calcilytics), in the manufacture of a medicament for the treatment of a pathological disorder that is mediated by sclerostin or that is associated with an increased level of sclerostin, wherein the patient has been pre-administered with an antibody or functional protein of the invention.

In one embodiment of the combinations recited above, the hPTH is hPTH(1-34).

In one embodiment, the antibodies of the invention can be used to detect levels of sclerostin, or levels of cells that contain sclerostin. This can be achieved, for example, by contacting a sample (such as an in vitro sample) and a control sample with the anti-sclerostin antibody under conditions that allow for the formation of a complex between the antibody and sclerostin. Any complexes formed between the antibody and sclerostin are detected and compared in the sample and the control. For example, standard detection methods, well known in the art, such as ELISA and flow cytometic assays, can be performed using the compositions of the invention.

Accordingly, in one aspect, the invention further provides methods for detecting the presence of sclerostin (e.g., human sclerostin antigen) in a sample, or measuring the amount of sclerostin, comprising contacting the sample, and a control sample, with an antibody of the invention, or an antigen binding region thereof, which specifically binds to sclerostin, under, conditions that allow for formation of a complex between the antibody or portion thereof and sclerostin. The formation of a complex is then detected, wherein a difference in complex formation between the sample compared to the control sample is indicative of the presence of sclerostin in the sample.

Also within the scope of the invention are kits consisting of the compositions (e.g., antibodies, human antibodies and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). For example, such kits may comprise an antibody or functional protein of the invention and one or more of (i) zoledronic acid, (ii) an anti-DKK1 antibody, (iii) alendronate, (iv) an anti-LRP4 antibody, (v) hPTH and (vi) parathyroid hormone releasing agents (calcilytics). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Functional Assays

Alkaline Phosphatase Assay (ALP)
Cells
  MC3T31b cells is a clone of MC3T3-JP cells expressing OSE2-luc. This clone was obtained after stable transfection of MC3T3-JP (MC3T3-E1 mouse osteoblast, Japan clone, Jp; a kind gift of Dr. T. Kokkubo, Novartis, Japan) using 8x-OSE2 wt-mOG2luc in pcDNA3.1+.
Culture Medium
  MC3T3-1b cells were routinely cultivated in minimum essential medium alpha (MEMα; Invitrogen, Cat#22561-021) supplemented with 10% fetal calf serum (FCS; Amimed Cat#2-01F100-I), 2 mM L-glutamine (Gibco Cat#25030-024), 50 IU penicillin/50 µg/ml streptomycin (Amimed Cat#4-01F00-H) and 10 mM Hepes (Gibco Cat#15630-056) and 0.75 mg/ml G418 (Gibco Cat#10131-027) (maintenance culture medium).
Stock Solutions
  Ten mM ascorbic acid (Wako Pure Chemical Cat#013-12061) in DMEM-LG, 14 nM BMP-2 (R&D Cat#355-BM-010) in 5 mM acetic acid and 0.1% bovine serum albumine (BSA, Sigma Cat#A-8806); 1 M β-glycerophosphate (Sigma Cat#G9891) in Tyrode solution; Tyrode solution: 9.72 g Tyrode's salt (Sigma Cat#T2145) and 1 g $NaHCO_3$ in 1 L $H_2O$, ALP substrate buffer: 25 mM glycine and 0.5 mM MgCL2, pH 10.5; ALP substrate solution: 5 mg p-nitrophenyl phosphate (Sigma 104 substrate, Sigma Cat#50942-

200TAB) in 3.75 ml ALP substrate buffer, pH 10.5; 1 mM p-nitrophenyl (Sigma Cat#104-1) in ALP substrate solution.
Assay For the ALP assays, MC3T3 1b cells were grown in assay culture medium (corresponding to the maintenance culture medium in the absence of G418). MC3T31b were seeded in 200 µl at $3\times10^4$ cells/ml if induction started 72 h later or $2\times10^4$ cells/ml if induction, started 96 h later. The plates were incubated for 72 h or 96 h at 37° C. and 5% $CO_2$, before the induction was started using complete medium (by supplementing the culture medium with 10 mM b-glycero-phosphate (bGP) and 50 µM ascorbic acid (AA)). The antibodies to be tested were diluted with complete medium. The antibody together with BMP-2 (0.7 nM) and sclerostin (50 nM) were added to the wells (triplicate) in a final volume of 200 µl complete medium. On each plate, 4 internal controls were included in triplicate: a solvent control (BSA), BMP-2 control (0.7 nM), BMP-2+sclerostin (BMP-2 (0.7 nM) and sclerostin (50 nM)) and a sclerostin control (50 nM). The plates were incubated for another 72 h at 37° C. and 5% $CO_2$. At the end of the induction period, the assay was terminated by removing the medium and adding 150 µl ALP substrate solution (freshly prepared) to each well. The plates were incubated for 3-30 min. One hundred µl of 1M NaOH was added to stop the reaction and the plates were shaken on a Plate-shaker. OD was red against a blank at 405 nm and ALP activity was calculated in nmol/min. Fifty nM sclerostin was used to get at least 70% inhibition of BMP-2 induced ALP production [0.7 nM BMP-2].
WNT-Assay This assay was established for testing antibodies based on the ability of sclerostin to inhibit Wnt1-mediated induction of STF reporter gene.
Transfection of HEK293 Cells On day 1, HEK293 cells were seeded at $1.3$-$1.4\times10^5$ cells per well (in 0.5 ml volume) of a 24-well poly-D-lysine plate (BD-BioCoat #356414) in DMEM (Gibco, Cat#61965-026) containing 10% fetal calf serum (FCS), 1% L-glutamine (Gibco, Cat #25030.024), 1% non essential amino acids (Gibco, cat #11140) without antibiotics. Transfection was performed on day 2 with Lipofectamine 2000 (Invitrogen, Cat#11668-019). For each well to be transfected, the following amount of plasmids was added to a final volume of 50 µl OptiMEM®I (Gibco, Cat#31985-047): for control wells (pcDNA3+, 480 ng; SuperTopFlash (STF) 20 ng; phRL-CMV, 0.5 ng) and for Wnt1 treatment wells (pcDNA-wnt1, 20 ng; pcDNA3+, 460 ng; SuperTopFlash (STF) 20 ng; phRL-CMV, 0.5 ng).

In a second tube, 1.6 µl of Lipofectamine 2000 was diluted into 50 µl of OptiMEM®I and incubated at room temperature for 5 minutes. The contents of the two tubes were then mixed by adding the content of the lipid tube to the DNA tube and incubated for 30 minutes at room temperature to allow DNA-lipid complex formation. The DNA-lipid complex (100 µl) was then evenly added to wells and incubated at 37° C. in 5% $CO_2$ for 5 hours. At the end of the 5-hour incubation, cells were ready for treatment with testing reagents such as SOST, antibodies etc.
Establish SOST-Dose Dependent Inhibition To establish the dose inhibition curve, a series of two-fold dilutions of rhSOST in DMEM containing 10% FCS, 1% L-glutamine and 1% non essential amino acids without antibiotics were prepared, starting at 160 nM. The concentration of stock rhSOST was 260 µg/ml in DMEM with 1% FCS. Routinely, each condition was tested in duplicates. Therefore, 1 ml of medium for each condition was prepared and 450 µl was added per well after removing medium containing transfection mix from wells. The treatment time was 18-20 hours. At the end of the incubation, luciferase assay was performed as outlined below.
Test of Anti-SOST Antibodies Antibodies were premixed with SOST before adding to the cells. For this purpose, a DMEM medium (10% FCS, 1% L-glutamine and 1% non essential amino acids without antibiotics) with 20 to 30 nM of rhSOST was prepared. Then, different dilutions of tested antibodies were added to the SOST containing medium according the experimental design. These mixes were prepared 40 minutes before the treatment. Each condition was routinely tested in duplicates. To do so, 1 ml of medium for each condition was prepared and 450 µl was added per well after removing medium containing transfection mix from wells. The treatment time was 18-20 hours. At the end of the incubation, luciferase assay was performed as outlined below.
Luciferase Assay At the end of the incubation, medium was removed, and 300 µl of 1× Passive Lysis Buffer (Promega, Cat#E194A) was added to lyse cells. Luciferase activity was then measured using Dual-Glo Luciferase System (Promega, Cat#E2940) with 30 µl of lysates in duplicates. The assay was performed according to the instruction booklet provided with the kit. Typically, 30 µl of Dual-Glo luciferase (firefly luciferase; for STF) and 30 µl of Dual-Glo Stop and Glo (Renilla luciferase; for transfection efficiency control) substrates were used. Luminescent signals were measured with Mithras LB940 instrument (Berthold Technologies).
Data Calculation The ratio of firefly to Renilla luciferases was calculated. The final results are expressed by setting the value of Wnt1 without SOST as 1.
Mineralization Assay
Cells MC3T3 1b cells is a clone of MC3T3-JP cells expressing OSE2-luc. This clone was obtained after stable transfection of MC3T3-JP (MC3T3-E1 mouse osteoblast, Japan clone, Jp; a kind gift of Dr. T. Kokkubo, Novartis, Japan) using 8x-OSE2 wt-mOG2luc in pcDNA3.1+.
Culture Medium MC3T3-1b cells were routinely cultivated in minimum essential medium alpha (MEMα; Invitrogen, Cat#22561-021) supplemented with 10% fetal calf serum (FCS; Amimed Cat#2-01F100-1), 2 mM L-glutamine (Gibco Cat#25030-024), 50 IU penicillin/50 µg/ml streptomycin (Amimed Cat#4-01F00-H) and 10 mM Hepes (Gibco Cat#15630-056) and 0.75 mg/ml G418 (Gibco Cat#10131-027) (maintenance culture medium).
Mineralization Assay Matrix-associated calcium deposited in wells was determined in MC3T3-1b cells using the Calcium kit (Axon Lab, Cat#AXON0012). Cells were seeded at $6\times10^3$ cells/well or $2\times10^3$ cells/well to improve cell responsiveness in 96-well plates in 1000 assay culture medium (maintenance culture medium without G418) and incubated for 3 days to reach confluence. Assay culture medium was then changed and compounds to be tested added together with 10 mM b-glycero-phosphate (bGP; Sigma Cat#G9891) and 50 µM ascorbic acid (AA; Wako Pure Chemical Cat#013-12061). Prior to their addition to the cells, sclerostin and the Fabs to be tested were pre-incubated in a separate plate for 2 h at room temperature; meanwhile the assay 96 well-plates were given 2.1 or 2.8 nM BMP-2 (R&D Systems, Cat#355-BM-010) before receiving the sclerostin-Fab mix. Cells were incubated for 14 days and assay medium was replaced every 3-4 days. Briefly, at the end of the incubation, cells were washed twice with 200

μl PBS/well, 50 μl of 0.5 M HCl was added in each well and plates were frozen down at −20° C. for minimum 24 h. At the appropriate time, plates were thawed at room temperature for 2 hours and 10 μl of each well was transferred in a new 96-well plate. Calcium Working Solution (1:5) was then added (200 μl) and 5-30 minutes later, plates were read at 595 nm on a microplate reader.

The absorbance was translated into μg of calcium according to a standard curve, control well (ascorbic acid and beta-glycerophosphate) value was subtracted from each data well and final results were expressed as % of BMP-2-induced mineralization.

SMAD1 Phosphorylation Western
Material
MC3T3-E1 mouse osteoblast, (Japan clone, kind gift of Dr. T. Kokkubo, Novartis, Japan)
C3H10T1/2 cells (mouse embryo mesenchymal; ATCC, Cat.Nb.: CCL-226)
SCL non-glycosylated, E. coli derived (Novartis, PSU5257)
15N SCL non-glycosylated, E. coli derived (Novartis, PSU11274)
hSOST-APP, glycosylated, HEK-EBNA derived (Novartis, BTP11100)
rhSCL, glycosylated, mouse myeloma cells derived (R&D Systems, Cat.Nb.: 1406-ST/CF)
anti hSOST antibody (R&D Systems, Cat.Nb.: AF1406)
PhosphoSafe Extraction Reagent (Novagen, Cat. Nb.: 71296-3)
Protease Inhibitor Cocktail Set III (Calbiochem, Cat. Nb.: 539134)
NuPAGE Novex Tris-Acetate Gel 7% 1.5 mm, 15 wells (Invitrogen, Cat. Nb.: EA03585)
Tris-Acetate SDS Running Buffer 20× (Invitrogen, Cat. Nb.: LA0041)
NuPAGE Antioxidant (Invitrogen, Cat. Nb.: NP0005)
Immobilon-P Transfer Membrane 0.45 um (Millipore, Cat. Nb.: IPVH00010)
Wattman chromatography paper (Merck, Cat. Nb.: 3587600)
XCell SureLock Mini-Cell and XCell II Blot Module (Invitrogen)
VersaMax microplate reader (Bucher)

Cell Culture and Extraction
MC3T3-E1 and $C_3H_{10}T1/2$ cells were routinely cultivated in minimum essential medium alpha (MEMα; Invitrogen, Cat#22561-021) or in DMEM with high glucose (Invitrogen, Cat#41965-039), respectively. All culture media were supplemented with 10% fetal calf serum (FCS; BioConcept Cat#2-01F10-I, lot. Z04459P), 2 mM L-glutamine (Invitrogen Cat#25030-024), 50 IU penicillin/50 ug/ml streptomycin (Invitrogen Cat#15140-122) and 10 mM Hepes (Invitrogen Cat#15630-056) (maintenance culture medium)

Cells were seeded in maintenance culture medium in 6 well plates (3 ml/well) and grown until confluence (with $1.4 \times 10^5$ MC3T3-1b cells/well, confluence was reached at day 3; with $1.0 \times 10^5$ $C_3H_{10}T1/2$ cells/well, confluence was reached at day 3). Following overnight serum depletion in culture medium containing 1% FBS, the medium was replaced by fresh one supplemented with 1% FBS, BMP-6 (R&D Systems, Cat#507-BP) and the substance(s) to be tested. Prior to their addition to the cells, BMP-6 and the substance(s) to be tested were pre-incubated for 1 h at room temperature, as it had been described for a phospho-Smad 1/3/5 in $C_3H_{10}T1/2$ (Winkler, EMBO J., 2003, 22(23):6267-76). When testing anti-sclerostin antibodies, these were preincubated with sclerostin overnight at 4° C., before being incubated with 0.2 nM BMP-6 for 1 h at room temperature and being finally added to confluent cells. After the appropriate treatment time, the cells were washed with 2 ml ice-cold PBS. One hundred μl/well PhosphoSafe Extraction Reagent and 1:200 diluted Protease Inhibitor Cocktail were then added to the cells which were then incubated on ice for 5 min. Cells were scraped off the wells and transferred into a microfuge tube. The cell extract was kept on ice for 15 min, interrupted by a vortex step every 5 min. Afterwards, the cell extract was centrifuged for 5 min at 16'000 g and 4° C. Finally, the supernatant was transferred into a fresh microfuge tube for protein determination.

Protein concentration in cell lysate was determined using the BCA Protein Assay Kit according to the manufacturer's instruction. BSA was used as standard. For denaturation, the cell lysate was diluted 1:2 with Laemmli buffer (Bio-Rad, Cat#161-0737, containing 13-Mercaptoethanol (1:20, Merck, Cat#1.12006) freshly added) and boiled for 5 min at 95° C. After cooling down, the samples were stored at −20° C. until further use.

Western Blot
Smad (H-465) antibody (Santa Cruz, Cat.Nb.: sc-7153) is a rabbit polyclonal IgG, raised against amino acids 1-465 representing full length Smad1 of human origin. It should recognize Smad1, Smad2, Smad3, Smad5 and Smad8 of human, rat and mouse origin. Phospho-Smad1 (Ser463/465)/Smad5 (Ser463/465)/Smad8 (Ser426/428) antibody (Cell Signalling, Cat#9511) is a rabbit polyclonal IgG, raised against a synthetic phospho-peptide corresponding to residues surrounding Ser463/465 of human mad5. It should detect endogenous levels of Smad1 only when dually phosphorylated at serine 463 and serine 465, as well as Smad5 and Smad8 only when phosphorylated at the equivalent sites of human, mouse, rat, mink and xenopous origin. The antibody does not cross-react with other Smad-related proteins.

The XCell SureLock Mini Cell system (Invitrogen) was prepared according to the manufacturer's instruction. The protein samples (2 μg for a Smad, 5 μg for a Phospho-Smad Western analysis) were loaded in equal final volume on a 7% NuPAGE Novex Tris-Acetate Gel in 1× Running Buffer. See-Blue Plus2 pre-stained standard (10 μl, 1:10; Invitrogen, Cat# LC5925) and MagicMark XP Western protein standard (10 μl, 1:100; (Invitrogen, Cat#; LC5602) were used as molecular weight markers. The gel was run for 75 min with constant voltage (150 V).

Blotting pads and filter papers were soaked in 700 ml 1× NuPAGE Transfer Buffer. A PVDF transfer membrane was first soaked for 30 sec in methanol and then transferred in 1× NuPAGE Transfer Buffer (Invitrogen, Cat#NP0006, Transfer Buffer:Methanol 10:1 freshly prepared). The gel cassette plates were separated with a gel knife, one pre-soaked filter paper was placed on top of the gel and any trapped air bubbles carefully removed. The plate was turned up side down on Saran wrap and after removal of the plate, the pre-soaked transfer membrane was placed on the gel and any air bubbles were removed. A second pre-soaked filter paper was placed on top and any air bubbles removed. Two soaked platting pads were placed into the cathode core of the Cell II Blot Module. The gel/membrane sandwich was carefully picked up and placed on the blotting pads (with the gel closest to the cathode core). Finally, 3 pre-soaked blotting pads were placed on the membrane assembly and the anode core was added on the top. The blot module was slid into the guide rails on the lower buffer chamber and the wedge was locked into position according to the manufacturer's instruction. The blot module was filled with 1× NuPAGE Transfer Buffer until the gel/membrane assembly was covered. The outer buffer chamber was filled with 650 ml deionized water and the protein transfer to the PVDF membrane was performed with constant voltage (30 V) for 2 hours.

Following the blotting, the membrane was first washed for 10 min in 0.05% Tween 20 in PBS and then blocked under gentle shaking for 1 hour in 25 ml SuperBlock T20 Blocking Buffer at room temperature. The primary antibody (Phospho-Smad 1/5/8 or Smad (H-465)) was added to the membrane in a 1:1000 dilution in SuperBlock T20 Blocking Buffer (Pierce, Cat#37516) and the membrane was incubated overnight at 4° C. under shaking. The membrane was then washed 3 times for 10 min with 0.05% Tween 20 (Fluka, Cat#93773) in PBS before being incubated with the RPconjugated secondary antibody (1:1000 in SuperBlock T20 Blocking Buffer) for 60 min at room temperature under shaking. A least 3 washing steps of 10 min each were performed before the membrane was incubated for 5 min with the SuperSignal West Femto Substrate Working Solution (Pierce, Cat#34095). Finally, the membrane was placed in a plastic pocket and imaged with Fluor-S MultiImager (Bio-Rad) and Camera. An optimal exposure time of 1 to 2 min was determined by comparing images taken between 30 sec up to 5 min.

Data Analysis

The chemiluminescence activities were measured using Quantity One (Bio-Rad) and the $EC_{50}$ values were calculated using XLfit4 software. Each phospho-Smad signal was normalized by its corresponding total Smad signal.

LRP6/Sclerostin ELISA

Ninety six-well microtiter non-treated plates were coated with 100 μl/well LRP6/Fc (1 μg/ml, R&D Systems, Cat#1505-LR) diluted in PBS. As control for non-specific binding (NSB), a few wells were filled with 100 μl/well PBS. The plates were covered with plastic film and incubated overnight at RT. Following the coating, plates were washed 3 times with 200 μl/well 0.05% Tween 20 (Fluka, Cat#93773) in PBS and wells were blocked for 1 h at 37° C. by adding 300 μl/well SuperBlock blocking buffer (Pierce, Cat#37535) in TBS. After incubation, the block solution was removed and 100 μl/well sclerostin (*E. coli* derived, Novartis; 1-1000 ng/ml,) diluted in 1% BSA in PBS were added. The plates were incubated for 2 h at RT before being washed 3 times with 200 μl/well 0.05% Tween 20 in PBS. Afterwards, 100 μl/well anti sclerostin antibody (1 μg/ml) diluted in 1% BSA in PBS were added and plates incubated for 2 h at RT before being washed 3 times with 200 μl/well 0.05% Tween 20 in PBS. Finally, 100 μl/well ALP conjugated anti Goat IgG Ab (1:5000; Sigma Cat#A-7888) diluted in 1% BSA (Sigma Cat. Nb.:A-7888) in PBS were added for 1 h at RT and plates were then washed 3 times with 200 μl/well 0.05% Tween 20 in PBS. To determine ALP, 1000/well ALP substrate (Sigma, Cat#S0942) solution (1 tablet per 5 ml diethanolamine substrate buffer 1×; Pierce, Cat#34064) was added to the plates for 90 min and optical density measured at 405 nm.

LRP4 Overexpression in HEK293 Cells

HEK293 cells (ATCC Cat#CRL-1573) were routinely cultivated in DMEM/F12 (Invitrogen Cat#21331-020) supplemented with 10% FCS (BioConcept Cat#2-01F10$^{-1}$, lot. Z04459P), 2 mM L-glutamine (Invitrogen Cat#25030-024), 100 IU penicillin/100 μg/ml streptomycin (Invitrogen Cat#15140-122) and 10 mM HEPES (Invitrogen Cat#15630-056). Hek293 cells were seeded at $5\times10^4$ cells/well in poly-D-Lysine 48 well-plate format and incubated for 24 h before performing the transfection with Lipofectamine 2000 (Invitrogen Cat#11668-019). For each well to be transfected, the following amount if plasmids was added to a final volume of 25 μl OptiMEM®I (Gibco, Cat#31985-047) and mixed gently: for control wells (pmaxGFP, 62.5 ng, pcDNA3+, 125 ng; SuperTopFlash (STF) 62.5 ng; SV40-driving *Renilla luciferase* plasmid, 0.75 ng) and for Wnt1 treatment wells (pmaxGFP, 62.5 ng, pcDNA-wnt1, 62.5 ng; pcDNA3+, 62.5 ng; SuperTopFlash (STF) 62.5 ng; SV40-driving *Renilla luciferase* plasmid, 0.75 ng) and for LRP4-Wnt1 treatment wells (pcDNA3+-LRP4, 62.5 ng, pcDNA3+-wnt1, 62.5 ng; pcDNA3+, 62.5 ng; SuperTopFlash (STF) 62.5 ng; SV40-driving *Renilla luciferase* plasmid, 0.75 ng). In a second tube, 0.8 μl of Lipofectamine 2000 was diluted to a final volume of 25 μl of OptiMEM®I and incubated at room temperature for 5 minutes. The contents in the two tubes were then mixed by adding the content in the lipid tube to the DNA tube and incubated for 30 minutes at room temperature to allow DNA-lipid complex formation. The DNA-lipid complex (50 μl) was then evenly added to wells and incubated at 37° C. in 5% $CO_2$ for 5 hours. At the end of the 5-hour incubation, cells were ready for a 20 h treatment with testing reagents such as SOST, DKK1 (R&D Cat#1096-DK), antibodies etc. The luciferase assay was performed as described under "Wnt-assay" but adding 150 μl Passive Lysis Buffer instead.

LRP4 Overexpression in C28A2 Cells

C28a2 cells (from Mary Goldring, Harvard Institutes of Medicine, Boston, Mass., US) were cultivated in the same medium as HEK293 (see above) except that HEPES was not present and a supplement of non-essential amino acids (Gibco Cat#11140) was added. C28a2 cells were seeded at $1\times10^5$ cells/well in a 24-well plate format in antibiotic free culture medium and incubated overnight before performing the transfection with Lipofectamine 2000 (Invitrogen Cat#11668-019). For each well to be transfected, the following amount of plasmids (600 ng/well total) was added to a final volume of 50 μl OptiMEM®I (Gibco, Cat#31985-047) and mixed gently: for control wells (SuperTopFlash (STF) 100 ng; SV40-driving Renilla luciferase plasmid, 2 ng and pcDNA3+, 500 ng to compensate) and for Wnt1 treatment wells (pcDNA-wnt1 plasmid, 100 ng; LRP5 plasmid, 100 ng; SuperTopFlash (STF) 100 ng; SV40-driving *Renilla luciferase* plasmid, 2 ng and pcDNA3+, 300 ng) and for LRP4-Wnt1 treatment wells (pcDNA-wnt1 plasmid, 100 ng; LRP5 plasmid, 100 ng; LRP4 plasmid, 100 ng; SuperTopFlash (STF) 100 ng SV40-driving *Renilla luciferase* plasmid, 2 ng and pcDNA3+, 200 ng). In a second tube, 1.6 μl of Lipofectamine 2000 was diluted into 48.4 μl of OptiMEM®I and incubated at room temperature for 5 minutes. The contents of the two tubes were then mixed by adding the content of the lipid tube to the DNA tube and incubated for 30 minutes at room temperature to allow DNA-lipid complex formation. The DNA-lipid complex (100 μl) was then evenly added to wells and incubated at 37° C. in 5% $CO_2$ for 2 hours. At the end of the 2 hour incubation, transfection medium was replaced by 450 μl/well antibiotic-free medium and cells were incubated for 24 h. Cells were then treated for 20 h with testing reagents such as SOST, or DKK1 (R&D Cat#1096-DK). The luciferase assay was performed as described under "Wnt-assay".

LRP4 Knockdown in HEK293 Cells

Wnt1/STF/Renilla Hek293 cells (a stable clone issued from the stable transfection of Hek293 cells (ATCC Cat#CRL-1573)) with Wnt1 expression plasmid, SuperTopFlash reporter plasmid, and a SV40-driving Renilla luciferase plasmid) were routinely cultivated in DMEM 4500 g/L glucose (Invitrogen Cat#41965-035) supplemented with 10% FCS (Amimed Cat#2-0F100-I), 2 mM L-glutamine (Invitrogen Cat#25030-081), 100 IU/ml penicillin/100 μg/ml streptomycin (Gibco Cat#15140-163), 6 μg/ml puromycin (Invitrogen Cat#ant-pr-1), 150 μg/ml zeocin (Invitrogen Cat#45-0430) and 150 μg/ml hygromycin (Invitrogen Cat#10687-

010). The selection antibiotics were left out during knockdown experiments. Cells were seeded at $0.6 \times 10^5$ cells/well in poly-D-Lysine 24 well-plate format and left to attach overnight before performing the transfection of LRP4 siRNAs with HiPerFect (Qiagen Cat#301707). The sense and anti-sense sequences of the LRP4 siRNA used were as follow:

```
LRP4a:
                                  (SEQ ID NOs: 160/161)
TAAATTATCATAAAGTCCTAA/AGGACTTTATGATAATTTATT;

LRP4b:
                                  (SEQ ID NOs: 162/163)
ATAGTGGTTAAATAACTCCAG/GGAGTTATTTAACCACTATTT;

LRP4c:
                                  (SEQ ID NOs: 164/165)
TAAATTCTCGTGATGTGCCAT/GGCACATCACGAGAATTTATT;

LRP4d:
                                  (SEQ ID NOs: 166/167)
TTTCTTATAGCACAGCTGGTT/CCAGCTGTGCTATAAGAAATT;

LRP4e:
                                  (SEQ ID NOs: 168/169)
TAGACCTTTCCATCCACGCTG/GCGTGGATGGAAAGGTCTATT;
```

For each well to be transfected, two eppendorf tubes were prepared: the first one contained 0.2 µl of a 20 nM stock of one of the LRP4 siRNA or 0.1 µl of a 20 nM stock of two different LRP4 siRNA (the final total concentration in siRNA/well is 6.6 nM) and 50 µl Optimem and the second one, 3 µl HiPerFect and 47 µl Optimem. The content of the second tube was added to the first one, shortly vortexed and left for 10 minutes at room temperature. One hundred µl of this mixture was then added to the respective well and, cells were incubated at 37° C. under 5% $CO_2$ for 30 hours. Afterwards, transfection mixture was removed and replaced by fresh antibiotic free culture medium (450 µl/well) and left to incubate for an other 24 hours. Before SOST or DKK1 treatment, medium was removed, replaced by fresh antibiotic free culture medium containing appropriate dilution of SOST or DKK1 (R&D Cat#1096-DK) and cells were incubated for 20 hours at 37° C. under 5% $CO_2$. Luciferase determination was then performed as described under "Wnt-assay".

Animal Models

Eight-month-old female OF1/IC mice (n=16/group, Charles River, France) were administered twice weekly intravenously anti-sclerostin antibody ANTIBODY A (25 mg/kg, h/mIgG2a) (MOR05813) or control antibody (anti-PC-h/mIgG2a). Control groups received either daily subcutaneously 100 microg/kg PTH(1-34) or PBS vehicle. Treatment lasted 2.5 weeks for all animals. Half of the animals (n=8/group) was sacrificed at that time point for histomorphometric analysis. Treatment continued for the remaineder of the animals (n=8/group) up to 5 weeks.

Tibial bone mass and geometry of the animals was measured at the initiation of treatment by peripheral quantitative computed tomography (pQCT) and micro computed tomography (microCT). Animals were distributed evenly according to body weight and tibial total bone mineral density as measured by pQCT into groups. Bone mineral density, mass and geometry changes were evaluated after 2.5 and 5 weeks of treatment. Body weight was monitored weekly. Animals which were sacrificed after 2.5 weeks of treatment were administered two fluorochrome labels for marking of bone mineralization 10 and 3 days prior to necropsy. Blood was taken at necropsy. Dual energy x-ray absorptiometry (DEXA) measurements were carried out at necropsy on excised tibia, femur, and lumbar vertebrae. The bones were fixed, dehydrated, and embedded for microtome sectioning and histomorphometric analysis of bone formation dynamics.

Treatment Protocol

Control antibody: anti-PC-h/mIgG2a,
concentration: 2.5 mg/ml, application volume: 10 ml/kg
Vehicle: 50 mM Citrat, 140 mM NaCl
Anti-sclerostin antibody: anti-SOST-MOR05813, h/mIgG2a, 2.45 mg/ml, application volume: 10 ml/kg
Vehicle: 50 mM Citrat, 140 mM NaCl
hPTH (1-34) (Bachem, Bubendorf, Switzerland) 100 µg/kg
vehicle: PBS+BSA 0.1%

Treatment Groups:
1 isotype control iv.=anti-PC-mIgG2a
2 anti-SOST-MOR05813 iv.
3 vehicle control sc.=PBS+BSA 0.1%
4 hPTH(1-34) sc.

Maintenance Conditions

Animals were housed in groups of four to five animals at 25° C. with a 12:12 h light-dark cycle. They were fed a standard laboratory diet containing 0.8% phosphorus and 0.75% calcium (NAFAG 3893.0.25, Kliba, Basel, Switzerland). Food and water were provided ad libitum.

Statement on Animal Welfare

Animal experimentation was carried out according to the regulations effective in the Canton of Basel-City, Switzerland.

Methods

Peripheral Quantitative Computed Tomography (pQCT)

The animals were placed in a lateral position under inhalation narcosis (Isoflurane, 2.5%). The left leg was stretched and fixed in this position.

Cross-sectional bone mass, density and geometry was monitored in the proximal tibia metaphysis at level of the mid-fibula head and 1.8 mm distal to the proximal end of the tibia as detected in the scout scan using an adapted Stratec-Norland XCT-2000 fitted with an Oxford 50 AM X-ray tube and a collimator of 0.5 mm diameter. The following setup was chosen for the measurements: voxel size: $0.1 \times 0.1 \times 0.5$ mm; scan speed: scout view 10 mm/s; final scan 3 mm/s, 1 block, contour mode 1, peel mode 2; cortical threshold: 610 mg/cm3, inner threshold: 610 $mg/cm^3$.

Micro Computed Tomography (microCT)

The animals were placed in a lateral position under inhalation narcosis (Isoflurane, 2.5%). The left leg was stretched and fixed in this position.

Cancellous bone structure was evaluated in the left proximal tibia metaphysis using a Scanco vivaCT20 (Scanco Medical AG, Switzerland). The non-isometric voxels had a dimension of $10.5 \times 10.5 \times 10.5$ µm. From the cross-sectional images, the cancellous bone compartment was delineated from cortical bone by tracing its contour. In all the other slices, boundaries were interpolated based on the tracing to define the volume of interest. 143 slices within the area of the secondary spongiosa (starting below the lateral lower edges of the growth plate) were evaluated. A threshold value of 370 was used for the three dimensional evaluation of structural parameters.

Dual Energy X-Ray Absorptiometry (DEXA)

Ex vivo DEXA measurements were performed on the left tibia, the left femur and in the lumbar vertebrae 1-4. Ethanol (70%) was used for soft tissue simulation. The measurements were performed using a regular Hologic QDR-1000 instrument adapted for measurements of small animals. A collimator with 0.9 cm diameter and ultrahigh resolution mode (line spacing 0.0254 cm, resolution 0.0127 cm) was used.

Fluorochrome Labelling:

Alizarin (20 mg/kg, subcutaneous, alizarin complexone, Merck, Dietikon, Switzerland) was a 10 days prior to necropsy Calcein (30 mg/kg, subcutaneous, Fluka, Buchs, Switzerland)-3 days prior to necropsy Histology and Histomorphometry After dissection, the right femur and lumbar vertebrae five and six were placed for 24 h into Karnovsky's fixative, dehydrated in ethanol at 4° C., and embedded in resin (methylmethacrylate). Using a Microtome 2050 Supercut (Reichert Jung, Arnsberg, Germany), a set of 5 µm-thick non-consecutive microtome sections were cut in the frontal mid-body plane for evaluation of fluorochrome-label-based bone formation. The sections were examined using a Leica DM microscope (Leica, Heerbrugg, Switzerland) fitted with a camera (SONY DXC-950P, Tokyo, Japan) and adapted Quantimet 600 software (Leica, Cambridge, United Kingdom). One section per animal was sampled. Microscopic images of the specimens were digitalized and evaluated semi-automatically on screen. Bone perimeter, single and double-labelled bone perimeter, and interlabel width were measured (×200 magnification). Mineralized perimeter values (percent), mineral apposition rates (micrometers/day) (corrected for section obliquity in the cancellous bone compartment), and daily bone formation rate values (daily bone formation rate/bone perimeter [micrometers/day]) were calculated. All parameters were evaluated in the secondary spongiosa of the distal femur metaphysis and in one lumbar vertebra. Another set of sections were tartrate-resistant acid phosphatase (TRAP) stained. Osteoclast surface per bone surface (%) was evaluated in the secondary spongiosa:

Statistical Analysis

Results are expressed as mean+/−SEM. Statistical analysis was carried out using Student's t test (two-tailed; unpaired). Treatment (anti-sclerostin antibody or hPTH(1-34) was tested for difference to control (control anti-body or PBS), *, +$p<0.05$, **, ++ $p<0.01$.

Affinity Determination

Affinity Determination of Selected Anti-Human Sclerostin Fabs Using Surface Plasmon Resonance (Biacore)

The kinetic constants $k_{on}$ and $k_{off}$ were determined with serial dilutions of the respective Fab binding to covalently immobilized antigen sclerostin using the BIAcore 3000 instrument (BIAcore, Uppsala, Sweden). For covalent antigen immobilization standard EDC-NHS amine coupling chemistry was used. Kinetic measurements were done in PBS (136 mM NaCl, 2.7 mM KCl, 10 mM $Na_2HPO_4$, 1,76 mM $KH_2PO_4$ pH 7.4) at a flow rate of 20 µl/min using Fab concentration range from 1.5-500 nM. Injection time for each concentration was 1 min, followed by 3 min dissociation phase. For regeneration 2×5 µl 10 mM glycine pH 1.5 was used. All sensograms were fitted using BIA evaluation software 3.1 (BIAcore).

Electrochemiluminescene (BioVeris) Based Binding Analysis for Measuring Affinities of Sclerostin Binding Fab in Lysates For the measurement of the affinity of sclerostin-binding antibody fragments in E. coli lysates (BEL extracts), binding was analyzed by a BioVeris M-384 SERIES® Workstation (BioVeris Europe, Witney, Oxfordshire, UK).

The experiment was carried out in 96-well polypropylene microtiter plates and PBS supplemented with 0.5% BSA and 0.02% Tween 20 as assay buffer. Biotinylated human sclerostin protein was immobilized on M-280 Streptavidin paramagnetic beads (Dynal) according to the instructions of the supplier. 1:25 dilution of the bead stock solution was added per well. 100 µl diluted BEL extract and beads were incubated overnight at RT on a shaker. For detection, anti-human (Fab)'2 (Dianova) labeled with BV-Tag™ according to supplier instructions (BioVeris Europe, Witney, Oxfordshire, UK) was used.

Randomly picked clones were analyzed with the method described above. Clones giving the highest values were chosen for further analysis in solution equilibrium titration.

Determination of Affinities of Fabs to Sclerostin Using Solution Equilibrium Titration (SET)

For KD determination, monomer fractions (at least 90% monomer content, analyzed by analytical SEC; Superdex75, Amersham Pharmacia) of Fab were used. Electrochemiluminescence (ECL) based affinity determination in solution and data evaluation were basically performed as described by Haenel et al., 2005. A constant amount of Fab (25 µM) was equilibrated with different concentrations (serial 3″ dilutions) of unlabelled human, mouse or Cynomolgus sclerostin (starting concentration: 500 µM) in solution. Biotinylated human sclerostin (0.5 µg/ml) coupled to paramagnetic beads M-280 Streptavidin, Dynal) and BV-Tag™ (BioVeris Europe, Witney, Oxfordshire, UK) labeled anti-human (Fab)'2 antibody (Dianova) were added and incubated for 30 min. Subsequently, the concentration of unbound Fab was quantified via ECL detection using M-SERIES® 384 analyzer (BioVeris Europe).

Affinity improved Fab clones where identified by an ECL based high throughput affinity screening BioVeris assay. After hit selection 4 sub-clones were consolidated by the same method.

Receptor Binding Inhibition Potency Assay Using BioVeris™

For the BioVeris™-based binding inhibition potency assay recombinant human BMP-2 was directly coupled (NHS/EDC chemistry) to carboxylic acid M-270 magnetic beads (Dynal) according to supplier instructions. The assay was performed in 96-well polypropylene microtiter plate (Nunc). 50 µl/well of purified Fab in assay buffer (PBS+1% Tween 20 (stringent) or 0.1% Tween 20 (less stringent)+1% BSA) were diluted in 1:3 dilution steps (staring concentration: 1000 nM). 50 µl/well of biotinylated human sclerostin (4 nM) was added to each Fab dilution. After incubation for 90 min shaking at 400 rpm on an Eppendorf Thermomixer at 22° C., 25 µl of the BMP-2 coated beads (2.7E07 beads per ml) and 1:500 diluted Streptavidin labeled with BV-tag™ according to supplier instructions (BioVeris Europe) were added to each well and incubated for 30 min (800 rpm, 22° C.). Detection was performed by BioVeris M-384 SERIES® Workstation (BioVeris Europe). For $EC_{50}$ determination a 4-parameter logistic fit model (XLfit, IDBS) was used.

Production of Immunoglobulins

Conversion into the Human IgG1 Format and Human/Mouse IgG2a Format

In order to express full length IgG, variable domain fragments of heavy (VH) and light chains (VL) were subcloned from Fab expression vectors into appropriate pMorph®Ig vectors: pMorph®_h_Ig1 and chimeric human/mouse pMorph®2_h/m_Ig2a. Restriction enzymes EcoRI, MfeI, BlpI were used for subcloning of the VH domain fragment into pMorph®_h_IgG1 or pMorph®2_h/m_IgG2a and EcoRV, BsiWI, HpaI for subcloning of the VL domain fragment into pMorph®_h_Igκ, pMorph®_h_IgA and pMorph®2_h/m_Igλ vectors respectively.

Restriction enzymes EcoRI, MfeI and BlpI were used for subcloning of the VH domain fragment into pMORPH®_h_IgG1: the vector backbone was generated by EcoRI/BlpI digestion and extraction of the 6400 bp fragment whereas the VH fragment (350 bp) was produced by digestion with MfeI and BlpI and subsequent purification. Vector and insert were ligated via compatible overhangs generated by the EcoRI and MfeI digests, respectively, and via the BlpI site. Thereby, both the EcoRI and the MfeI restriction site are destroyed.

Restriction enzymes MfeI and BlpI were used for subcloning of the VH domain fragment into pMORPH®2_h/m_gG2a. In this new generation of IgG vectors, upon other modifications, the EcoRI site (which allowed only sub-cloning via compatible overhangs) was replaced by the MfeI site thus allowing MfeI/BlpI digestion of both, vector and insert.

Subcloning of the VL domain fragment into pMORPH®_h_Igκ was performed via the EcoRV and BsiWI sites, whereas subcloning into pMORPH®_h_Igλ and pMORPH®2_h/m_Igλ was done using EcoRV and HpaI.

Transient Expression and Purification of Human IgG

HEK293 or HKB11 cells were transfected with an equimolar amount of IgG heavy and light chain expression vectors. On days 4 or 5 post-transfection the cell culture supernatant was harvested. After adjusting the pH of the supernatant to pH 8.0 and sterile filtration, the solution was subjected to standard protein A column chromatography (Poros 20A, PE Biosystems).

Example 1

Generation of Human and Cyno Recombinant Sclerostin Proteins

The full-length cDNA coding for human sclerostin precursor (GenBank Acc.No AF326739) featuring a natural signal peptide (aa 1-213, NPL 005002) was cloned into the mammalian expression vector pRS5a by insertion into the restriction sites Asp718 and Xba1. A protein detection and purification tag (APP=EFRH) was added to the C-terminus of the gene.

Following small scale expression verification in transient 6-well-plate transfection assays, the generation of stable transfection pools was initiated by transfection of four pools (1.0×10E6 cells each) by lipofection. 48 hours post transfection selection of transfectants was started by addition of the antibiotic Zeocin™ at 100 µg/ml concentration. Once all four pools had resumed normal growth recombinant protein titers were assessed by analytical affinity chromatography on anti-APP HPLC and the highest producing pool—Pool2—was selected for adaptation to serum-free medium and further scale-up. Simultaneously, large-scale transient expression trials on the 10-l-scale were also performed using Polyethylenimine as carrier of plasmid DNA during transfection and the Wave™ bioreactor system (C20SPS-F, Art.-No. 100.001, Wave Biotech) as culture system. The cell culture supernatants of 12-22 l were harvested 7-10 days post transfection and concentrated by cross-flow filtration and diafiltration prior to purification.

Human and cyno SOST were purified by immunoaffinity chromatography. Briefly, batches of 10-20 L tissue culture supernatants were concentrated to 1-2 L by cross-flow filtration (cut off 10 kDa) and applied at 2 ml/min on a 50 ml anti-APP Sepharose column prepared by coupling the proprietary monoclonal anti-Ab1-40/APP (6E10-A5) to CNBr activated Sepharose 4B according to the manufacturer instructions (10 mg antibody per ml resin). After base-line washing with PBS, bound material was eluted with 100 mM glycine, pH 2.7 neutralized and sterile filtered. Protein concentration was determined by A280 using computed absorption factors. The purified proteins were finally characterized by SDS-PAGE, N-terminal sequencing and LC-MS. An aliquot of purified human SOST was biotinylated in PBS for 1 hour at 37° C. using 1 mM sulfo-NHS-lc-biotin (Uptima; UP54398A). Excess reagent was then removed by extensive dialysis against PBS.

E. coli Derived Human SOST

His$_6$-PreScission tagged SOST aa24-213 (NPL006071, plasmid pX1504) and SOST aa24-213 (NPL006690, plasmid pXI515) were produced by refolding. E. coli Tuner (DE3) were transformed with either plasmid.

Batch PSU5257 was fermented on a 20 litre scale (V9405) using modified TB medium (version lab 112). Cells were induced at an OD600 of 3.90 with 1 mM IPTG and induced for 3 hours 30 minutes at 37° C. Harvesting was carried out using a continuous flow centrifuge, resulting in a wet cell pellet weighing 190 g.

Batch PSU11274 was fermented on a 20 litre scale in 16 L minimal M9-1 medium supplemented with $^{15}$N-labelled ammonium chloride. Cells were induced with 1 mM IPTG once an OD600 of 1.5 had been reached and harvested at an OD600 of 3.3 using a continuous flow centrifuge, resulting in a wet cell pellet weighing 50 g.

Wet cell pellets from the above fermentation were lysed in 8 volumes of 50 mM Tris pH 8.0 (containing 5 mM each EDTA, DTT and Benzamidine-HCl) using an Avestin C-50 emulsifier and centrifuged for 30 min at 12,000 rpm. The supernatant was discarded and the resultant pellet re-suspended in 10 volumes lysis buffer and centrifuged again. The process was repeated 3 more times, after which the lysis buffer was replaced with Milli-Q water, containing 5 mM DTT. The pellets were washed a further two times under these conditions.

Inclusion bodies were dissolved in 8M Guanidine-HCl (containing 100 mM DTT, 50 mM Tris pH 8 and 5 mM EDTA) for 3-4 h at ambient temperature, then centrifuged at 20,000 rpm for 30 min, filtered through a 0.45 uM filter. Refolding was initiated by fast-dilution with 88 volumes (PSU11274) and 92 volumes (PSU5257) chilled refolding buffer (0.5M Tris containing 0.9M Arginine-HCl, 5 mM GSH and 0.5 mM GSSG pH 8). The solution was stored at 4° C. for 1 week. At this stage, the two preparations were treated slightly differently, because of the requirement to remove the his$_6$-tag from PSU5257 prior to completing refolding

PSU5257

The diluted folding solution was diafiltered against 1.5 volumes of 50 mM Tris pH 8, 5 mM GSH, 0.5 mM GSSG by concentrating 2-fold, then diluting back to the original volume. This was carried out 3 times, after which time, PreScission protease was added and the solution left for 48 h at 4° C. All concentrations/diafiltrations were carried out using a Pellicon II ultrafiltration cassette with a 10 KDa cut-off membrane. Finally the solution was concentrated 10-fold.

PSU11274

The diluted refolding solution was concentrated 10-fold. LC-MS was used to confirm the formation of all 4 disulphide bridges prior to concentration.

Both preparations were then dialysed against 2×10 volumes of 50 mM sodium acetate pH 5. Following successive filtration through glass wool and a 3.0 µm membrane to remove precipitated protein, purification was carried out using SP-Sepharose™ high performance cation-exchange chromatography. The column was equilibrated with the dialysis buffer and subsequently eluted with a 0-1M NaCl gradient in the same buffer over 20 column volumes. Sclerostin eluted as a single peak with a slight shoulder, which was discarded. In the case of PSU5257, the main peak was collected, concentrated subjected to size-exclusion chromatography using a column of Superdex 75™, equilibrated with 50 mM Tris, 150 mM NaCl. With PSU11274, the sample was provided directly after cation-exchange.

Cynomolgus monkey SOST cDNA (cySOST) was amplified by RT-PCR with primers based on the African green monkey SOST sequence (GenBank Accession #AF326742). The 5' primer (ATGCAGCTCCCACTGGCCCTGTGTCT-TGT) (SEQ ID NO: 170) corresponds to N-terminus of the signal peptide sequence and is not in the final secreted protein; the 3' primer (AATCAGGCCGAGCTGGAGAACGC-CTACTAG) (SEQ ID NO: 171) corresponds to a region that is conserved among human, African green monkey and mouse. The amplified fragment was subcloned into the Bam HI/Eco RI sites of pcDNA3.1(+) and sequence confirmed. This plasmid served further as template for a PCR amplification of cyno-SOST to add a C-terminal APP tag and attB recombination sites for final cloning into pDESTRS5a according to the Gateway technology [cySOST-pDESTRS5a].

Expression was done by large-scale transient transfection at the 10 L scale in the Wave™ bioreactor system, harvested after 9 days post transfection and purified as described above.

Example 2

Generation of Human Sclerostin-Specific Antibodies from the HuCAL GOLD® Library

Therapeutic antibodies against human sclerostin protein were generated by selection of clones having high binding affinities, using as the source of antibody variant proteins a commercially available phage display library, the MorphoSys HuCAL GOLD® library. HuCAL GOLD® library is a Fab library (Knappik et al., 2000) in which all six CDRs are diversified by appropriate mutation, and which employs the CysDisplay™ technology for linking the Fab to the phage surface (WO01/05950, Löhning et al., 2001).

Selection by Panning of Sclerostin-Specific Antibodies from the Library

For the selection of antibodies recognizing human sclerostin several panning strategies were applied.

In summary, HuCAL GOLD® antibody-phages were divided into three pools comprising different VH master genes.

These pools were individually subjected to either
a) a solid phase panning where the antigens (human and mouse sclerostin) were directly coated on Maxisorp 96 well microtiter plates (Nunc, Wiesbaden, Germany) or
b) a capture and semi-solution panning where the antigen (biotinylated sclerostin), respectively the phage-antigen complex was captured on N/A clear strips or
c) a solution pannings with biotinylated sclerostin where the phage-antigen complex was captured by Streptavidin magnetic beads (Dynabeads M-280; Dynal) for each panning pool.

Solid Phase Panning on Sclerostin

For the first round of the panning on sclerostin, wells of the Maxisorp plate were coated overnight with 300 µl (5 µg/ml) of human sclerostin (produced in HEK cells) diluted in PBS. After two washing steps, with 400 µl PBS, the wells were incubated with blocking buffer containing 5% milk powder diluted in PBS.

Prior to the selections, HuCAL GOLD® phages were pre-adsorbed in blocking buffer (5% milk powder/PBS, 0.5% Tween 20) for 2 h at RT to avoid unspecific selection of antibodies.

After washing (2×400 µl PBS) of the coated and blocked Maxisorp plate, 300 µl of the pre-adsorbed phages were added to the coated wells and incubated for 2 h at RT shaking gently. This incubation was followed by 10 wash cycles with PBS and PBS/0.05% Tween 20 at RT.

Bound phages were eluted by adding 300 µl of 20 mM DTT in 10 mM Tris/HCl pH 8.0 per well for 10 min at RT. The eluate was removed and added to 15 ml $E.\ coli$ TGIF$^+$ cells grown to an $OD_{600nm}$ of 0.6-0.8. Phage infection of $E.\ coli$ was allowed for 45 min at 37° C. without shaking. After centrifugation for 5 min at 4120×g, the bacterial pellets were each re-suspended in 600 µl 2×YT medium, plated on LB-CG agar plates and incubated O/N at 30° C. Colonies were then scraped off from the plates and phages were rescued and amplified.

The second and third rounds of selection were performed in an identical way to the first round of selection with the only difference that the washing conditions after binding of phage were more stringent. In the second selection round for some panning conditions mouse sclerostin was used as antigen in order to enrich for mouse cross-reactive antibodies. For some panning conditions another batch of human recombinant sclerostin (produced in $E.\ coli$) was coated.

Semi-Solution Panning on Sclerostin

Two different methods were performed for this kind of panning: a capture semi-solution panning and the standard semi-solution panning procedure.

In detail, for capture semi-solution panning on biotinylated sclerostin, 100 µl of the antigen was coated 2 h at RT on NeutrAvidin (N/A) clear strips (from Pierce, activation level 100 µl, binding capacity 15 µmol per well). The N/A strips were blocked O/N at 4° C. with 200 µl Chemiblock and washed twice with PBS.

The blocked phage solution (Chemiblock/0.05% Tween 20) was added to blocked N/A wells for 30 min and this step was repeated for another 30 min in order to remove NeUtrAvidin binders. Then the pre-cleared phages were transferred to the biotininylated sclerostin immobilized on N/A clear strips, sealed with foil and incubated O/N at RT shaking.

On the next day the phage solution was removed from the antigen coated wells and the wells were washed.

For the standard semi-solution panning the blocked (Chemiblock/0.05% Tween 20), pre-cleared phages were added to a new pre-blocked 1.5 ml reaction tube (Chemiblock/0.05% Tween 20) and then biotinylated human sclerostin was added to a final concentration of 100 nM and incubated O/N at RT shaking.

On the next day the phage-antigen solution from the 1.5 ml reaction tube was added to new blocked wells of the NeutrAvidin strips and allowed to bind for 30 min at RT and then washed.

For both panning procedures bound phages were eluted after washing by adding 300 µl of 20 mM DTT in 10 mM Tris/HCl pH 8.0 per well for 10 min at RT. The eluate was removed and added to 15 ml $E.\ coli$ TG1 cells grown to an $OD_{600nm}$ of 0.6-0.8. Phage infection of $E.\ coli$ was allowed for 45 min at 37° C. without shaking. After centrifugation for 5 min at 4120×g, the bacterial pellets were each re-suspended in 600 µl 2×YT medium, plated on LB-CG agar plates and incubated O/N at 30° C. Colonies were then scraped off from the plates and phages were rescued and amplified.

The second and third rounds of selection were performed in an identical way to the first round of selection with the only difference that the washing conditions after binding of phage were more stringent.

Solution Panning on Sclerostin

For this type of panning 200 µl of Streptavidin magnetic beads (Dynabeads M-280; Dynal) were washed once with PBS and blocked with Chemiblock for 2 h at RT. 500 µl of phages were blocked with Chemiblock for 1 h at RT rotating. The blocked phages were twice pre-adsorbed against 50 μl blocked. Streptavidin magnetic beads for 30 min. The phage supernatant was transferred to a new blocked 2 ml reaction tube and different concentrations of human biotinylated sclerostin were added (see Tables 5, 6 and 7) and incubated for 1 h at RT rotating. 100 μl of the blocked Streptavidin magnetic beads were added to each panning pool an incubated for 10 min on a rotator. The beads were collected with a particle separator (Dynal MPC-E) for approx. 2.5 min and the solution was removed carefully.

After the wash cycles (Table 2), bound phages were eluted by adding 300 μl of 20 mM DTT in 10 mM Tris/HCl pH 8.0 per well for 10 min at RT. The eluate was removed and added to 15 ml *E. coli* TG1F$^+$ cells grown to an OD$_{600nm}$ of 0.6-0.8. Phage infection of *E. coli* was allowed for 45 min at 37° C. without shaking. After centrifugation for 5 min at 4120×g, the bacterial pellets were each re-suspended in 600 μl 2×YT medium, plated on LB-CG agar plates and incubated O/N at 30° C. Colonies were then scraped off from the plates and phages were rescued and amplified.

The second and third rounds of selection were performed in an identical way to the first round with the only difference that the washing conditions after binding of phage were more stringent. In the second and third selection round for some panning conditions the antigen concentration was reduced.
Subcloning and Expression of Selected Fab Fragments
Microexpression of Selected Fab Fragments To facilitate rapid expression of soluble Fabs, the Fab-encoding inserts of the selected HuCAL GOLD® phages were subcloned via XbaI and EcoRI from the respective display vector into the *E. coli* expression vector pMORPH®X9_MH (Rauchenberger et al., 2003). After transformation of the expression plasmids into *E. coli* TG1 F$^-$ cells chloramphenicol-resistant single clones were picked into the wells of a sterile 96-well microtiter plate pre-filled with 100 μl 2×YT-CG medium and grown O/N at 37° C. 5 μl of each *E. coli* TG-1 culture was transferred to a fresh, sterile 96-well microtiter plate pre-filled with 100 μl 2×YT medium supplemented with 34 μg/ml chloramphenicol and 0.1% glucose per well. The microtiter plates were incubated at 30° C. shaking at 400 rpm on a microplate shaker until the cultures were slightly turbid (~2-4 h) with an OD$_{600nm}$ of ~0.5. To these expression plates, 20 μl 2×YT medium supplemented with 34 μg/ml chloramphenicol and 3 mM IPTG (isopropyl-β-D-thiogalactopyranoside) was added per well (final concentration: 0.5 mM IPTG), the microtiter plates were sealed with a gas-permeable tape, and incubated overnight at 30° C. shaking at 400 rpm.

Generation of whole cell lysates (BEL extracts): To each well of the expression plates, 40 μl BEL buffer was added and incubated for 1 h at 22° C. on a microtiter plate shaker (400 rpm).
Expression and Purification of HuCAL®-Fab Antibodies in *E. coli*

Expression of Fab fragments encoded by pMORPH®X9_Fab_MH in *E. coli* TG1 F– cells in larger scale was carried out in shaker flask cultures using 750 ml of 2×YT medium supplemented with 34 μg/ml chloramphenicol. Cultures were shaken at 30° C. until the OD$_{600nm}$ reached 0.5. Fab expression was induced by addition of 0.75 mM IPTG (isopropyl-1-D-thiogalactopyranoside) and cultivation for further 20 h at 30° C. Cells were harvested and disrupted using lysozyme and Fab fragments isolated onto Ni-NTA chromatography. The apparent molecular weights were determined by size exclusion chromatography (SEC) with calibration standards. Concentrations were determined by UV-spectrophotometry (Krebs et al., 2001).

Example 2

Identification of Sclerostin-Specific HuCAL® Antibodies

Enzyme Linked Immunosorbent Assay (ELISA) for detection of sclerostin binding Fabs on Directly Coated Sclerostin
Maxisorp (Nunc, Rochester, N.Y., USA) 384 well plates were coated with 20 μl of 2.5 μg/ml antigen (human sclerostin—produced in HEK cells, human sclerostin—produced in *E. coli* cells and mouse sclerostin) in PBS, pH 7.4 O/N at 4° C.

The plates were blocked with PBS/0.05% Tween 20 (PBST) containing 5% milk powder for 1 h at RT. After washing of the wells with PBST, BEL-extract, purified HuCAL GOLD® Fabs or control Fabs diluted in PBS were added to the wells and incubated for 1 h at RT. To detect the primary antibodies, the following secondary antibodies were applied: alkaline phosphatase (AP)-conjugated AffiniPure F(ab')2 fragment, goat anti-human, anti-mouse IgG (Jackson ImmunoResearch). For the detection of AP-conjugates fluorogenic substrates like AttoPhos (Roche) were used according to the manufacturer's instructions. Between all incubation steps, the wells of the microtiter plate were washed with PBST three times and five times after the final incubation with the secondary antibody. Fluorescence was measured in a TECAN Spectrafluor plate reader.
Capture Screening with Biotinylated Sclerostin This kind of ELISA was used to screen for HuCAL GOLD® Fabs after proceeding solution pannings.

Maxisorp (Nunc, Rochester, N.Y., USA) 384 well plates were coated with 20 μl of 5 μg/ml sheep anti-human IgG, Fd fragment specific (The Binding Site, Birmingham, UK), diluted in PBS, pH 7.4.

After blocking with 3% BSA in TBS, 0.05% Tween 20 for 2 h at RT, periplasmic extracts or purified HuCAL GOLD® Fabs were added and incubated 1 h at RT. After washing the plates five times with PBST 20 μl of biotinylated sclerostin for specific binding or biotinylated Transferin for unspecific binding were added to the wells.

Subsequently the biotinylated antigen sclerostin was allowed to bind to captured HuCAL®-Fab fragments. And after washing incubated with Streptavidin (Zymex) conjugated to alkaline phosphatase. For the detection of AP-Streptavidin fluorogenic substrates like AttoPhos (Roche) were used according to the manufacturer's instructions (Roche Diagnostics, Mannheim, Germany). Fluorescence emission at 535 nm was recorded with excitation at 430 nm.
Results:

After the pannings the enriched phage pools were subcloned from the pMORPH®23 library vector (allowing efficient antibody display on the phage surface) into the pMORPH®X9_Fab_MH expression vector which mediates periplasmic expression of soluble Fabs. Single clones were picked and soluble Fabs were expressed from these single clones. In total, ~4600 clones were analyzed in primary screening which was performed by binding of the Fabs directly from the bacterial lysates to human and mouse sclerostin immobilized on Maxisorp microtiter plates or by capture of Fabs via anti-Fd antibody to maxisorp microtiter plates followed by binding of biotinylated human sclerostin. Detection was carried out in ELISA after labeling with an Alkaline Phosphatase-labeled anti-human (Fab)'₂ antibody or using Streptavidin alkaline phosphatase.

Hits obtained from the primary screening on recombinant sclerostin with signals >5-fold over background were further analyzed for binding to human HEK and *E. coli* sclerostin and to mouse sclerostin either directly coated or in solution using biotinylated sclerostin. Hits recognizing all sclerostin derivatives were selected and sequenced.

Characterization of HuCAL GOLD® Fabs

Affinity Determination Using Biacore

In order to further characterize the anti-sclerostin antibodies, the affinity to human, mouse and Cynomolgus sclerostin was determined. The recombinant sclerostin protein was immobilized on a CM5 Biacore chip and the Fabs were applied in the mobile phase in different concentrations. For a reliable determination of monovalent affinities only such Fab batches were used for Biacore measurements which showed ≧90% monomeric fraction in a qualitative size exclusion chromatography.

Affinities for recombinant human, Cynomolgus and mouse sclerostin were determined in Biacore. Affinities are ranging from sub nanomolar to over 500 nM on human, to nearly 5000 nM on Cynomolgus and to 4500 nM on mouse sclerostin.

Example 3

Identification of Anti-Human Sclerostin Fab Candidates Inhibiting Sclerostin Binding to Immobilized BMP-2 using the BioVeris™ Device All generated and purified Fabs were tested in the BioVeris-based binding inhibition potency assay for their ability to inhibit sclerostin binding to recombinant human BMP-2. Two different stringency conditions (0.1% versus 1% Tween 20 in buffer system) were tested. 9 of 27 Fabs were able to inhibit sclerostin binding to immobilized BMP-2 under stringent buffer conditions.

Example 4

Reversion of Sclerostin Inhibition of BMP-2 Induced ALP Production in MC3T3 Cells IgG Conversions of Parental Binders and Characterization of IgG 21 candidates were converted into the human IgG1 format by sub-cloning into the pMORPH® h_IgG1 expression vector and the corresponding light chain constructs of the pMORPH®_h_Ig vector series, respectively. Expression was performed by transient transfection of HEK293 or HKB11 cells and the full length immunoglobulins were purified from the cell culture supernatant. Functionality of IgG1s after purification was assessed by ELISA binding to immobilized human, mouse and Cynomolgus sclerostin.

IgGs in Primary Bio-Assay

All purified hIgGs were titered and tested in the ALP assay. The assay was reliable with respect to BMP-2 sclerostin inhibition but the selected candidates could not show sclerostin inhibition in all experiments (assay to assay activity variation, plate to plate variation, high variance within triplicate wells). Therefore only a ranking of activity of the IgGs was possible.

Example 5

Affinity Maturation of Selected Anti-Sclerostin Fabs by Parallel Exchange of LCDR3 and HCDR2 Cassettes The results of testing the IgGs in the ALP assay allowed only a ranking. From this ranking, 4 Fabs were selected on high risk for affinity maturation. All candidates have been selected to be optimized as single lead candidates in L-CDR3 and H-CDR2.

To increase affinity and biological activity of the four selected antibody fragments, LCDR3 and HCDR2 regions were optimized in parallel by cassette mutagenesis using directed mutagenesis (Virnekas et al., 1994), whereby the framework regions were kept constant. Prior to cloning of the maturation libraries, all parental Fab fragments were transferred from the expression vector pMORPH®x9_MH into the CysDisplay™ maturation vector pMORPH®25 via the XbaI/EcoRI restriction sites. This vector provides the phage protein pIII fused N-terminally to a cysteine residue as well as a C-terminal cysteine fused to the Fd antibody chain and thus allows disulfide-linked display of the respective Fab fragments on the phage surface.

For generation of the HCDR2 libraries the HCDR2 region of each parental Fab was excised and replaced by a 590 bp stuffer. This DNA stuffer facilitates the separation of single digested from double digested vector bands and reduces the background of the high-affinity parental Fabs during the maturation pannings. In a subsequent step, the stuffer was excised from the Fab-encoding plasmids of each parental clone and replaced by the highly diversified HCDR2 maturation cassette.

In parallel, the LCDR3 region of five of the four parental clones was replaced by a diversified LCDR3 maturation cassette without intermediate cloning of a stuffer.

Sizes of the maturation libraries ranged between $1 \times 10^7$ and $4 \times 10^8$ clones with a cloning background below 1%, and quality control by sequencing revealed a good quality of each library. Only the LCDR3 library of parental clone MOR04520 had a low size ($<10^6$) and many incorrect clones and was therefore not included in the maturation pannings.

For each LCDR3 and HCDR2 maturation library, antibody-displaying phages were prepared and phage titers determined by spot titration.

Panning Strategies for Affinity Maturation

The antibody-displaying phages from the following maturation libraries were subjected to separate pannings and screenings:

Lead 1: MOR04518 (L-CDR3 maturation)
Lead 1: MOR04518 (H-CDR2 maturation)
Lead 2: MOR04520 (H-CDR2 maturation)
Lead 3: MOR04532 (L-CDR3 maturation)
Lead 3: MOR04532 (H-CDR2 maturation)
Lead 4: MOR04799 (L-CDR3 maturation)
Lead 4: MOR04799 (H-CDR2 maturation)

For each lead library three different pannings were performed. For each panning strategy different stringency conditions were applied. To increase panning stringency and to select for improved off-rates, extensive washing and competition with purified parental Fab or with soluble recombinant sclerostin was performed. After the maturation pannings the enriched phagemid pools were sub-cloned into the pMORPH®x9_MH expression vector. About 2900 single clones were picked and Fabs expressed by induction with IPTG.

BioVeris™ Affinity Ranking and Screening for Improved Affinities

For identification of affinity-improved sclerostin-specific Fabs the bacterial lysates of ~2900 single clones were diluted and checked for Fab binding to biotinylated human sclerostin immobilized on Streptavidin-coated beads. The binding was analyzed with a BioVeris Workstation. Those clones giving the highest signals indicate improved affinity and were therefore chosen for further analysis by solution equilibrium titration.

For this purpose, 176 single clones were selected and preliminary affinities were determined via 4-point solution equilibrium titration (SET) in BioVeris. From these data, 24 clones showing the best affinities were selected. These Fabs were purified in the mg scale.

Final affinities were determined using an 8-point SET measurement and human, mouse and cynomolgus sclerostin.

Optimized Fabs in Primary Bio-Assay

The optimized Fabs were tested in the cellular ALP assay. Most of them were inactive; and variable reversal of sclerostin inhibition was seen with some Fabs. Therefore a selection of clones was converted to human/mouse IgG2a format and tested in the same assay. But these clones in the human/mouse IgG2a format could neither fully reverse sclerostin inhibition and the wanted $EC_{50}$ (<10 nM) criterion could not be reached. The best matured candidate MOR05177 (VL matured from parental MOR04518) showed at 50 nM Fab or at 140-467 nM human/mouse IgG2a 75-85% restoration of the ALP signal.

Example 6

Identification of Anti-Sclerostin Antibodies from Parental and Optimized Fabs and IgGs in a New Primary Bio-Assay Based on new publications (Wu at al. JBC 2005, He et al. JBC 2005, Bezooyen et al. ASBMR 2005, Winkler et al. JBC 2005), which show that sclerostin impacts Wnt signaling directly or indirectly, a new functional bioassay was developed.

This assay is based on the ability of sclerostin to inhibit Wnt1-mediated activation of STF in HEK293 cells.

In this assay all Fabs identified in the initial screenings plus all Fabs identified in the affinity maturation were tested. It became obvious the increased affinity of matured Fabs reflected in increased potency and efficacy in the wnt-1 assay.

Testing all parental Fabs identified two further antibodies as promising templates for an additional affinity maturation. FIG. 1 shows the activity of MOR05813_IgG2lambda, one of the most potent antibody identified in the wnt-1 assay.

Example 7

Characterization of Parental and Affinity Matured Fabs in other Bio-Assays

Activity of Parental and Affinity Matured Fabs in Mineralization Assay

The mineralization assay is based on the ability of MC3T3 cells to form a mineralized matrix, indicating their capacity to undergo osteogenic differentiation. A strong mineralization (>1 μg calcium deposited per well (96-well format)) was measured after 14 days at all BMP-2 concentration tested. The addition of increasing sclerostin concentrations induced a dose dependent inhibition of the BMP-2 (2.1 nM) induced mineralization ($IC_{50}$: 120 nM) (data not shown).

FIG. 2 shows an example of mineralization in the presence of MOR05813_Fab. The antibody could restore BMP-2-induced mineralization to maximum 80% of the initial response, whereas an anti-lysozyme Fab used as negative control had no effect.

Activity of Parental and Affinity Matured Fabs in LRP6/Sclerostin ELISA

The LRP6/sclerostin ELISA is based on the ability of sclerostin to bind LRP6. To further characterize the Fabs produced, a selection of Fabs and IgGs were tested in this assay. In the presence of an anti-sclerostin antibody from R&D (1000 ng/ml=~7 nM), sclerostin (0.9 nM) binding to LRP6 was inhibited by 68% compared to control (data not shown).

Figure 3:
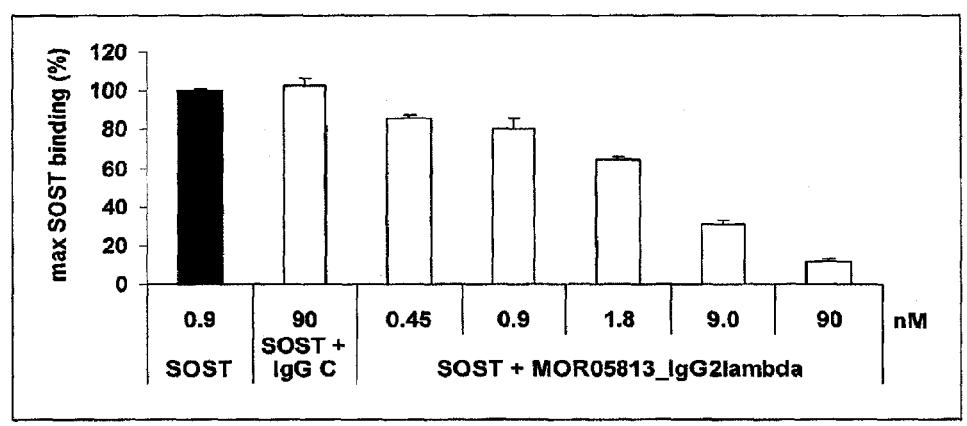
FIG. 3: Effect of MOR05813_IgG2lambda in the LRP6-SOST ELISA

MOR05813_IgG2 lambda inhibited sclerostin binding to LRP6 up to 90% at 90 nM, whereas an anti-lysozyme IgG used as negative control had no effect on sclerostin binding to LRP6 (FIG. 3).

Activity of Parental and Affinity Matured Fabs in Phosoho-Smad1 Assay

The phospho-Smad1 assay (Western) is based on the ability of BMP-6 to induce Smad1 phosphorylation within 15 minutes in MC3T3-E1 cells. MOR05318_IgG2 lambda inhibited sclerostin action on BMP-6-induced Smad1 phosphorylation with an $EC_{50}$ of 115 nM and restaured Smad1 phosphorylation to maximum 66% of the BMP-6-induced phosphorylation. The negative control anti-lysozyme IgG (IgG C) had no effect (FIG. 4).

Example 8

Figure 5:
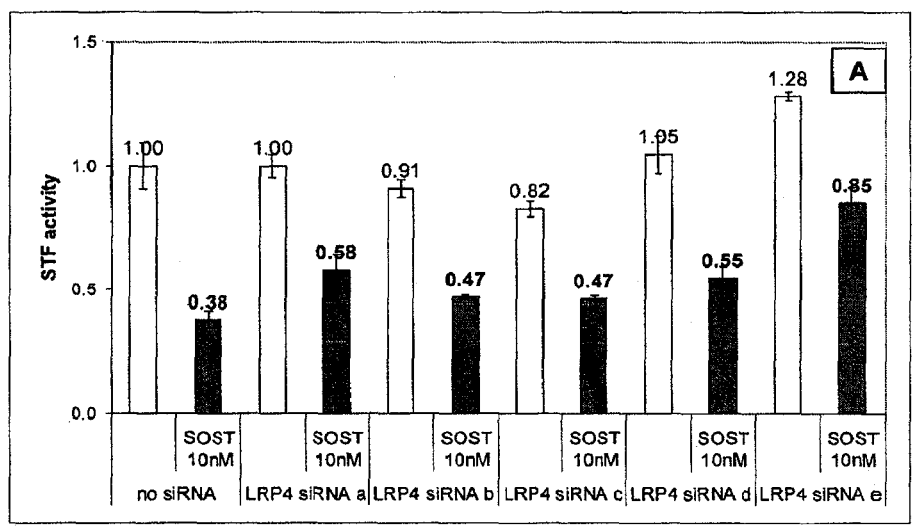
FIG. 5: A—Effect of LRP4 knockdown (siRNA) on SOST inhibitory action in the wnt-1 assay in Hek293 cells (Black numbers: relative to STF activities in the absence of SOST, Bold black numbers: ratio of STF activities in the presence/absence of SOST); B—Specificity of the effect of LRP4 overexpression on SOST $IC_{50}$ and Dkk1 IC50 in the wnt-1 assay in Hek293 cells; C—Specificity of the effect of LRP4 overexpression on SOST and Dkk1 inhibitory action in the wnt-1 assay C28a2 cells; D—Specificity of the effect of LRP4 knockdown (siRNA) on SOST and Dkk1 inhibitory action in the wnt-1 assay in Hek293 cells; E—Modulation of the activity of MOR05813 by LRP4
Figure 5:
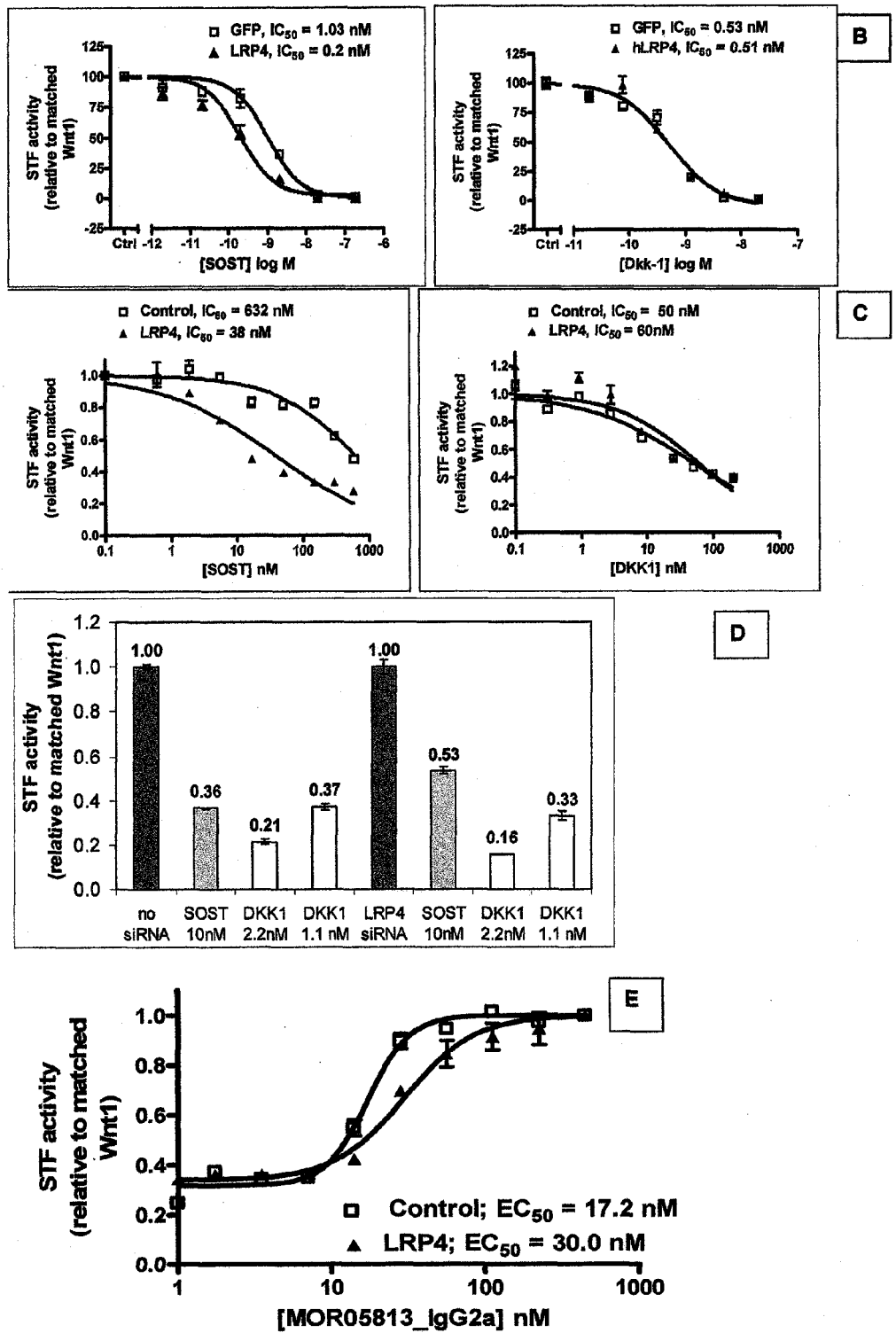

Effect of LRP4, a Novel SOST-Interacting Partner, on the Activity of the Anti-SOST Antibody With the exception of LRP4 siRNA e, LRP4 mRNA knockdown did not affect STF activity in the absence of SOST. However, it did reduce the ability of SOST to inhibit STF activity, between 10 and 30%. This was true for all five siRNA tested alone (FIG. 5A) or in different combinations (data not shown). Upon overexpression LRP4 decreased SOST $IC_{50}$ by 5 and 16 fold in the HEK and c28a2 supertopflash assay, respectively (FIGS. 5B and C). This effect was specific in the sense that overexpressed LRP4 had no effect on DKK1 $IC_{50}$. Knockdown of LRP4 (siRNA) decreased the inhibitory action of SOST in Wnt-1 induced STF, whereas it did not decrease the inhibitory action of DKK1 (FIG. 5D). In turn, LRP4 decreased the action of the anti-SOST antibody by increasing MOR05813_IgG2a $EC_{50}$ from 17.2 nM to 30 nM (FIG. 5E). These data suggest that LRP4 is a facilitator of SOST action.

Example 9

New Maturation

To increase affinity and biological activity of two newly selected antibody fragments based on the results obtained from the bio-assays, LCDR3 and HCDR2 regions were optimized in parallel by cassette mutagenesis using directed mutagenesis (Virnekas et al., 1994), whereby the framework regions were kept constant. Prior to cloning of the maturation libraries, all parental Fab fragments were transferred from the expression vector pMORPH®X9_MH into the CysDisplay™ maturation vector pMORPH®25 via the XbaI/EcoRI restriction sites. This vector provides the phage protein pIII fused N-terminally to a cysteine residue as well as a C-terminal cysteine fused to the Fd antibody chain and thus allows disulfide-linked display of the respective Fab fragments on the phage surface.

For generation of the HCDR2 libraries the HCDR2 region of each parental Fab was excised and replaced by a 590 bp stuffer. This DNA stuffer facilitates the separation of single digested from double digested vector bands and reduces the background of the high-affinity parental Fabs during the maturation pannings. In a subsequent step, the stuffer was excised from the Fab-encoding plasmids of each parental clone and replaced by the highly diversified HCDR2 maturation cassette.

In parallel, the LCDR3 region of five of the four parental clones was replaced by a diversified LCDR3 maturation cassette without intermediate cloning of a stuffer.

Sizes of the maturation libraries ranged between $2 \times 10^7$ and $2 \times 10^8$ clones with a cloning background below 1%, and quality control by sequencing revealed a good quality of each library. For each LCDR3 and HCDR2 maturation library, antibody-displaying phages were prepared and phage titers determined by spot titration.

Panning Strategies for Additional Affinity Maturation

The antibody-displaying phages from the following maturation libraries were subjected to separate pannings and screenings:
Lead 1: MOR04525 (L-CDR3 maturation)
Lead 1: MOR04525 (H-CDR2 maturation)
Lead 2: MOR04529 (L-CDR3 maturation)
Lead 2: MOR04529 (H-CDR2 maturation)

For each lead or pool library three different pannings were performed, for each panning strategy different stringency conditions were applied. To increase the panning stringency and to select for improved off-rates, competition with soluble recombinant sclerostin protein was performed during prolonged incubation and washing periods.

After the pannings the enriched phagemid pools were subcloned into the pMORPH®X9_MH expression vector. About 1600 single clones were picked and Fabs expressed by induction with IPTG.

The affinity criterion of <100 pM for human sclerostin was fulfilled for derivatives of both parental Fabs. The must cross-reactivity with cynomolgus sclerostin and with mouse sclerostin of <500 pM was fulfilled for derivatives of both parental Fabs. MOR04525 yielded in more clones having higher affinities to all three species.

Example 10

Characterization of Anti-Sclerostin Antibodies in In Vivo Studies

Eight-month-old female OF1/IC mice (n=16/group, Charles River, France) were administered twice weekly intravenously anti-sclerostin antibody MOR05813 (24.5 mg/kg, mIgG2a) or isotype control antibody (anti-PC-mIgG2a). Control groups received either daily subcutaneously 100 microg/kg PTH(1-34) or vehicle (PBS+0.1% BSA). Treatment lasted 2.5 weeks for all animals. Half of the animals (n=8/group) was sacrificed at that time point for histomorphometric analysis. These animals had received fluorochrome markers 10 and 3 days prior to necropsy for histomorphometric evaluation of bone formation dynamics. Treatment continued for the remainder of the animals (n=8/group) up to 5 weeks.

Figure 6:
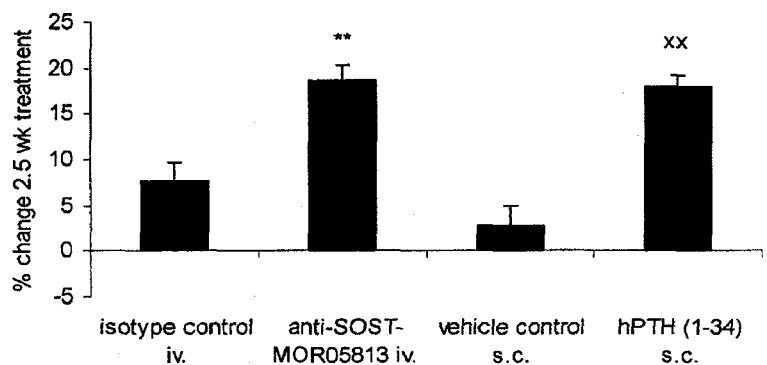
FIG. 6: Mouse study, in vivo pQCT—2.5 weeks treatment with MOR05813 increases total bone mineral content in the proximal tibia metaphysis
Figure 7:
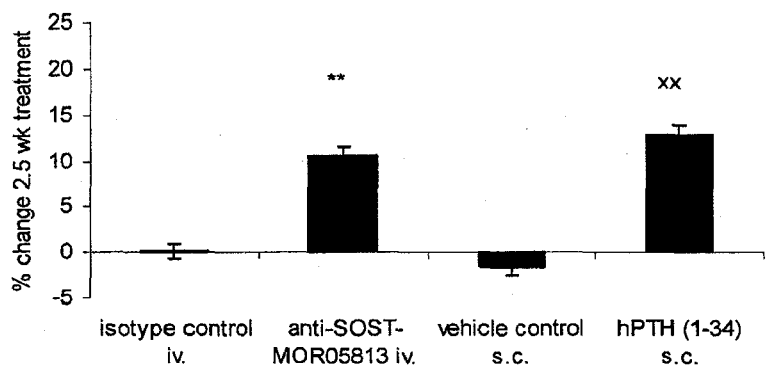
FIG. 7: Mouse study, in vivo pQCT—2.5 weeks treatment with MOR05813 increases total bone mineral density in the proximal tibia metaphysis
Figure 8:
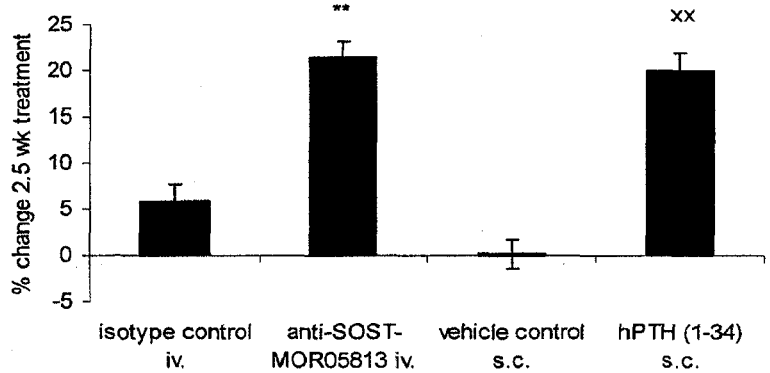
FIG. 8: Mouse study, in vivo pQCT—2.5 weeks treatment with MOR05813 increases cortical thickness in the proximal tibia metaphysis
Figure 9:
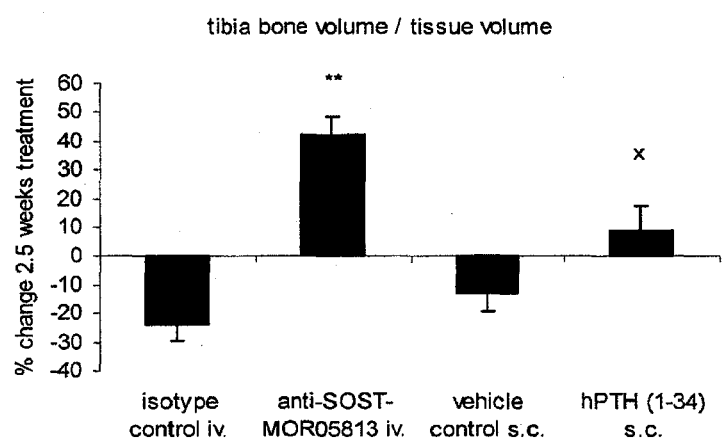
FIG. 9: Mouse study, in vivo uQCT—2.5 weeks treatment with MOR05813 increases cancellous bone volume in the proximal tibia metaphysis

The animals were monitored for changes in bone mass, density and geometry. In vivo peripheral quantitative computed tomography [pQCT] demonstrated that MOR05177 is strongly bone anabolic in the proximal tibia of aged mice increasing bone mineral content (FIG. 6) and density (FIG. 7). The bone anabolic effect occurred both in the cortical (FIG. 8) and cancellous (FIG. 9) bone compartment. These data suggest that the observed inhibitory effect of MOR05813 on sclerostin action in the Wnt signaling reporter assay in non-osteoblastic cells translates into induction of bone formation responses due to sclerostin inhibition in vivo. The magnitude of the bone anabolic response in mice was comparable to bone anabolism induced by a high dose of hPTH (1-34).

Figure 10:
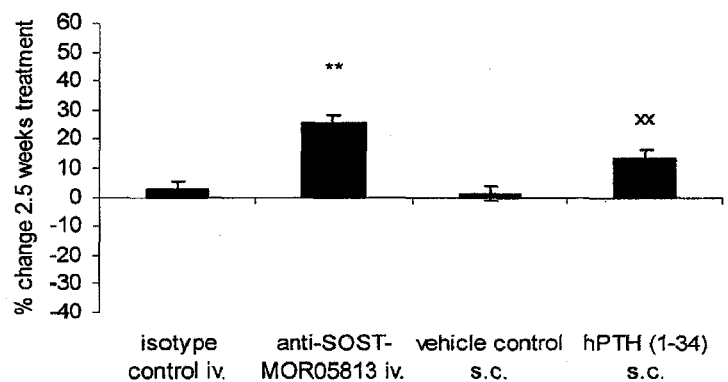
FIG. 10: Mouse study, in vivo uQCT—2.5 weeks treatment with MOR05813 increases trabecular thickness in the proximal tibia metaphysis

MicroCT analysis demonstrated increases in trabecular bone volume (FIG. 9) mainly related to a thickening of trabecular bone structures consistent with bone anabolism (FIG. 10).

Figure 11:
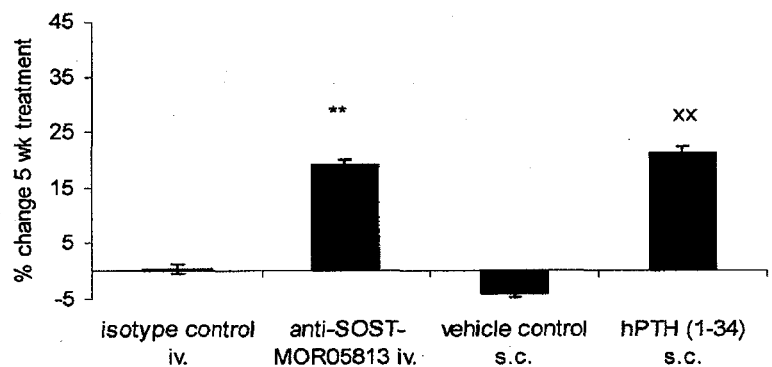
FIG. 11: Mouse study, in vivo pQCT—5 weeks treatment with MOR05813 increases total bone mineral density further in the proximal tibia metaphysis
Figure 12:
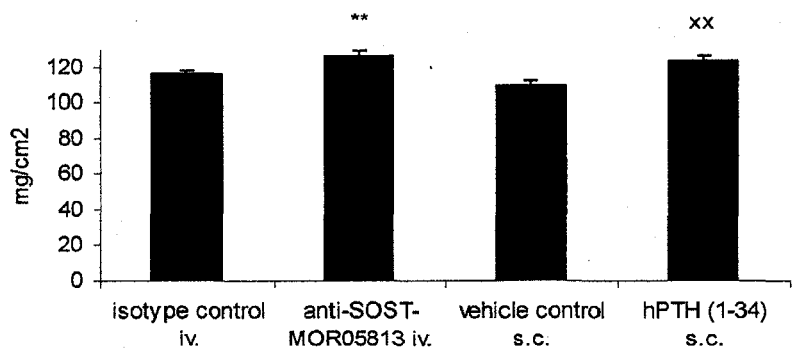
FIG. 12: Mouse study, ex vivo DEXA—5 weeks treatment with MOR05813 increases bone mineral density further in the tibia
Figure 13:
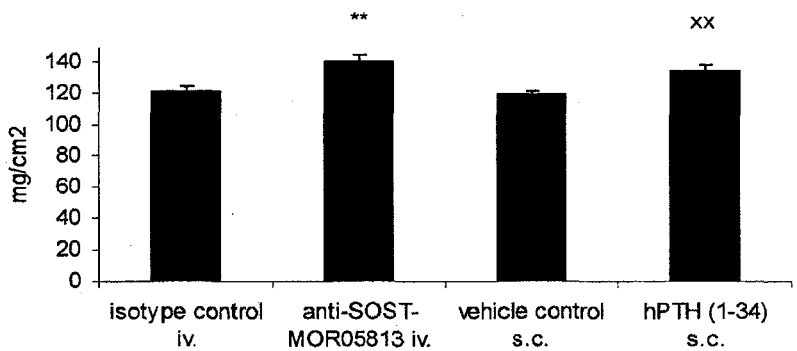
FIG. 13: Mouse study, ex vivo DEXA—5 weeks treatment with MOR05813 increases bone mineral density further in the femur
Figure 14:
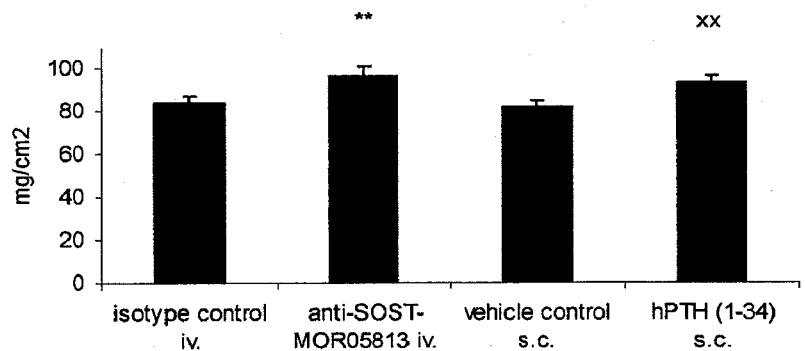
FIG. 14: Mouse study, ex vivo DEXA—5 weeks treatment with MOR05813 increases bone mineral density further in the spine

Bone mineral density increased further in animals, which were treated up to 5 weeks (FIG. 11). Bone mineral density as evaluated ex vivo by DEXA was increased in the appendicular (tibia, femur) and axial (lumbar vertebrae) skeleton (FIG. 12-14). The effect was comparable to the one measured in the positive control group treated daily with 100 microg/kg hPTH (1-34).

Figure 15:
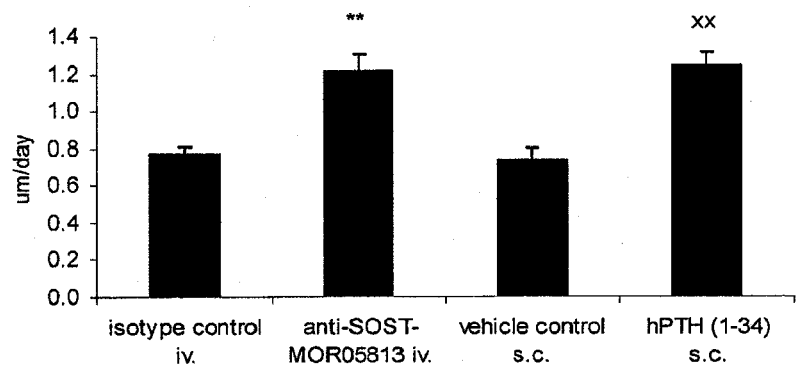
FIG. 15: Mouse study, ex vivo histomorphometry—2.5 weeks treatment with MOR05813 increases bone formation rates in the appendicular skeleton (distal femur metaphysis)
Figure 16:
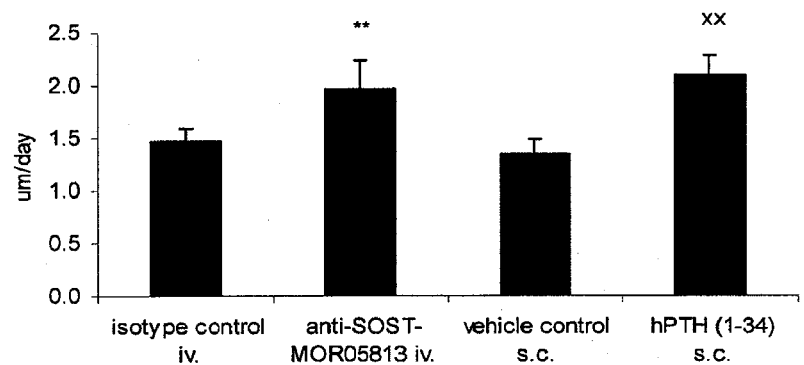
FIG. 16: Mouse study, ex vivo histomorphometry—2.5 weeks treatment with MOR05813 increases mineral apposition rate in the appendicular skeleton (distal femur metaphysis)
Figure 17:
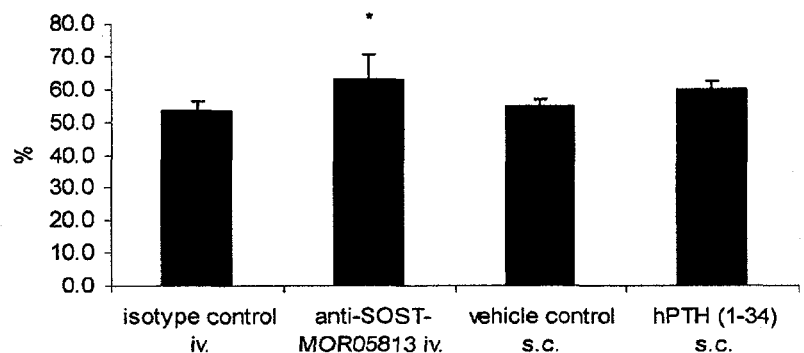
FIG. 17: Mouse study, ex vivo histomorphometry—2.5 weeks treatment with MOR05813 increases mineralizing surface in the appendicular skeleton (distal femur metaphysis)
Figure 18:
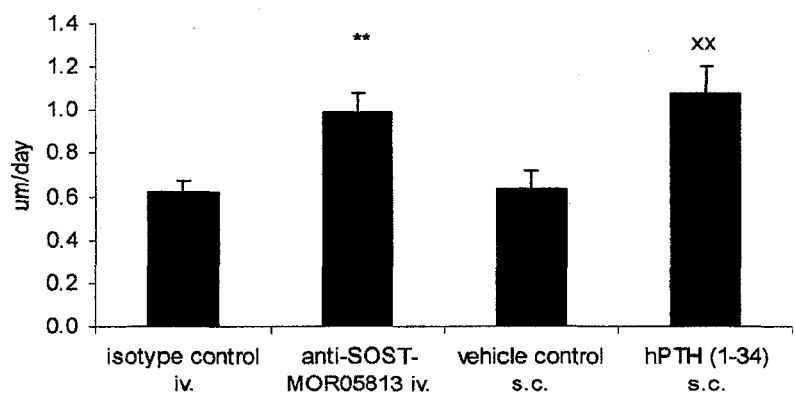
FIG. 18: Mouse study, ex vivo histomorphometry—2.5 weeks treatment with MOR05813 increases bone formation rates in the axial skeleton (lumbar vertebra)
Figure 19:
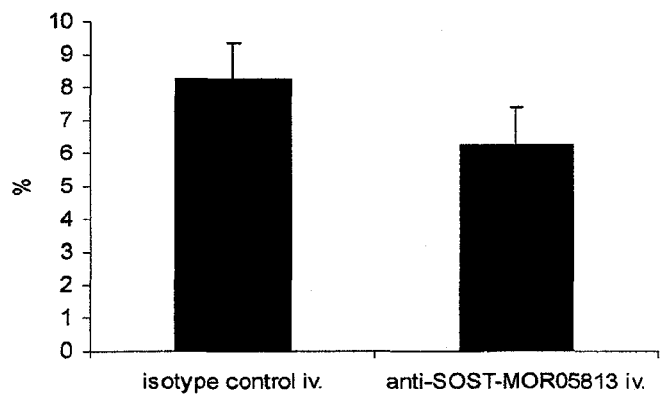
FIG. 19: Mouse study, ex vivo histomorphometry—2.5 weeks treatment with MOR05813 does not affect bone resorption in the appendicular skeleton (distal femur metaphysis), as measured by osteoclast surface

Histomorphometric fluorochrome marker based analyses of bone formation dynamics demonstrated that the bone mass gain was due to a substantial increase in bone formation rates in the appendicular (FIG. 15) and axial skeleton (FIG. 18). The effects were comparable to those of a high dose of PTH (1-34). Increases in bone formation rates were both related to increases in mineral appostion rates (FIG. 16) and mineralizing surface (FIG. 17). Bone resorption was not increased by the treatment as demonstrated by osteoclast surface measurement (FIG. 19).

Example 11

Screening Antibodies that Cross-Block Sclerostin Binding Antibodies of the Present Invention Biacore Cross-Blocking Assay The following generally describes a suitable Biacore assay for determining whether an antibody or other binding agent cross-blocks or is capable of cross-blocking antibodies according to the invention. It will be appreciated that the assay can be used with any of the sclerostin binding agents described herein.

The Biacore machine (for example the BIAcore 3000) is operated in line with the manufacturer's recommendations.

Sclerostin may be coupled to e.g. a CM5 Biacore chip by way of routinely used amine coupling chemistry, e.g. EDC-NHS amine couplilng, to create a sclerostin-coated surface. In order to obtain measurable levels of binding, typically 200-800 resonance units of sclerostin may be coupled to the chip (this amount gives measurable levels of binding and is at the same time readily saturable by the concentrations of test reagent being used).

An alternative way of attaching sclerostin to the BIAcore chip is by using a "tagged" version of sclerostin, for example N-terminal or C-terminal His-tagged Sclerostin. In this format, an anti-His antibody would be coupled to the Biacore chip and then the His-tagged sclerostin would be passed over the surface of the chip and captured by the anti-His antibody.

The two antibodies to be assessed for their ability to cross-block each other are mixed in a stoichiometrical amount, e.g. at a one to one molar ratio, of binding sites in a suitable buffer to create the test mixture. The buffer used is typically a buffer which is normally used in protein chemistry, such as e.g. PBS (136 mM NaCl, 2.7 mM KCl, 10 mM $Na_2HPO_4$, 1.76 mM KH$_2$PO$_4$, pH 7.4). When calculating the concentrations on a binding site-basis the molecular weight of an antibody is assumed to be the total molecular weight of the antibody divided by the number of target (i.e. sclerostin) binding sites on that antibody.

The concentration of each antibody in the test mixture should be high enough to ensure saturation of the binding sites for that antibody on the sclerostin molecules which are bound on the BIAcore chip. The antibodies in the mixture are at the same molar concentration (on a binding basis) and that concentration would typically be between 1.0 mM and 1.5 mM (on a binding site basis).

Separate solutions containing the separate antibodies on their own are also prepared. The buffer used for these separate solutions should be the same buffer and at the same concentration as was used for the test mixture.

The test mixture is passed over the sclerostin-coated BIAcore chip and the binding recorded. The bound antibodies are thereafter removed by treating the chip with e.g. an acid, such as 30 mM HCl for about 1 minute. It is important that the sclerostin molecules which are bound to the chip are not damaged.

The solution of the first antibody alone is then passed over the sclerostin-coated surface and the binding is recorded. Thereafter, the chip is treated to remove all of the bound antibody without damaging the chip-bound sclerostin, e.g. by way of above mentioned acid treatment.

The solution of the second antibody alone is then passed over the sclerostin-coated surface and the amount of binding recorded.

The maximal theoretical binding can be defined as the sum of the binding to sclerostin of each antibody separately. This is then compared to the actual binding of the mixture of antibodies measured. If the actual binding is lower than that of the theoretical binding, the two antibodies are cross-blocking each other.

ELISA-Based Cross-Blocking Assay

Cross-blocking of an anti-sclerostin antibody or another sclerostin binding agent may also be detected by using an ELISA assay.

The general principle of the ELISA-assay involves coating an anti-sclerostin antibody onto the wells of an ELISA plate. An excess amount of a second, potentially cross-blocking, anti-sclerostin antibody is then added in solution (i.e. not bound to the ELISA plate). A limited amount of sclerostin is then added to the wells.

The antibody which was coated onto the wells and the antibody in solution will compete for binding of the limited number of sclerostin molecules. The plate is then washed to remove sclerostin that has not bound to the coated antibody and to also remove the second, solution phase, antibody as well as any complexes formed between the second, solution phase antibody and sclerostin. The amount of bound sclerostin is then measured using an appropriate sclerostin detection reagent. An antibody in solution that is able to cross-block the coated antibody will be able to cause a decrease in the number of sclerostin molecules that the coated antibody can bind relative to the number of sclerostin molecules that the coated antibody can bind in the absence of the second, solution phase, antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y sclerostin binding sites per well are at least 10 fold higher than the moles of Ab-X sclerostin binding sites that were used, per well, during the coating of the ELISA plate. Sclerostin is then added such that the moles of sclerostin added per well are at least 25-fold lower than the moles of Ab-X sclerostin binding sites that were used for coating each well. Following a suitable incubation period, the ELISA plate is washed and a sclerostin detection reagent is added to measure the amount of sclerostin specifically bound by the coated anti-sclerostin antibody (in this case Ab-X). The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Example 12

ELISA to Detect the Effect of MOR05813_IgG2lambda on SOST Binding of LRP6

LRP6/Sclerostin ELISA

Ninety six-well microtiter non-treated plates were coated with 100 μl/well LRP6/Fc (1 μg/ml, R&D Systems, Cat#1505-LR) diluted in PBS. As control for non-specific binding (NSB), a few wells were filled with 100 μl/well PBS. The plates were covered with plastic film and incubated overnight at RT. Following the coating, plates were washed 3 times with 200 μl/well 0.05% Tween 20 (Fluka, Cat#93773) in PBS and wells were blocked for 1 h at 37° C. by adding 300 μl/well SuperBlock blocking buffer (Pierce, Cat#37535) in TBS. After incubation, the block solution was removed and 100 μl/well sclerostin (E. coli derived, Novartis; 1-1000 ng/ml) diluted in 1% BSA in PBS were added. The plates were incubated for 2 h at RT before being washed 3 times with 200 μl/well 0.05% Tween 20 in PBS. Afterwards, 100 μl/well anti sclerostin antibody (1 μg/ml) diluted in 1% BSA in PBS were added and plates incubated for 2 h at RT before being washed 3 times with 200 μl/well 0.05% Tween 20 in PBS. Finally, 100 μl/well ALP conjugated anti Goat IgG Ab (1:5000; Sigma Cat#A-7888) diluted in 1% BSA (Sigma Cat. Nb.:A-7888) in PBS were added for 1 h at RT and plates were then washed 3 times with 200 μl/well 0.05% Tween 20 in PBS. To determine ALP, 100 μl/well ALP substrate (Sigma, Cat#S0942) solution (1 tablet per 5 ml diethanolamine substrate buffer 1×; Pierce, Cat#34064) was added to the plates for 90 min and optical density measured at 405 nm.

Activity of Parental and Affinity Matured Fabs in LRP6/Sclerostin ELISA

Figure 20:
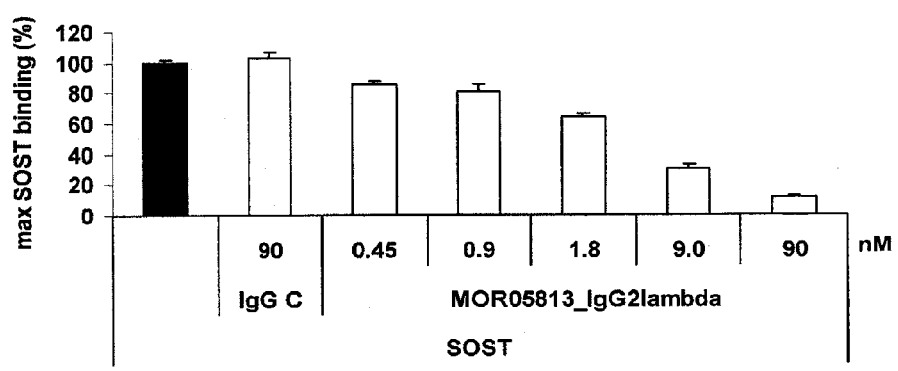
FIG. 20: ELISA showing effect of MOR05813_IgG2lambda on SOST binding of LRP6. 0.9 nM SOST was used in each case

The LRP6/sclerostin ELISA is based on the ability of sclerostin to bind LRP6. To further characterize the Fabs produced, a selection of Fabs and IgGs were tested in this assay. In the presence of an anti-sclerostin antibody from R&D (1000 ng/ml=~7 nM), sclerostin (0.9 nM) binding to LRP6 was inhibited by 68% compared to control (data not shown). MOR05813_IgG2 lambda inhibited sclerostin binding to LRP6 up to 90% at 90 nM, whereas an anti-lysozyme IgG used as negative control had no effect on sclerostin binding to LRP6 (FIG. 20).

Example 13

Co-Treatment Using MOR05813

MOR05813+Zoledronic Acid

Eight-month-old female OF1/IC mice (n=10/group, Charles River, France) were ovariectomized to induce bone loss by estrogen deprival or left intact. The animals were administered twice weekly intravenously anti-sclerostin antibody MOR05813 (24 mg/kg, h/mIgG2a) or control antibody (anti-PC-h/mIgG2a, intact and OVX control groups). Additional groups received either a single application of zoledronic acid alone (100 µg/kg) or in combinaton with the anti-sclerostin antibody MOR05813. Antibody treatment lasted 3.5 weeks (7 applications).

Tibial bone mass and geometry of the animals was measured prior to ovariectomy by peripheral quantitative computed tomography (pQCT). Animals were distributed evenly according to body weight and tibial total bone mineral density into groups. Bone mineral density, mass and geometry changes were evaluated at the end of the treatment period.

Results are expressed as mean+/−SEM. Statistical analysis was carried out using RS1 (series 1999 for Windows, Domain Manufacturing Corp., USA). The data were subjected to one-way analysis of variance (ANOVA). Equality of variances was tested by Levene F-test and differences between groups using the Bonferroni-adjusted Dunnett test. Treated groups were tested for significance of differences from the control antibody treated OVX group ($p<0.05^*$, $p<0.01^{**}$).

Ovariectomy induced bone loss can be blocked by the antibody treatment in aged mice (FIG. 21). When the antibody is used in combination with a single intravenous injection of the bisphosphonate zoledronic acid, bone loss is blocked and bone gain is induced as indicated by increases in total bone mineral content (FIG. 21 A) and density (FIG. 21 B) as well as increases in cortical thickness (FIG. 21 C) and cancellous bone mineral density (FIG. 21 D).

MOR05813+Alendronate Pre-Treatment 4.5-month-old female OF1/IC mice (n=10/group, Charles River, France) were administered twice weekly intravenously anti-sclerostin antibody MOR05813 (10 mg/kg, h/mIgG2a) or control antibody (anti-PC-mIgG2a, intact and OVX control groups). Additional groups had received 7 weeks alendronate pre-treatment (4 µg/kg/day; 5 days/week) before receiving either the control antibody or anti-sclerostin antibody MOR05813. Antibody treatment lasted 3.5 weeks (7 applications).

Tibial bone mass and geometry of the animals was measured prior to initiation of antibody treatment by peripheral quantitative computed tomography (pQCT). Animals were distributed evenly according to body weight and tibial total bone mineral density into groups. Bone mineral density, mass and geometry changes were evaluated at the end of the treatment period.

Results are expressed as mean+/−SEM. Statistical analysis was carried out using RS1 (series 1999 for Windows, Domain Manufacturing Corp., USA). The data were subjected to one-way analysis of variance (ANOVA). Equality of variances was tested by Levene F-test and differences between groups using the Bonferroni-adjusted Dunnett test. Alendronate pre-treated groups were tested for significance of difference from the groups receiving no pretreatment ($p<0.05^*$, $p<0.01^{**}$).

Long-term pretreatment with the bisphosphonate alendronate does not have negative impact on the bone anabolic action of the anti-sclerostin MOR05813 as reflected by increases in total bone mineral content (FIG. 22 A) and density (FIG. 22 B) as well as increases in cortical thickness (FIG. 22 C) and cancellous bone mineral density (FIG. 22 D). Due to the persisting anti-resorptive properties of the bisphosphonate beyond the administration period, an increase is observed in total bone mineral content (FIG. 22 A) and cortical thickness (FIG. 22 C).

MOR05813+DKK1 or hPTH

Six-month-old female nude mice (n=8/group) were administered twice weekly intravenously vehicle, anti-sclerostin antibody MOR05813 (10, 20 and 40 mg/kg, IgG2), anti-Dkk1 antibody (10 mg/kg, IgG1), hPTH(1-34) (100 microg/kg) or combinations thereof. Antibody treatment lasted 4 weeks (8 applications).

Tibial bone mass and geometry of the animals was measured prior to treatment by peripheral quantitative computed tomography (pQCT). Animals were distributed evenly according to body weight and tibial total bone mineral density into groups. Bone mineral density, mass and geometry changes were evaluated at the end of the treatment period.

Results are expressed as mean+/−SEM. Statistical analysis was carried out using RS1 (series 1999 for Windows, Domain Manufacturing Corp., USA). The data were subjected to one-way analysis of variance (ANOVA). Equality of variances was tested by Levene F-test and differences between groups using the Bonferroni-adjusted Dunnett test. Groups were tested for significance of difference from the vehicle treated group ($p<0.05^*$, $p<0.01^{**}$).

Bone anabolic effects increase with dose of anti-sclerostin MOR05813 (FIG. 23). Co-treatment with an anti-Dkk1 antibody results in an improved increase in total bone mineral content (FIG. 23 A) and density (FIG. 23 B) and cortical thickness (FIG. 23 C) and a synergistic increase in cancellous bone mineral density (FIG. 23 D). Co-treatment with hPTH (1-34) results in a synergistic increase in all measured parameters (FIG. 23 A-D).

REFERENCES

Avsian-Kretchmer O, Hsuch A J (2004) Comparative genomic analysis of the eight-membered ring cystine knot-containing bone morphogenetic protein antagonists. Mol Endocrinol 18(1):1-12.

Ausubel, F. M., Brent, R., Kingston, R. E., Moore, D. D., Seidman, J. G., Smith, J. A., Struhl, K., (1998) Current Protocols in Molecular Biology, Wiley, New York, USA Balemans W, Ebeling M, Patel N, Van Hul E, Olson P, Dioszegi M, Lacza C, Wuyts W, Van Den Ende J, Willems P, Paes-Alves A F, Hill S, Bueno M, Ramos F J, Tacconi P, Dikkers F G, Stratakis C, Lindpaintner K, Vickery B, Foernzler D, Van Hul W. (2001) Increased bone density in sclerosteosis is due to the deficiency of a novel secreted protein (SOST). Hum Mol. Genet. 10(5):537-43

Balemans W, Patel N, Ebeling M, Van Hul E, Wuyts W, Lacza C, Dioszegi M, Dikkers F G, Hildering P, Willems P J, Verheij J B, Lindpaintner K, Vickery B, Foernzler D, Van Hul W. (2002) Identification of a 52 kb deletion downstream of the SOST gene in patients with van Buchem disease. J Med Gene 39(2):91-7.

Brunkow M E, Gardner J C, Van Ness J, Paeper B W, Kovacevich B R, Proll S, Skonier J E, Zhao L, Sabo P J, Fu Y, Alisch R S, Gillett L, Colbert T, Tacconi P, Galas D, Hamersma H, Beighton P, Mulligan J (2001) Bone dysplasia sclerosteosis results from loss of the SOST gene product, a novel cystine knot-containing protein. Am J Hum Genet. 68(3):577-89.

Chen, B. P., Hai, T. Expression vectors for affinity purification and radiolabeling of proteins using *Escherichia coli* as host. Gene 139, 73-75. 1994

Chen, Y., Wiesmann, C., Fuh, G., Li, B., Christinger, H. W., McKay, P., de Vos, A. M., Lowman, H. B. (1999). Selection and analysis of an optimized anti-VEGF antibody: crystal structure of an affinity-matured Fab in complex with antigen. J. Mol. Biol. 293, 865-881

Gardner J C, van Bezooijen R L, Mervis B, Hamdy N A, Lowik C W, Hamersma H, Beighton P, Papapoulos S E. (2005) Bone mineral density in sclerosteosis; affected individuals and gene carriers. J Clin Endocrinol Metab 90(12): 6392-5

Haenel C, Satzger M, Della Ducata D, Ostendorp R and Brocks B (2005) Chraterization of High Affinity Antibodies by Electrochemiluminescence-Based Equilibrium Titration. Anal Biochem 339(1):182-4

Keller H, Kneissel M. (2005) SOST is a target gene for PTH in bone. Bone 37(2):148-58.

Knappik, A., Ge, L., Honegger, A., Pack, P., Fischer, M., Wellnhofer, G., Hoess, A., Wolle, J., Pluckthun, A., and Virnekas, B. (2000). Fully synthetic human combinatorial antibody libraries (HuCAL®) based on modular consensus frameworks and CDRs randomized with trinucleotides. J Mol Biol 296, 57-86.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Sohlemann, P., Winter, J., Wolle, J., and Kretzschmar, T. (2001). High-throughput generation and engineering of recombinant human antibodies. J Immunol Methods 254, 67-84.

Li X, Zhang Y, Kang H, Liu W, Liu P, Zhang J, Harris S E, Wu D (2005) Sclerostin binds to LRP5/6 and antagonizes canonical Wnt signaling. J Biol. Chem. 20; 280(20):19883-7

Löhning, C. (2001). Novel methods for displaying (poly) peptides/proteins on bacteriophage particles via disulfide bonds. WO 01/05950.

Loots G G, Kneissel M, Keller H, Baptist M, Chang J, Collette N M, Ovcharenko D, Plajzer-Frick I, Rubin E M. (2005) Genomic deletion of a long-range bone enhancer misregulates sclerostin in Van Buchem disease. Genome Res 15(7):928-35

Low, N. M., Holliger, P., Winter, G. (1996). Mimicking somatic hypermutation: affinity maturation of antibodies displayed on bacteriophage using a bacterial mutator strain. J. Mol. Biol. 260, 359-368

Rauchenberger, R., Borges, E., Thomassen-Wolf, E., Rom, E., Adar, R., Yaniv, Y., Malka, M., Chumakov, I., Kotzer, S., Resnitzky, D., Knappik, A., Reiffert, S., Prassler, J., Jury, K., Waldherr, D., Bauer, S., Kretzschmar, T., Yayon, A., and Rothe, C. (2003). Human combinatorial Fab Library yielding specific and functional antibodies against the human fibroblast growth factor receptor 3. J Biol. Chem. 278(40): 38194-38205

Semenov M V, He X. LRP5 mutations linked to high bone mass diseases cause reduced LRP5 binding and inhibition by SOST. J Biol. Chem. 2006 Oct. 19;

van Bezooijen R L, Svensson J P, Eefting D, Visser A, van der Horst G, Karperien M, Quax P H, Vrieling H, Papapoulos S E, Ten Dijke P, Lowik C W (2006) Wnt but not BMP Signaling is Involved in the Inhibitory Action of Sclerostin on BMP-Stimulated Bone Formation.

Virnekas B, Ge L, Pluckthun A, Schneider K C, Wellnhofer G, Moroney S E (1994) Trinucleotide phosphoramidites: ideal reagents for the synthesis of mixed oligonucleotides for random mutagenesis. Nucleic Acids Res. 22(25):5600-5607

Bone Miner Res 2006 Oct. 10 Winkler D G, Sutherland M K, Geoghegan J C, Yu C, Hayes T, Skonier J E, Shpektor D, Jonas M, Kovacevich B R, Staehling-Hampton K, Appleby M, Brunkow M E, Latham J A. (2003) Osteocyte control of bone formation via sclerostin, a novel BMP antagonist.

EMBO J. 22(23):6267-76 Winkler D G, Sutherland M S, Ojala E, Turcott E, Geoghegan J C, Shpektor O, Skonier J E, Yu C, Latham J A (2005) Sclerostin inhibition of Wnt-3a-induced $C_3H_{10}T1/2$ cell differentiation is indirect and mediated by bone morphogenetic proteins. J Biol. Chem. 28; 280(4):2498-502

---

The invention claimed is:

1. An isolated polynucleotide comprising:
   a) a nucleic acid sequence having at least 80% identity with the nucleic acid sequence set forth as SEQ ID NO:92 and which encodes a $V_H$ polypeptide comprising the amino acid sequence as set forth as SEQ ID NO:70, or the complement thereof;
   b) a nucleic acid sequence having at least 80% identity with the nucleic acid sequence set forth as SEQ ID NO:103 and which encodes a $V_L$ polypeptide comprising the amino acid sequence as set forth as SEQ ID NO:81, or the complement thereof;
   c) both a) and b);
   d) a nucleic acid sequence having at least 80% identity with the nucleic acid sequence set forth as SEQ ID NO:136 and which encodes a full length heavy chain polypeptide comprising the amino acid sequence as set forth as SEQ ID NO:114, or the complement thereof;
   e) a nucleic acid sequence having at least 80% identity with the nucleic acid sequence set forth as SEQ ID NO:147 and which encodes a full length light chain polypeptide comprising the amino acid sequence as set forth as SEQ ID NO:125, or the complement thereof; or
   f) both d) and e).

2. The isolated polynucleotide according to claim 1, wherein the identity is at least 90%.

3. The isolated polynucleotide according to claim 2, wherein the identity is at least 95%.

4. A cloning or expression vector comprising the isolated polynucleotide of claim 1.

5. A host cell comprising the vector according to claim 4.

6. A process for the production of a protein, comprising culturing a host cell comprising a vector comprising a polynucleotide, wherein the polynucleotide comprises:
   a) a nucleic acid sequence having at least 80% identity with the nucleic acid sequence set forth as SEQ ID NO:92 and which encodes a $V_H$ polypeptide comprising the amino acid sequence as set forth as SEQ ID NO:70;
   b) a nucleic acid sequence having at least 80% identity with the nucleic acid sequence set forth as SEQ ID NO:103 and which encodes a V<sub>L</sub> polypeptide comprising the amino acid sequence as set forth as SEQ ID NO:81;
c) both a) and b);
d) a nucleic acid sequence having at least 80% identity with the nucleic acid sequence set forth as SEQ ID N0:136 and which encodes a full length heavy chain polypeptide comprising the amino acid sequence as set forth as SEQ ID NO:114;
e) a nucleic acid sequence having at least 80% identity with the nucleic acid sequence set forth as SEQ ID NO:147 and which encodes a full length light chain polypeptide comprising the amino acid sequence as set forth as SEQ ID NO:125; or
f) both d) and e);
under conditions wherein said polynucleotide is translated to said protein.

7. An isolated polynucleotide comprising:
a) the nucleic acid sequence set forth as SEQ ID NO:92 or the complement thereof;
b) the nucleic acid sequence set forth as SEQ ID NO:103 or the complement thereof;
c) both a) and b):
d) the nucleic acid sequence set forth as SEQ ID NO:136 or the complement thereof;
e) the nucleic acid sequence set forth as SEQ ID NO:147 or the complement thereof; or
f) both d) and e).

8. A cloning or expression vector comprising the isolated polynucleotide of claim 7.

9. A host cell comprising the vector according to claim 8.

10. A process for the production of a protein, comprising culturing a host cell comprising a vector comprising a polynucleotide, wherein the polynucleotide comprises:
a) the nucleic acid sequence set forth as SEQ ID NO:92;
b) the nucleic acid sequence set forth as SEQ ID NO:103;
c) both a) and b);
d) the nucleic acid sequence set forth as SEQ ID NO:136;
e) the nucleic acid sequence set forth as SEQ ID NO:147; or
f) both d) and e);
under conditions wherein said polynucleotide is translated to said protein.

11. An isolated polynucleotide consisting of:
a) the nucleic acid sequence set forth as SEQ ID NO:92 or the complement thereof;
b) the nucleic acid sequence set forth as SEQ ID NO:103 or the complement thereof;
c) both a) and b);
d) the nucleic acid sequence set forth as SEQ ID NO:138 or the complement thereof;
e) the nucleic acid sequence set forth as SEQ ID NO:147 or the complement thereof; or
f) both d) and e).

12. A cloning or expression vector comprising the isolated polynucleotide of claim 11.

13. A host cell comprising the vector according to claim 12.

14. A process for the production of a protein, comprising culturing a host cell comprising a vector comprising a polynucleotide, wherein the polynucleotide consists of:
a) the nucleic acid sequence set forth as SEQ ID NO:92;
b) the nucleic acid sequence set forth as SEQ ID NO:103;
c) bath a) and b);
d) the nucleic acid sequence set forth as SEQ ID NO:136;
e) the nucleic acid sequence set forth as SEQ ID NO:147; or
f) both d and e),
under conditions wherein said polynucleotide is translated to said protein.

15. An isolated polynucleotide comprising a nucleic acid sequence that encodes:
a) a V<sub>H</sub> polypeptide comprising the amino acid sequence as set forth as SEQ ID NO:70;
b) a V<sub>L</sub> polypeptide comprising the amino acid sequence as set forth as SEQ ID NO:81; or
c) both a) and b).

16. A cloning or expression vector comprising the isolated polynucleotide of claim 15.

17. A host cell comprising the vector according to claim 16.

18. A process for the production of an antibody or antigen binding portion thereof, comprising culturing the host cell of claim 17 under conditions wherein said polynucleotide is translated to said antibody or antigen binding portion thereof.

19. An isolated polynucleotide comprising a nucleic acid sequence that encodes:
a) a V<sub>H</sub> polypeptide comprising, in sequence,
 (i) an amino acid sequence consisting of SEQ ID NO:4;
 (ii) an amino acid sequence consisting of SEQ ID NO:15; and
 an amino acid sequence consisting of SEQ ID NO:26;
b) a V<sub>L</sub> polypeptide comprising, in sequence,
 (i) an amino acid sequence consisting of SEQ ID NO:37;
 (ii) an amino acid sequence consisting of SEQ ID NO:48; and
 (iii) an amino acid sequence consisting of SEQ ID NO:59; or
c) both a) and b).

\* \* \* \* \*